United States Patent [19]

Hecker et al.

[11] Patent Number: 5,607,926
[45] Date of Patent: Mar. 4, 1997

[54] CEPHALOSPORIN ANTIBIOTICS

[75] Inventors: Scott J. Hecker, Los Gatos; In-Seop Cho, Mountain View, both of Calif.; Burton G. Christensen, Lebanon, N.J.; Tomasz W. Glinka, Sunnyvale, Calif.

[73] Assignee: Microcide Pharmaceuticals, Inc., Mountain View, Calif.

[21] Appl. No.: 413,714

[22] Filed: Mar. 29, 1995

Related U.S. Application Data

[63] Continuation-in-part of Ser. No. 369,798, Jan. 6, 1995, which is a continuation-in-part of Ser. No. 222,262, Apr. 1, 1994, abandoned.

[51] Int. Cl.$^6$ .................... C07D 501/60; A61K 31/545
[52] U.S. Cl. .................... 514/205; 514/203; 540/226; 540/224; 540/227
[58] Field of Search .................... 540/227, 226; 514/205

[56] References Cited

U.S. PATENT DOCUMENTS

| | | | |
|---|---|---|---|
| 3,992,377 | 11/1976 | Chauvette et al. | 260/243 C |
| 4,066,641 | 1/1978 | Hamashima et al. | 540/226 |
| 4,123,528 | 10/1978 | Cama et al. | 424/248.52 |
| 4,150,156 | 4/1979 | Beattie et al. | 424/246 |
| 4,153,714 | 5/1979 | Ponsford | 424/274 |
| 4,256,739 | 3/1981 | Woodward et al. | 424/200 |
| 4,782,145 | 11/1988 | Brighty et al. | 540/214 |
| 4,870,168 | 9/1989 | Baker et al. | 540/222 |
| 4,992,542 | 2/1991 | Christensen et al. | 540/350 |
| 5,025,006 | 6/1991 | Dininno et al. | 514/210 |
| 5,077,287 | 12/1991 | Ternansky | 514/210 |
| 5,162,521 | 11/1992 | Farina et al. | 540/226 |
| 5,205,006 | 4/1993 | Panasuk | 7/108 |

FOREIGN PATENT DOCUMENTS

| | | |
|---|---|---|
| 0009008 | 3/1980 | European Pat. Off. . |
| 0182301 | 5/1986 | European Pat. Off. . |
| 0214462 | 3/1987 | European Pat. Off. . |
| 0010312 | 4/1990 | European Pat. Off. . |
| 0504404 | 9/1992 | European Pat. Off. . |
| 0527686 | 2/1993 | European Pat. Off. . |
| 0560365 | 9/1993 | European Pat. Off. . |
| 2282895 | 3/1976 | France . |
| 2293935 | 7/1976 | France . |
| 61-33190 | 2/1986 | Japan . |
| 61-63684 | 4/1986 | Japan . |
| 4261182 | 9/1992 | Japan . |
| 733777 | 3/1995 | Japan . |
| 0605998 | 8/1974 | Switzerland . |
| 0605999 | 8/1974 | Switzerland . |
| 9109037 | 6/1991 | WIPO . |

OTHER PUBLICATIONS

Aszodi et al., "Synthesis and Antibacterial Activity of Iso-cephems," *Recent Advances in the Chemistry of β–Lactam Antibiotics*, Special Publication No. 70, pp. 350–364, Cambridge, England, Jul. 3–6 (1988).

Afonso et al., "New Synthesis of Penems, the Oxalimide Cyclization Reaction," *J. Amer. Chem. Soc.* 104:6138–6139 (1982) Publication month not provided.

Baldwin and Cooper, "Direct 6–Methoxylation of Penicillin Derivatives. A Convenient Patnway to Substituted β–Lacatm Antibiotics," *J. Amer. Chem. Soc.* 95:2401–2404 (1973) Publication month not proivded.

Barrett, A. G. M., "Amide Transacylation in Penicillin and Cephalosporin Derivatives," *J.C.S. Perkin I* pp. 1629–1633 (1979) Publication month not proivded.

Basker et al., "Synthesis and Antibacterial Activity of C–2 Carboxyethenylthio–Carbapenem Derivatives," *J. Antibiotics* XLIII:847–857 (1990) Publication month not proivded.

Bateson et al., "Synthesis of 7–Oxo–3–sulphinyl–1–azabicyclo[3.2.0]hept–2–ene–2–carboxylates: Olivanic Acid Analogues," *J.C.S. Chem. Comm.* 185–186 (1980) Publication month not provided.

Chauvette, "Chemistry of Cephalosporin Antibiotics. XXI. Conversion of Penicillin to Cephalexin," *J. Org. Chem.* 36:1259–1267 (1971) Publication month not provided.

Chen et al., "Study of Preparative Separation of Cephalosporins By Centrifugal TLC," *Kangshengsu* 14:161–167 (1989) Publication month not provided.

Doyle et al., "Nuclear analogs of β–lactam antibiotics. XIII. Structure activity relationships in the isocephalosporin series," *Can. J. Chem.* 58:2508–2523 (1980) Publication month not provided.

Duan et al., "Solvent Optimization of Reversed Phase High Performance Liquid Chromatographic Separation by Orthogonal Design," *Zhongguo Yaoke Daxue Xuebao* 18:126–129 (1987) Publication month not provided.

Ernest et al., "119. 2–Oxocephems and 2–Acetylpenems – Selective Formation in an Intramoleclar Witting Reaction," *Helvetica Chimica Acta* 64:1303–1311 (1981) Publication month not provided.

Farina et al., "A General Route to 3'Functionalized 3–Nor-cephalosporins," *J. Org. Chem.* 54:4962–4966 (1989) Publication month not provided.

Fetter and Lempert, "Simple and Condensed β–Lacatams. Part 8 –The Perparation and Reactions of Some 4–Oxo–azetidin–2–ylacetic Acid Derivatives, and a Synthesis of p–Nitrobenzyl (5RS, 6SR)–2–(2–Formylamino–ethylthio)–6–(2–methyl–1, 3–dioxolan–2–yl) carbapen–2–em–3–carboxylate, a Compound Related to the Antibiotic Thienamycin," *J. Chem. Research*, pp. 0349–0367 (1987) Publication month not provided.

(List continued on next page.)

*Primary Examiner*—Philip I. Datlow
*Assistant Examiner*—King Lit Wong
*Attorney, Agent, or Firm*—Lyon & Lyon

[57] ABSTRACT

The present invention includes novel (7R)-7-(acylamino)-3-(arylthio)-3-cephem-4-carboxylic acids or their pharmacologically acceptable salts which exhibit antibiotic activity against a wide spectrum of organisms including organisms which are resistant to β-lactam antibiotics and are useful as antibacterial agents. The invention also relates to novel intermediates useful for making the novel compounds of the present invention and to novel methods for producing the novel compounds and intermediate compounds.

15 Claims, No Drawings

OTHER PUBLICATIONS

Firestone and Christensen, "Functionalization of Penicillins at Carbon 6 via N–Acylimines. 6–Hydroxypenicillin. Substituted Penicillins and Cephalosporins. VIII," *J. Org. Chem.* 38:1436–1437 (1973) Publication month not provided.

Hamashima et al., "Synthetic Studies on β–Lacatm Antibiotics. 19. Synthesis of 3–Nor–Type 1–Oxacephems," *Tetrahedron Lett.* 51:4947–4950 (1979) Publication month not provided.

Hatanaka and Ishimaru, "A Simple Synthesis of (±)–1–Carbacephem Derivaties," *Tetrahedron Lett.* 24:4837–4838 (1983) Publication month not provided.

Kamachi et al., "Direct Introduction of a Formamido Group into the 7α(6α)–Position of Cephalosporins (Penicillins)," *J. Antibiotics* pp. 820–829 (1990) Publication month not provided.

Kang, H. Y., "Synthesis and Biological Evaluation of New Aminothiazolyl Cephalosporins with Elongated Side Chains," *Bull. Korean Chem. Soc.* 12:666–673 (1991) Publication month not provided.

Kondo et al., "New 2'–Amino Derivatives of Arbekacin, Potent Aminoglycoside Antibiotics Against Methicillin–Resisant," *J. Antibiotics* 46:531–534 (1993) Publication month not provided.

Lunn and Mason, "The Synthesis of 7α–Methoxy–7β–Amidocephalosporanic Acids by Methoxylation of 7β–(p–Nitrobenzyloxycarboxamido) Cephalosporanic Acid," *Tetrahedron Lett.* 14:1311–1313 (1974) Publication month not provided.

McCombie et al., "Synthesis of 3–Heterosubstituted Isocephem and Iso–Oxacephem Antibiotics," *Tetrahedron Lett.* 27:305–308 (1986) Publication month not provided.

Melillo et al., "A Practical Synthesis of (±)–Thienamycin," *Tetrahedron Lett.* 21:2783–2786 (1980) Publication month not provided.

Mochida et al., "Synthesis and Antibacterial Activity of Nvoel 3–Substituted Carbacephems," *J. Antibitoics* vol. XLII pp. 283–292 (1989) Publication month not provided.

Oh and Cho, "Studies on the Synthesis and Antibacterial Activity of New Zwitterionic Carbapenems," *J. Antibiotics* 47:126–128 (1994) Publication month not provided.

Ohki et al., "FK037. A New Parenteral Cephalosporins With a Boraid Antibacterial Spectrum: Synthesis and Antibacterial Activity," *J. Antibiotics* 46:359–361 (1993) Publication month not provided.

Oida et al., "2–(Alkylthio)penem–3–carboxylic Acids. I. Synthesis of 6–Unsubstituted Penems)," *Chem. Pharm. Bull.* 28:3232–3243 (1980) Publication month not provided.

Phillips and O'Neill, "A Convergent Process to C–2 Substituted Penems via Addition of Thiois and Organocuprates to an O–Triflylthloketene Acetal," *Tetrahedron Lett.* 23:3291–3294 (1990) Publication month not provided.

Ponsford and Southgate, "Preparation of 8–Oxo–7–(1–hydroxyethyl)–3–oxa–1–azabicyclo[4.2.0]octane Derivatives: Intermediates for Thienamycin Synthesis," *J.C.S. Chem. Comm.* 19:846–847 (1979) Publication month not provided.

Sanders et al., "Microbiological Characterization of Everninomicins B and D," *Antimicro. Agents Chemother.* 6:232–238 (1974) Publication month not provided.

Shih et al., "Synthetic Carbapenem Antibotics 1. 1–β–Methylcarbapenem," *Heterocycles* 21:29–40 (1984) Publication month not provided.

Shibata and Sugtimura, "Synthetic Studies of 1–β–Methylcarbapenem Antibiotics," *J. Antibiotics* 42:374–381 (1989) Publication month not provided.

Spangler et al., "Susceptibilities of Penicillin–Susceptible and –Resistant Strains of *Streptococcus pneumoniae* to RP 59500, Vancomycin, Erthromycin, PD 131628, Sparfloxacin, Temafloxacin, Win 57273, Ofloxacin, and Ciprofloxacin," *Antimicro. Agents Chemother.* 36:856–859 (1992) Publication month not provided.

Sum et al., "Glycylcycines. 1. A New Generation of Potent Antibacterial Agents through Modification of 9–Aminotetracyclines," *J. Med. Chem.* 37:184–188 (1994) Publication month not provided.

Sunagawa et al. "Synthesis and Biological Properties of 1β–Methyl–Carbapenems with N–Methylpyrrolidinylthio Group at C–2 Position," *J. Antibiotics* 45:971–976 (1992) Publication month not provided.

Sungawa et al., "New Penem Compounds with 5'–Substituted Pyrrolidinylthio Group as a C–2 Side Chain; Comparsion of their Biological Properties with Those of Carbapenem Compounds," *J. Antibiotics* 45:500–504 (1992) Publication month not provided.

Ternansky et al., "Discovery and Structure–Activity Relationship of a Series of 1–Carba–1–dethiacephems Exhibiting Activity against Methicillin–Resistant *Staphylococcus aureus*," *J. Med. Chem.* 36:1971–1976 (1971) Publication month not provided.

Tsubouchi et al., "A Convenient One Pot Asymmetric Synthesis of cis–β–Lactams: Key Precursors for Optically Active 2–Oxaisocephems," *Tetrahedron Assymetry* 5:441–452 (1994) Publication month not provided.

Tsuchiya, "Cefsulodin (SCE–129), Cefotiam (SCE–963), and Cefmenoxime (SCE–1365)," *Beta–Lactam Antibiot.* pp. 107–119 (1981) Publication month not provided.

Yokoo et al., "Studies on Cephalosporin Antibiotics," *J. Antibiotics* 44:498–506 (1991) Publication month not provided.

Yoshida et al., "An Efficient Carbapenem Synthesis via an Intramolecular Witting Reaction of New Trialkoxphosphorane–Thiolesters," *Tetrahedron Lett.* 25:2793–2796 (1984) Publication month not provided.

Yoshida et al., "New Synthesis of Penems via Reductive Cyclization Reaction of Oxalimides with Trialkyl Phosphite," *Chem. Pharm. Bull.* 31:768–771 (1983) Publication month not provided.

Yoshioka et al., "Stereocontrolled, Straightforward Synthesis of 3–Substituted Methyl 7α–Methoxy–1–Oxacephems," *Tetrahedron Lett.* 21:351–354 (1980) Publication month not provided.

CEPHALOSPORIN ANTIBIOTICS

1. RELATED APPLICATIONS

The present application is a continuation-in-part of U.S. application Ser. No. 08/369,798, filed Jan. 6, 1995 which is a continuation-in-part application of U.S. application, Ser. No.08/222,262, filed Apr. 1, 1994 and now abandoned, both of which are incorporated herein by reference in their entirety, including any drawings.

BACKGROUND OF THE INVENTION

1. Field of the Invention

The present invention relates to cephalosporin antibiotics. More particularly, the present invention includes novel (7R)-7-(acylamino)-3-(arylthio)-3-cephem-4-carboxylic acids and their pharmacologically acceptable salts and prodrugs, their methods of production and use. These compounds exhibit antibiotic activity against a wide spectrum of organisms, including organisms which are resistant to β-lactam antibiotics.

2. Review of the Background Art

Over the past three decades a large variety of antibiotics has become available for clinical use. One class of antibiotics which has seen remarkable growth are the cephalosporins (shown generically below), over 70 of which have entered clinical use for the treatment of bacterial infections in mammals since 1965. The cephalosporins exhibit their antibacterial activity by inhibiting bacterial peptidoglycan biosynthesis, and have been extremely effective in treating a wide variety of bacterial infections. Cephalosporins that are said to have antibacterial activity are described in U.S. Pat. No. 3,992,377 and U.S. Pat. No. 4,256,739.

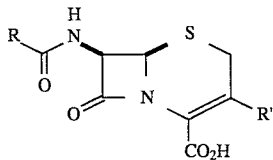

I

Unfortunately, the wide-spread and indiscriminant use of these antibiotics has led to a rapid increase in the number of bacterial strains which are resistant to these compounds. Most importantly, this resistance has emerged among clinically important microorganisms which threaten to limit the utility of presently available cephalosporin antibiotics. In particular, resistant strains of Salmonella, *S. pneumoniae*, Enterobacteriaceae, and Pseudomonas have emerged which threaten to undo many of the strides made in reducing mortality and morbidity from bacterial infections.

Bacterial resistance to cephalosporins follows three major pathways: a) the development of β-lactamases capable of inactivating the β-lactam ring of the cephalosporin; b) decreased cephalosporin penetration into the bacteria due to changes in bacterial cell wall composition; and c) poor binding to penicillin-binding proteins (PBPs). The latter pathway is especially important, as the binding of β-lactams to PBPs is essential for inhibiting bacterial cellwall biosynthesis. Certain Gram-positive bacteria, namely methicillin-resistant *Staphylococcus aureus* ("MRSA") and enterococci are highly resistant to β-lactam antibiotics. Resistance in MRSA is due to the presence of high levels of an unusual PBP, PBP2a, which is insensitive, or binds poorly, to β-lactam antibiotics. The activity of β-lactam antibiotics against PBP2a-containing organisms has been shown to correlate well with the binding affinity of the antibiotic to PBP2a. Currently, the glycopeptides vancomycin and teicoplanin are primarily used for MRSA bacteria. The quinolone antibacterials and some carbapenems, such as imipenem, have been reported to be active against a few MRSA strains, but their use is restricted due to emerging resistant MRSA strains.

Experimental compounds which may possess utility as anti-MRSA or anti-enterococcal bactericides include the glycylcyclines (See, e.g., P.-E. Sum et al., *J. Med. Chem.*, 37, (1994)), FK-037 (see, e.g., H. Ohki et al., *J. Antibiotics*, 46:359∝361 (1993)), RP-59,500 (see, e.g., S. K. Spangler et al., *Antimicro. Agents Chemother.*, 36:856–9 (1992)), the everninomycin complex (see, e.g., W. E. Sanders et al., *Antimicro. Agents Chemother*, 6:232–8 (1974)), the 2-(biaryl)carbapenems (see, e.g., U.S. Pat. No. 5,025,006), 3-(benzothiazolylthio)cephems (see, e.g., EP Application No. 527686), 3-(thiazolylthio)carbacephems (see, e.g., R. J. Ternansky et al., *J. Med. Chem.*, 36:1971 (1993) and U.S. Pat. No. 5,077,287) and arbekacin (S. Kondo, et al. *J. Antibiotics* 46:531 (1993).

SUMMARY OF THE INVENTION

The present invention includes compounds, compositions and methods effective to treat infections in mammals arising from β-lactam antibiotic resistant bacteria.

In one aspect the present invention features a (7R)-7(acylamino)-3-(arylthio)-3-cephem-4-carboxylic acid cephalosporin antibiotic and has antibiotic activity against an organism resistant to a beta-lactam antibiotic. Examples of particular classes of compounds having such activity are described below and data is presented showing the in vitro and in vivo effectiveness of such compounds. Such compounds have a minimum inhibitory concentration (MIC) that is less that 50%, more preferably less than 10%, and most preferably less than 1% of the MIC of the Cefotaxime for a beta-lactam resistant organism, such as those listed in Table 1, preferably a beta-lactam resistant Staphylococcal or Enterococcal organism. Other preferred compounds are able to prevent or reduce mortality in mice infected with the betalactam resistant organism to a greater extent that vancomycin or Cefotaxime.

In one embodiment, the present invention includes cephalosporin compounds as shown in Structure II:

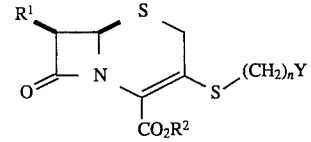

II and their pharmaceutically acceptable salts and prodrugs, wherein $R^1$ is —NHC(O)ZR$^3$ or —NR$^4$R$^5$, where Z is —CH$_2$(X)$_m$—, —C(NOR$^6$)—, —CH(OR$^7$)—, —C(CHCO$_2$R$^8$)—or —CH(NR$^9$R$^{10}$)—, X is O or S, and m is 0 or 1;

or $R^1$ is

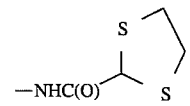

$R^2$ is hydrogen, alkyl, alkenyl, aryl, heterocycle, aralkyl, heteroaralkyl, or trialkylsilyl;

$R^3$ may be cyano, alkyl, aryl, heterocycle and heteroaralkyl;

$R^{4-7}$ may be independently hydrogen, alkyl, aryl and acyl;

$R^8$ may be selected from the group of hydrogen, alkyl and aryl;

$R^9$ and $R^{10}$ are selected independently from the group consisting of hydrogen, alkyl, acyl, and heterocyclecarbonyl;

n is 0 or 1; and

Y is selected from the group consisting of aryl and heterotricycle.

However, when n is 0 and $R^1$ is selected from the group consisting of phenylacetamido, phenylthioacetamido, phenyloxyacetamido, D-α-aminophenylacetamido, thienylacetamido and D-mandeloylamido, Y is not phenyl substituted with $C_1$-$C_4$ alkyl, $C_1$-$C_4$ alkoxyl or halogen, other than 2-bromo or 2-iodo. Also, when n is 1, Y is not phenyl when $R^3$ is 4-(2-amino)thiazolyl and Z is —C(NOCH$_2$CO$_2$H)—.

Preferred compounds include those compounds wherein $R^3$ is phenyl, $R^2$ is hydrogen, n is 0 and Y is 2-iodo- or 2-bromo-substituted phenyl. Another preferred embodiment is one wherein $R^3$, $R^2$ and n are as just described and Y is dibenzfuranyl. Another preferred compound is one wherein Y is 2-biphenyl.

In other embodiments, the compounds described above contain the following substituents on the phenyl group: ortho-cyano; thienyl (and substituted thienyl), hydroxymethyl, trifluoromethyl, methylthio, substituted-furanyl, nitro, and formyl. In other preferred embodiments the compounds described above contain the ring structures exemplified by compounds 54–57 listed herein.

In another embodiment, the present invention provides for compositions comprising an amount of the compound of Structure II effective to treat bacterial infections in mammals arising from bacteria resistant to β-lactam antibiotics.

In still another embodiment, the present invention includes methods for treating a bacterial infection in a mammal arising from bacteria resistant to β-lactam antibiotics comprising administering to a mammal suffering from such an infection a therapeutically effective amount of a compound of Structure II.

In another aspect the invention features compounds of the structure:

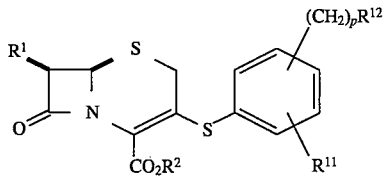

III and their pharmaceutically acceptable salts and prodrugs, wherein $R^1$ is —NHC(O)Z$R^3$ or —NR$^4$R$^5$, where Z is —CH$_2$(X)$_m$—, —C(NOR$^6$)—, —CH(OR$^7$)—, —C(CHCO$_2$R$^8$)— or —CH(NR$^9$R$^{10}$)—, X is O or S, and m is 0 or 1;

or $R^1$ is

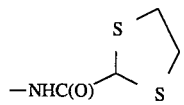

$R^2$ is hydrogen, alkyl, alkenyl, aryl, heterocycle, aralkyl, heteroaralkyl, or trialkylsilyl;

$R^3$ may be cyano, alkyl, aryl, heterocycle and heteroaralkyl;

$R^{4-7}$ may be independently hydrogen, alkyl, aryl and acyl;

$R^8$ may be selected from the group of hydrogen, alkyl and aryl;

$R^9$ and $R^{10}$ are selected independently from the group consisting of hydrogen, alkyl, acyl, and heterocyclecarbonyl;

$R^{11}$ is H or halogen;

$R^{12}$ is

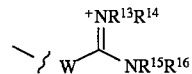

where W=S, NH, or CH$_2$ and $R^{13}$–$R^{16}$ are H, alkyl, cycloalkyl, acyl, hydroxy, amino, amidino, or phosphoryl and taken together may form a 5- or 6-membered ring or $R^{12}$ is S-$R^{17}$ where $R^{17}$ is alkyl, cycloalkyl, or a 5- or 6-membered ring heterocycle containing 0–4 nitrogen atoms, 0–1 oxygen atoms, and 0–1 sulfur atoms, and which is optionally substituted by alkyl, hydroxyl, alkoxyl, amino, hydroxymethyl, aminomethyl, or mono- or dialkylaminomethyl;

and p is 0, 1 or 2.

Preferred compounds include those compounds wherein $R^{11}$ is H or halogen, $R^{12}$ is

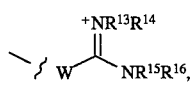

W=S, NH, or CH$_2$, p is 0, 1 or 2, and $R^{13}$–$R^{16}$ are H or lower alkyl. Especially preferred compounds include those compounds wherein $R^{11}$ is hydrogen, $R^{12}$ is

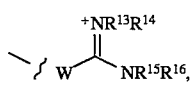

W=S, or NH, p is 1, and $R^{13}$–$R^{16}$ are hydrogen.

In another embodiment, the present invention provides for compositions comprising an amount of the compound of Structure 3 effective to treat bacterial infections in mammals arising from bacteria resistant to β-lactam antibiotics.

In still another embodiment, the present invention includes methods for treating a bacterial infection in a mammal arising from bacteria resistant to β-lactam antibiotics comprising administering to a mammal suffering from such an infection a therapeutically effective amount of a compound of Structure III.

In another aspect the invention features compounds of the structures

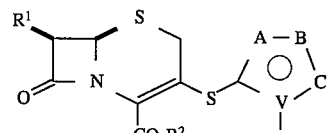

IV

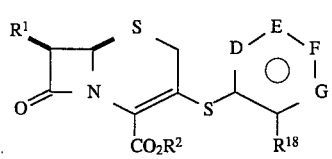

V and their pharmaceutically acceptable salts and prodrugs, wherein $R^1$ is —NHC(O)Z$R^3$ or —NR$^4$R$^5$, where Z is —CH$_2$(X)$_m$—, —C(NOR$^6$)—, —CH(OR$^7$)—, —C(CHCO$_2$R$^8$)— or —CH(NR$^9$R$^{10}$)—, X is O or S, and m is 0 or 1;

or R$^1$ is

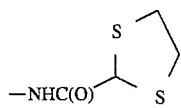

R$^2$ is hydrogen, alkyl, alkenyl, aryl, heterocycle, aralkyl, heteroaralkyl, or trialkylsilyl;

R$^3$ may be cyano, alkyl, aryl, heterocycle and heteroaralkyl;

R$^{4-7}$ may be independently hydrogen, alkyl, aryl and acyl;

R$^8$ may be selected from the group of hydrogen, alkyl and aryl;

R$^9$ and R$^{10}$ are selected independently from the group consisting of hydrogen, alkyl, acyl, and heterocyclecarbonyl;

R$^{18}$ is optionally substituted phenyl or heteroaryl, or cyano;

V=C or N

A–C are CR$^{19}$, N or S, where R$^{19}$ is hydrogen, alkyl, hydroxyl, amino, cyano, hydroxymethyl, or mono- or dialkylaminomethyl D–G are CR$^{19}$ or N, where R$^{19}$ is hydrogen, alkyl, hydroxyl, amino, cyano, hydroxymethyl, or mono- or dialkylaminomethyl. The specific juxtaposition of groups A–C and D–G is limited to examples of heterocyclic groups known in the chemistry arts. Specific examples of these heterocyclic groups include the following:

Preferred compounds include those compounds wherein the groups A–C, V and D–G are pyrazole, thiadiazole and pyridine, and R$^{18}$ is optionally-substituted phenyl, pyridyl, pyrazolyl, or cyano.

In another embodiment, the present invention provides for compositions comprising an amount of the compound of Structure IV effective to treat bacterial infections in mammals arising from bacteria resistant to β-lactam antibiotics.

In still another embodiment, the present invention includes methods for treating a bacterial infection in a mammal arising from bacteria resistant to β-lactam antibiotics comprising administering to a mammal suffering from such an infection a therapeutically effective amount of a compound of Structure IV.

Other features and advantages of the invention will be apparent from the following description of the preferred embodiments thereof and from the claims.

DESCRIPTION OF THE PREFERRED EMBODIMENTS

I. Definitions

As used herein, the term "alkyl" denotes branched or unbranched hydrocarbon chains containing between one and six, preferably one and four, carbon atoms, such as, e.g., methyl, ethyl, n-propyl, iso-propyl, n-butyl, sec-butyl, iso-butyl, tert-butyl, and 2-methylpentyl. These groups may be optionally substituted with one or more functional groups which are attached commonly to such chains, such as, e.g., hydroxyl, bromo, fluoro, chloro, iodo, mercapto or thio, cyano, alkylthio, heterocycle, aryl, heteroaryl, carboxyl, alkoxycarbonyl, alkyl, alkenyl, nitro, amino, alkoxyl, amido, and optionally substituted isothioureido, amidino, guanidino, and the like to form alkyl groups such as trifluoromethyl, 3-hydroxyhexyl, 2-carboxypropyl, 2-fluoroethyl, carboxymethyl, 4-cyanobutyl, 2-guanidinoethyl, 3-N,N'-dimethylisothiouroniumpropyl, and the like.

The term "alkenyl" denotes an alkyl group as defined above having at least one double bond, e.g., allyl, 3-hydroxy-2-buten-1-yl, 1-methyl-2-propen-1-yl and the like.

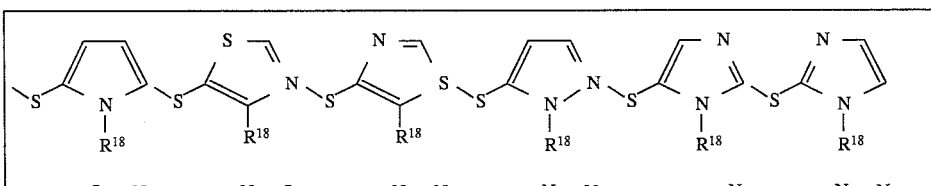

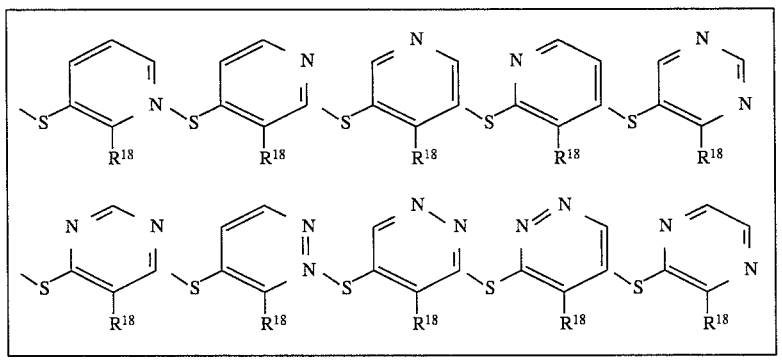

The term "aryl" denotes a chain of carbon atoms an which form an least one aromatic ring having preferably between about 6–14 carbon atoms, such as, e.g., phenyl, naphthyl, indenyl, and the like, and which may be substituted with one or more functional groups which are attached commonly to such chains, such as, e.g., hydroxyl, bromo, fluoro, chloro, iodo, mercapto or thio, cyano, cyanoamido, alkylthio, heterocycle, aryl, heteroaryl, carboxyl, alkoxycarbonyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, cyanophenyl, pyridylphenyl, pyrrolylphenyl, pyrazolylphenyl, triazolylphenyl, tetrazolylphenyl and the like.

The term "heterocycle" denotes a chain of carbon and at least one non-carbon atoms which together form one or more aromatic or non-aromatic rings having preferably between about 6–14 atoms, such as, e.g., furyl, thienyl, imidazolyl, indolyl, pyridinyl, thiadiazolyl, thiazolyl, piperazinyl, dibenzfuranyl, dibenzthienyl. These rings may be optionally substituted with one or more functional groups which are attached commonly to such rings, such as, e.g., hydroxyl, bromo, fluoro, chloro, iodo, mercapto or thio, cyano, cyanoamido, alkylthio, heterocycle, aryl, heteroaryl, carboxyl, oxo, alkoxycarbonyl, alkyl, alkenyl, nitro, amino, alkoxyl, amido, and the like to form rings such as, e.g., 2-aminothiazol-4-yl, 2,3-dioxopiperazinyl, 4-alkylpiperazinyl, 2-iodo-3-dibenzfuranyl and 3-hydroxy-4-dibenzthienyl and the like.

The term "heteroaromatic" or "heteroaryl" (HetAr) denotes an aromatic heterocycle as defined above.

The term "heterotricycle" denotes an aromatic heterocyclic substituent as defined above which comprises three aromatic rings.

The term "heterocyclecarbonyl" denotes the group C(O)Het, where Het is heterocycle as defined above.

The term "alkoxyl" denotes the group —OR, where R is alkyl as defined above, such as methoxy, ethoxy, n-propoxy, iso-propoxy, n-butoxy, sec-butoxy, iso-butoxy, tert-butoxy, trifluoromethoxy, 3-hydroxyhexyloxy, 2-carboxypropyloxy, 2-fluoroethoxy, carboxymethoxy and cyanobutyloxy and the like.

The term "alkylthio" denotes the group —SR, where R is alkyl as defined above, such as methylthio, ethylthio, n-propylthio, iso-propylthio, n-butylthio, sec-butylthio, isobutylthio, tert-butylthio, trifluoromethylthio, 3-hydroxyhexylthio, 2-carboxypropylthio, 2-fluoroethylthio, carboxymethylthio and cyanobutylthio and the like.

The term "acyl" denotes groups —C(O)R, where R is alkyl as defined above, such as formyl, acetyl, propionyl, or butyryl.

The term "aryloxy" denotes groups -OAr, where Ar is an aryl group as defined above.

The term "aralkyl" denotes groups -RAr, where R is alkyl and Ar is aryl, both as defined above.

The term "heteroaralkyl" denotes groups —RHetAr where R is alkyl and HetAr is heteroaryl as defined above.

The term "trialkylsilyl" denotes the group RR'R"Si—, where R, R' and R" are alkyl as defined above.

The term "trialkylammonium" denotes the group [RR'R"N-]$^+$, where R, R' and R" are alkyl as defined above The term "amino" denotes the group NRR', where R and R' may independently be alkyl, aryl or acyl as defined above, or hydrogen.

The term "amido" denotes the group —C(O)NRR', where R and R' may independently be alkyl, aryl or acyl as defined above, or hydrogen.

The term "cyanoamido" refers to the group —NH—C≡N.

The term "β-lactam resistant bacteria" refers to bacteria against which a β-lactam antibiotic has an minimum inhibitory concentration (MIC) greater than 32 mg/ml. The term "prodrug" refers to an agent that is converted into the parent drug in vivo. Prodrugs may be easier to administer than the parent drug in some situations. For example, the prodrug may be bioavailable by oral administration but the parent is not, or the prodrug may improve solubility to allow for intravenous administration.

II. Compounds of the Invention

The present invention provides compounds, methods and compositions effective to treat bacterial infections, and, especially, infections arising from bacteria which have developed resistance to conventional β-lactam antibiotics. More importantly, the present invention provides compounds, methods and compositions effective to treat bacterial infections arising from bacteria which have developed resistance to conventional cephalosporin antibiotics.

A. Preferred Embodiments of Structure II

Preferred embodiments include those compounds wherein Y is aryl, and more particularly phenyl optionally substituted with acyl, alkyl, hydroxyl, halogen, carbonyl, thioalkyl, amido, alkoxyl, trialkylammonium, cyanoalkylamido, imidazolyl, thiazolyl, oxazolyl, imidazolylmethyl, thiazolylmethyl, oxazolylmethyl, imidazolium, imidazoliummethyl, thienyl, thienylmethyl, furyl, furylmethyl, pyridinium, cyano, pyridyl, pyrrolyl, pyrazolyl, triazolyl, and tetrazolyl. More preferred phenyl substituents are those where n is 0, and the substituent is located at the 2-position of the phenyl ring relative to the point of attachment of the sulfur atom linking the Y group to the cephem ring.

Another preferred substituent Y is one wherein Y is phenyl substituted with phenyl to form biphenyl. Still more preferred is biphenyl optionally substituted with acyl, alkyl, hydroxyl, halogen, trialkylammonium, imidazolyl, thiazolyl, oxazolyl, imidazolylmethyl, thiazolylmethyl, oxazolylmethyl, imidazolium, imidazoliummethyl, thienyl, thienylmethyl, furyl, furylmethyl or pyridinium. Preferred substituents are halogen, especially bromo, chloro and iodo. Again, substituents at the 2-position of the biphenyl ring relative to the position of attachment of the biphenyl moiety to the remainder of the cephalosporin molecule. Especially preferred biphenyl substituents are 2-iodo-4-biphenyl, 2-bromo-4-biphenyl and 2-chloro-4-biphenyl. Also preferred are 4-substituted 2-biphenyls, e.g., 4-iodo-2-biphenyl, 4-bromo-2-biphenyl and 4-chloro-2-biphenyl.

Still another preferred substituent Y is one wherein Y is heteroaryl, especially dibenzfuranyl or dibenzthienyl, each optionally substituted with acyl, alkyl, hydroxyl, halogen, trialkylammonium, imidazolyl, thiazolyl, oxazolyl, imidazolylmethyl, thiazolylmethyl, oxazolylmethyl, imidazolium, imidazoliummethyl, thienyl, thienylmethyl, furyl, furylmethyl or pyridinium. dibenzfuranyl and dibenzthienyl are especially preferred.

With respect to $R^3$, especially preferred embodiments are those wherein $R^3$ is cyano, alkyl, aryl, heterocycle or heteroaralkyl. Other preferred embodiments include those wherein $R^3$ is hydroxyphenyl, preferably 4-hydroxyphenyl, heterocycle and heteroaralkyl. Preferred heterocycle substituents include thienyl, furyl and thiazolyl, especially 2-thienyl, 2-furyl, and optionally substituted heterocycles such as 2-aminothiazol-4-yl.

Especially preferred compounds combining the above-described substituents include the following:

(7R)-7-[(phenylacetyl)amino]-3-(4-biphenylmethylthio)-3-cephem-4-carboxylic acid
(7R)-7-[(phenylacetyl)amino]-3-(m-iodophenylthio)-3-cephem-4-carboxylic acid
(7R)-7-[(phenylacetyl)amino]-3-(p-chlorophenylthio)-3-cephem-4-carboxylic acid
(7R)-7-[(phenylacetyl)amino]-3-(o-bromophenylthio)-3-cephem-4-carboxylic acid
(7R)-7-[(phenylacetyl)amino]-3-(p-bromophenylthio)-3-cephem-4-carboxylic acid
(7R)-7-[(phenylacetyl)amino]-3-(o-iodophenylthio)-3-cephem-4-carboxylic acid
(7R)-7-[(phenylacetyl)amino]-3-(o-dibenzofuranyl)-thio)-3-cephem-4-carboxylic acid
(7R)-7-[(phenylacetyl)amino]-3-(4-biphenylthio)-3-cephem-4-carboxylic acid
(7R)-7-[(phenylacetyl)amino]-3-(2-biphenylthio)-3-cephem-4-carboxylic acid
(7R)-7-[(phenylacetyl)amino]-3-(3-biphenylthio)-3-cephem-4-carboxylic acid
(7R)-7-[(phenylacetyl)amino]-3-(2-bromo-4-biphenylthio)-3-cephem-4-carboxylic acid
(7R)-7-[(phenylacetyl)amino]-3-(2-fluoro-4-biphenylthio)-3-cephem-4-carboxylic acid
(7R)-7-[(phenylacetyl)amino]-3-(4-bromo-2-biphenylthio)-3-cephem-4-carboxylic acid
(7R)-7-[(phenylacetyl)amino]-3-(-o-chlorophenylthio)-3-cephem-4-carboxylic acid
(7R)-7-[(phenylacetyl)amino]-3-(2,5-dichlorophenylthio)-3-cephem-4-carboxylic acid
(7R)-7-[(Cyanoacetyl)amino]-3-(o-iodophenylthio)-3-cephem-4-carboxylic acid
(7R)-7-[(phenylacetyl)amino]-3-(3,4-dichlorophenylthio)-3-cephem-4-carboxylic acid
(7R)-7-[(phenylacetyl)amino]-3-(o-carbomethoxyphenylthio)-3-cephem-4-carboxylic acid
(7R)-7-[(2-Thienylacetyl)amino]-3-(o-bromophenylthio)-3-cephem-4-carboxylic acid
(7R)-7-[(phenylacetyl)amino]-3-(dibenzofuranyl-1-thio)-3-cephem-4-carboxylic acid
(7R)-7-[(Z)-(2-aminothiazol-4-yl)-2-(synhydroxyimino)acetamido]-3-(o-iodophenylthio)-3-cephem-4-carboxylic acid
(7R)-7-[(phenylacetyl)amino]-3-(2-(4-cyanophenyl)phenylthio )-3-cephem-4-carboxylic acid
(7R)-7-[(phenylacetyl)amino]-3-(2,3-dichlorophenylthio)-3-cephem-4-carboxylic acid
(7R)-7-[(2-Thienylacetyl)amino]-3-(o-iodophenylthio)-3-cephem-4-carboxylic acid
(7R)-7-[(2-Thienylacetyl)amino]-3-(2,5-dichlorophenylthio)-3-cephem-4-carboxylic acid
(7R)-7-[(phenylacetyl)amino]-3-(2-(2-furyl)phenylthio)-3-cephem-4-carboxylic acid
(7R)-7-[(phenylacetyl)amino]-3-(2,4 -dichlorophenylthio )-3-cephem-4 -carboxylic acid
(7R)-7-[(p-Methoxyphenylacetyl)amino]-3-(o-iodophenylthio )-3-cephem-4-carboxylic acid
(7R)-7-[(p-Chlorophenoxyacetyl)amino]-3-(o-iodophenylthio )-3-cephem-4-carboxylic acid
(7R)-7-[(p-Chlorophenoxyacetyl)amino]-3-(2,5-dichlorophenylthio )-3-cephem-4-carboxylic acid
(7R)-7-[(p-Methoxyphenylacetyl)amino]-3-(2,5-dichlorophenylthio)-3-cephem-4-carboxylic acid
(7R)-7-[(phenylacetyl)amino]-3-(2-bromo-5-fluorophenylthio)-3-cephem-4-carboxylic acid.

With respect to Z, preferred embodiments include those wherein Z is methylene, substituted oxyiminomethylene (—C(NOR)—), substituted oxymethylene (—CH(OR)—), substituted (carboxymethylene)methylene (—C(CHCO$_2$R)—), and aminomethylene (—CH(NRR')—). Preferred substituents for Z=oxyiminomethylene, oxymethylene and (carboxymethylene)methylene include hydrogen, alkyl, aryl and heterocycle. Such groups include, e.g., hydrogen, 2-fluoroethyl, cyclopropylmethyl, cyclopentyl, allyl, and dichloroallyl. Preferred substituents for Z=aminomethylene include alkyl, aryl, and heterocycle and acyl.

In another preferred embodiment, the present invention includes intermediates which are especially useful in the formation of the bactericides of the invention. Generally these intermediates include those embodiments of the invention wherein $R^1$ is —NRR', where R and R' are hydrogen, and acyl. Examples of such groups include, e.g., t-butyloxycarbonyl and benzyloxycarbonyl.

Finally, $R^2$ may be selected from the group hydrogen, alkyl, alkenyl, aryl, heterocycle, aralkyl, heteroaralkyl, alkoxyl, or trialkylsilyl. Generally, only those compounds with $R^2$=hydrogen are biologically active. However, the present invention also contemplates other $R^2$ substituents which are either easily hydrolyzed under biological conditions, i.e., such groups which can be cleaved easily after injection or ingestion of a compound of the invention by a mammalian subject (see, e.g., European Patent Application No. 527,686 A1 to Tsushima, et al., which is incorporated herein by reference). The present invention further contemplates substituents $R^2$ which are effective to protect the carboxyl group from unwanted reactions during synthesis of the compounds of the invention. Many such protective groups are well-known in the art (see, e.g., Green and Wuts, PROTECTIVE GROUPS IN ORGANIC SYNTHESIS (Wiley 1991), which is incorporated herein by reference). Examples of such groups include allyl, t-amyl, benzhydryl, t-butyl, t-butyldimethylsilyl, benzyl, 2-chloroallyl, 3,3-dimethylallyl, 2,4-dimethoxybenzyl, 3,4-dimethoxybenzyl, 4,4'-dimethoxytrityl, 4-methoxybenzyl, 2-methoxybenzyl, 4-methoxytrityl, methoxymethyl, 4-nitrobenzyl, 2-nitrobenzyl, phenacyl, 2,2,2-trichloroethyl, trimethylsilyl, 2-(trimethylsilyl)ethyl, and trityl as well as the trifluoroacetate, hydrochloride, hydrobromide and sulfate salts thereof.

B. Preferred Embodiments of Structure III

In another aspect the invention features compounds of the structure:

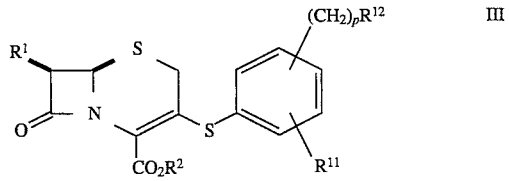

and their pharmaceutically acceptable salts and prodrugs, wherein
$R^1$ is —NHC(O)ZR$^3$ or —NR$^4$R$^5$, where Z is —CH$_2$(X)$_m$—, —C(NOR$^6$)—, —CH(OR$^7$)—, —C(CHCO$_2$R$^8$)—or —CH(NR$^9$R$^{10}$)—, X is O or S, and m is 0 or 1;

or R¹ is

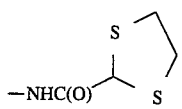

R² is hydrogen, alkyl, alkenyl, aryl, heterocycle, aralkyl, heteroaralkyl, or trialkylsilyl;

R³ may be cyano, alkyl, aryl, heterocycle and heteroaralkyl;

R⁴⁻⁷ may be independently hydrogen, alkyl, aryl and acyl;

R⁸ may be selected from the group of hydrogen, alkyl and aryl;

R⁹ and R¹⁰ are selected independently from the group consisting of hydrogen, alkyl, acyl, and heterocyclecarbonyl;

p=1 or 2;

R¹¹ is H or halogen;

R¹² is

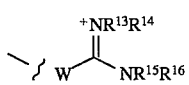

where W=S, NH, or CH₂ and R¹³-R¹⁶ are H, hydroxy, amido, aminidino, alkyl, cycloalkyl, acyl, or phosphoryl and taken together may form a 5- or 6-membered ring or R¹² is S-R¹⁷ where R¹⁷ is alkyl, cycloalkyl, or a 5- or 6-membered ring heterocycle containing 0–4 nitrogen atoms, 0–1 oxygen atoms, and 0–1 sulfur atoms, and which is optionally substituted by alkyl, hydroxyl, alkoxyl, amino, hydroxymethyl, aminomethyl, or mono- or dialkylaminomethyl.

Preferred compounds include those compounds wherein R¹¹ is H or halogen, R¹² is

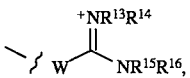

W=S, NH, or CH₂, p is 0, 1 or 2, and R¹³-R¹⁶ are H or lower alkyl. Especially preferred compounds include those compounds wherein R¹¹ is hydrogen, R¹² is

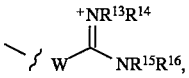

W=S, or NH, p is 1, and R¹³-R¹⁶ are hydrogen.

Especially preferred compounds combining the above-described substituents include the following:

(7R)-7-[(Phenylacetyl)amino]-3-(2-isothiouroniummethylphenylthio)-3-cephem-4-carboxylate, inner salt (7R)-7-[((4-isothiouroniummethylphenyl)acetyl)amino]-3-(2-isothiouroniummethylphenylthio)-3-cephem-4-carboxylate, trifluoroacetic acid salt (7R)-7-[((4-Hydroxyphenyl)acetyl)amino]-3-(2-isothiouroniummethylphenylthio)-3-cephem-4-carboxylic acid, inner salt (7R)-7-[(Phenylacetyl)amino]-3-(2-(2-isothiouronium)ethylphenylthio)-3-cephem-4-carboxylate, inner salt (7R)-7-[((2-Aminomethylphenyl)acetyl)amino]-3-(2-isothiouroniummethylphenylthio)-3-cephem-4-carboxylate, trifluoroacetic acid salt (7R)-7-[(Phenylacetyl)amino]-3-(2-tetramethylisothiouroniummethylphenylthio)-3-cephem-4-carboxylate, inner salt (7R)-7-[(Phenylacetyl)amino]-3-(2-N,N'-diethylisothiouroniummethylphenylthio)-3-cephem-4-carboxylate, inner salt (7R)-7-[(Phenylacetyl)amino]-3-(2-N-methylisothiouroniummethylphenylthio)-3-cephem-4-carboxylate, inner salt (7R)-7-[(Phenylacetyl)amino]-3-(2-N-cyclopropylisothiouroniummethylphenylthio)-3-cephem-4carboxylate, inner salt (7R)-7-[(Phenylacetyl)amino]-3-(3-isothiouroniummethylphenylthio)-3-cephem-4-carboxylate, inner salt (7R)-7-[((2-guanidinoethylthio)acetyl)amino]-3-(2-isothiouroniummethylphenylthio)-3-cephem-4-carboxylate, trifluoroacetic acid salt (7R)-7-[(Z)-2-(Aminothiazol-4-yl)-2-(hydroxyimino)acetamido]-3-(2-isothiouroniummethylphenylthio)-3-cephem-4-carboxylate, inner salt (7R)-7-[(Z)-2-(Phenyl)-2-(hydroxyimino)acetamido]-3-(2-isothiouroniummethylphenylthio)-3-cephem-4-carboxylate, inner salt (7R)-7-[(methylthioacetyl)amino]-3-(2-isothiouroniummethylphenylthio)-3-cephem-4-carboxylate, inner salt C. Preferred Embodiments of Structures IV and V In another aspect the invention features compounds of the structures

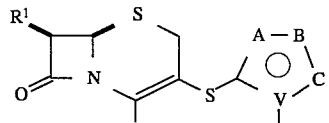

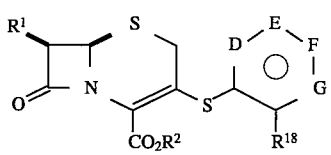

and their pharmaceutically acceptable salts and prodrugs, wherein

R¹ is —NHC(O)ZR³ or —NR⁴R⁵, where Z is —CH₂(X)ₘ—, —C(NOR⁶)—, —CH(OR⁷)—, —C(CHCO₂R⁸)— or —CH(NR⁹R¹⁰)—, X is O or S, and m is 0 or 1;

or R¹ is

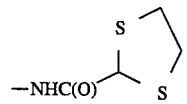

R² is hydrogen, alkyl, alkenyl, aryl, heterocycle, aralkyl, heteroaralkyl, or trialkylsilyl;

R³ may be cyano, alkyl, aryl, heterocycle and heteroaralkyl;

R⁴⁻⁷ may be independently hydrogen, alkyl, aryl and acyl;

R⁸ may be selected from the group of hydrogen, alkyl and aryl;

R⁹ and R¹⁰ are selected independently from the group consisting of hydrogen, alkyl, acyl, and heterocyclecarbonyl;

R¹⁸ is optionally substituted phenyl or heteroaryl, or cyano;

V=C or N

A–C are CR[19], N or S, where R[19] is hydrogen, alkyl, hydroxyl, amino, cyano, hydroxymethyl, or mono-or dialkylaminomethyl D–G are CR[19] or N, where R[19] is hydrogen, alkyl, hydroxyl, amino, cyano, hydroxymethyl, or mono-or dialkylaminomethyl. The specific juxtaposition of groups A–C and D–G is limited to examples of heterocyclic groups known in the chemistry arts.

Preferred compounds include those compounds wherein the groups A–C, V and D–G are pyrazole, thiadiazole and pyridine, and R[18] is optionally-substituted phenyl, pyridyl, pyrazolyl, or cyano.

Especially preferred compounds combining the above-described substituents include the following:

(7R)-7-[(Phenylacetyl)amino]-3-(1-N-phenylpyrazol-5-ylthio)-3-cephem-4-carboxylic acid
(7R)-7-[(4-Chlorophenylacetyl)amino]-3-(2-phenylpyridin-3-ylthio)-3-cephem-4-carboxylic
(7R)-7-[(Phenylacetyl)amino]-3-(1-N-phenyltetrazol-5-ylthio)-3-cephem-4-carboxylic acid
(7R)-7-[(Phenylacetyl)amino]-3-(2-oxazol-5-ylphenylthio)-3-cephem-4-carboxylic acid
(7R)-7-[(Phenylacetyl)amino]-3-(1-N-phenyl-1,2,3-triazol-5-ylthio)-3-cephem-4-carboxylic acid
(7R )-7-[(Cyanoacetyl)amino]-3-(1-N-phenylpyridin-5-ylthio)-3-cephem-4-carboxylic acid
(7R)-7-[(Phenylacetyl)amino]-3-(2-amino-4-phenyl-thiazol-5-ylthio)-3-cephem-4-carboxylic acid
(7R)-7-[(Cyanoacetyl)amino]-3-(2-phenylpyridin-3-ylthio)-3-cephem-4-carboxylic acid
(7R)-7-[(Phenylacetyl)amino]-3-(4-phenyl-1,2,3-thiadiazol-5-ylthio)-3-cephem-4-carboxylic acid
(7R)-7-[(Z)-2-(aminothiazol-4-yl)-2-(cyclopentyloxyimino)acetamido]-3-(1-N-phenylpyridin-5-ylthio)-3-cephem-4-carboxylic acid
(7R)-7-[(Z)-2-(aminothiazol-4-yl)-2-(2-fluoroethyloxyloxyimino)acetamido]-3-(1-N-phenylpyrazol-5-ylthio)-3-cephem-4-carboxylic acid
(7R)-7-[(Z)-2-(aminothiazol-4-yl)-2-(cyclopentyloxyimino)acetamido]-3-(2-(2-phenylpyridin-3-ylthio)-3-cephem-4-carboxylic acid
(7R)-7-[((2-aminoethylphenyl)acetyl)amino]-3-(1-N-phenylpyrazol-5-ylthio)-3-cephem-4-carboxylic acid
(7R)-7-[(Z)-2-(2-amino-5-chlorothiazol-4-yl)-2-(2-fluoroethyloxyimino) acetamido]-3-(1-N-phenylpyrazol-5-ylthio)-3-cephem-4-carboxylic acid
(7R)-7-[(Phenylacetyl)amino]-3-(2-cyanopyridin-3-ylthio)-3-cephem-4-carboxylic acid
(7R)-7-[(Phenylacetyl)amino]-3-(2-(pyrazol-1-yl)pyridin-3-ylthio)-3-cephem-4-carboxylic acid
(7R)-7-[(Z)-2-(aminothiazol-4-yl)-2-(3-pentyloxyimino)acetamido]-3-(1-N-phenylpyrazol-5-ylthio)-3-cephem-4-carboxylic acid
(7R)-7-[(Phenylacetyl)amino]-3-(1-N-(pyridin-2-yl)pyrazol-5-ylthio)-3-cephem-4-carboxylic acid
(7R)-7-[(methylthioacetyl)amino]-3-(1-N-phenylpyrazol-5-ylthio)-3-cephem-4-carboxylic acid
(7R)-7-[(cyclopropylacetyl)amino]-3-(1-N-phenylpyrazol-5-ylthio)-3-cephem-4-carboxylic acid
(7R)-7-[(Z)-2-(2-aminothiazol-4-yl)-2-(cyclopropylmethyloxyimino)acetamido]-3-(1-N-phenylpyrazol-5-ylthio)-3-cephem-4-carboxylic acid
(7R)-7-[(hexanoyl)amino]-3-(1-N-phenylpyrazol-5-ylthio)-3-cephem-4-carboxylic acid
(7R)-7-[(4-pyridylthioacetyl)amino]-3-(1-N-phenylpyrazol-5-ylthio)-3-cephem-4-carboxylic acid
(7R)-7-[(2-furylacetyl)amino]-3-(1-N-phenylpyrazol-5-ylthio)-3-cephem-4-carboxylic acid
(7R)-7-[(phenylacetyl)amino]-3-(1-N-(phenylpyrazol-5-ylthio)-3-cephem-4-carboxylic acid
(7R)-7-[(Phenylacetyl)amino]-3-(1-N-(1-N-(3-nitrophenyl)pyrazol-5-ylthio)-3-cephem-4-carboxylic acid
(7R)-7-[(Phenylacetyl)amino]-3-(1-N-(4-methoxyphenyl)pyrazol-5-ylthio)-3-cephem-4-carboxylic acid
(7R)-7-[(2-dithiolanylcarbonyl)amino]-3-(1-N-phenylpyrazol-5-ylthio)-3-cephem-4-carboxylic acid D. Synthesis of Compounds of Structure II The compounds of the present invention may be readily prepared in accordance with the following schemes. However, it will be appreciated that other synthetic pathways for forming the compounds of the invention are available and that the following is offered merely byway of example, and not limitation. It will be further recognized that various protecting and deprotecting strategies will be employed which are standard in the art (see, e.g., Green and Wuts). Those of skill in the art will recognize that the selection of any particular protecting group (e.g., a carboxy protecting group) will depend on the stability of the protected moiety with respect to subsequent reaction conditions.

Generally, the synthesis of the cephalosporins of the present invention may be achieved using well-known methods and readily available materials (see, e.g., March; Larock, COMPREHENSIVE ORGANIC TRANSFORMATIONS (VCH Publishers, 1989); and G. I. Georg, THE ORGANIC CHEMISTRY OF β-LACTAMS, (VCH 1992), each of which is incorporated herein by reference). As shown below in Scheme 1, treatment of the cephem triflate 1 with the desired thiolate nucleophile —S(CH$_2$)$_n$Y, using standard methods such as those described in Farina et al., *J. Org. Chem*, 54:4962 (1989) and U.S. Pat. No. 4,870,168 to Baker, et al., (both of which are incorporated herein by reference), provides the 3-thio derivative 2. Subsequent deprotection using procedures known to those skilled in the art affords the biologically active 4-carboxycephem 3.

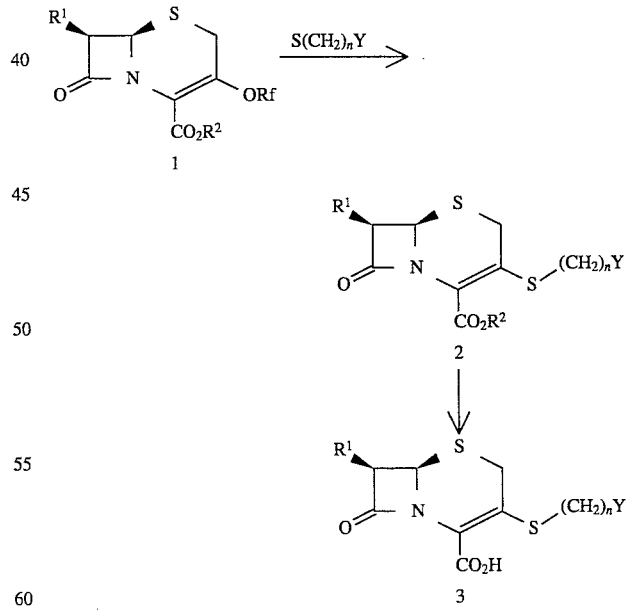

Compound 1 is formed readily from commercially available starting materials, such as the reaction of (7R)-7-[(phenylacetyl)amino]-3-hydroxy-3-cephem-4-carboxylic acid (Otsuka Chemical Co., Ltd., Otsuka, Japan) with triflic anhydride (Aldrich, Milwaukee, Wis.), using known procedures (see, e.g., Farina; and U.S. Pat. No. 4,870,168 to Baker, et al.) Other 3-hydroxy-3-cephems may be formed from the ozonolysis of 3-exomethylene cephems using known procedures (see, e.g., Farina).

Similarly, the thiolate nucleophile carrying the desired substituent Y and the spacer —$(CH_2)_n$— may be formed using known procedures and commercially available starting materials. For example, for the case Y=substituted aromatic and n=0, the desired thiolate nucleophile may be formed using well known techniques for performing nucleo- An alternative synthetic route to the desired cephem 3 is described below, wherein a suitably amine-protected cephem 4 (P denotes the protecting group) is further reacted to provide non-protected intermediate 5 which is then reacted with the appropriate acylation reagent(s) and deprotected to provide the desired product 3. Another alternative route is also shown wherein the carboxyl deprotection is performed first to form intermediate 6, followed by the removal of the protecting group and the addition of the desired acyl derivative.

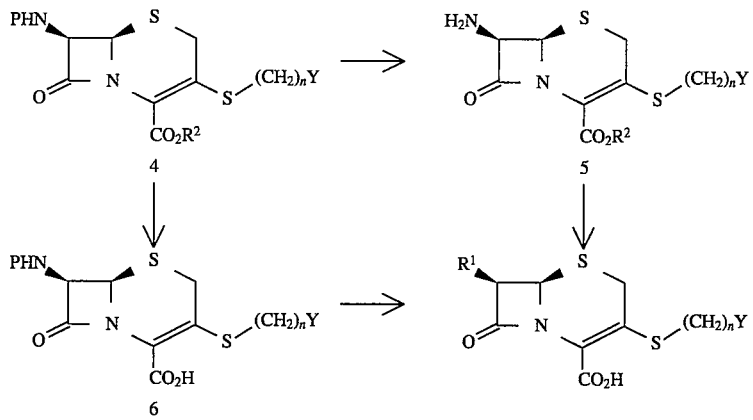

philic or electrophilic aromatic substitutions with commercially available aromatic thiols (e.g., thiophenol, available from Aldrich) or with aromatic thiols formed using known techniques (see March). For the case n≠0, the 3-thio-3-cephem derivative of the β-lactam may be reacted with the group $LG-CH_2Y$, where LG is an appropriate leaving group, such as halogen, e.g., iodo (see, e.g., J. Antibiot. pp. 498–506 (May 1991, which is incorporated herein by reference).

The substituent $R^1$ may be any of the groups described above and are either available commercially (e.g., from Aldrich, Milwaukee, Wis.) or can be formed using known techniques and starting materials (see, e.g., March; Larock). These groups can be substituted for those present on the starting material by variety of well known techniques (see, e.g., Barrett, J. C. S. Perkin I, 1629 (1979) or Chauvette, J. Org. Chem. 36:1259 (1971), both of which are incorporated herein by reference), such as by transamination of an existing substituent for the desired substituent, or hydrolytic removal of the existing substituent followed by reaction with a suitably reactive form of desired substituent, such as an acyl chloride. Again, the appropriate reagents and techniques will be apparent to those of skill in the art.

The carboxyl group $R^2$ may be those protecting groups amenable to reductive cleavage, such as benzyl, p- or o-nitrobenzyl, 2,2,2-trichloroethyl, allyl, cinnamyl, benzhydryl, 2-chloroallyl and the like. Alternatively, $R^2$ may be a protecting group amenable to acidic cleavage, such as t-butyl, t-amyl, trityl, 4-methoxytrityl, 4,4'-dimethoxytrityl, trimethylsilyl, t-butyldimethylsilyl, phenacyl, β-(trimethylsilyl)ethyl, benzyl, 4-(or 2-methoxybenzyl, 2,4-dimethoxybenzyl, 3,4-dimethoxybenzyl, 2,4,6-trimethoxybenzyl, methoxymethyl, benzhydryl, or 3,3-dimethylallyl. Preferred protecting groups are p-methoxybenzyl, p-nitrobenzyl, allyl and benzhydryl. Such groups may be attached to the unprotected carboxyl group of the cephalosporin starting material using known reagents and techniques, such as those described in Green and Wuts.

Preferred amine protecting groups include trityl, formyl, phenoxyacetyl, trichloroacetyl, chloroacetyl, bromoacetyl, iodoacetyl, urethane-type protecting groups [such as t-butoxycarbonyl, benzyloxycarbonyl, 4-methoxybenzyloxycarbonyl, 4-nitrobenzyloxycarbonyl, 2-chloroallylcarbonyl, allyoxycarbonyl, 2-(trimethylsilyl)ethoxycarbonyl, 2,2,2-trichloroethoxycarbonyl, $(C_4-C_6)$-cycloalkanyloxycarbonyl or 9-fluorenylmethoxycarbonyl (FMOC)]. Especially preferred protecting groups are trityl, allyoxycarbonyl, benzyloxycarbonyl, phenoxyacetyl, and t-butoxycarbonyl. These may be attached and removed using standard techniques (see Green and Wuts). The selection of the amine-protecting group to be employed will depend on the stability of the protected β-lactam to the subsequent reaction conditions.

For the cases wherein Y is biphenyl or substituted biphenyls, the biphenyl moiety may also be introduced by the carbon-carbon coupling of a 3-(halophenylthio)cephem (or 3-(trifluorosulfonyloxyphenylthio)cephem) 8 with an appropriately substituted phenyltrialkylstannane in the presence of a palladium catalyst and triaryl(or triheterocyclic)phosphine such as tris(dibenzylideneacetone)dipalladium(0)-tris(2-furyl)phosphine to form the desired substituted (biphenylthio)cephem 9 as shown below.

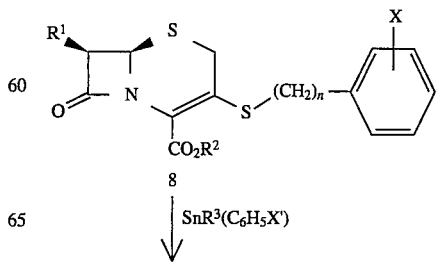

17

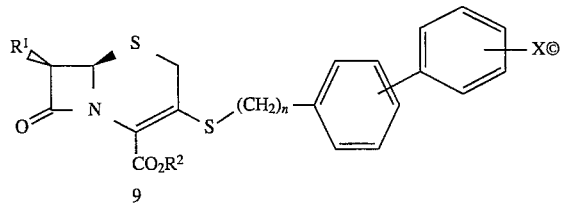

9

E. Synthesis of Compounds of Structure III

The compounds of general structure III are prepared similarly to those of general structure II. In many cases, a key step is the coupling of a hydroxymethyl-substituted benzenethiolate with cephem triflate 1. This affords a key intermediate, which upon conversion of the hydroxyl group to an appropriate leaving group, allows conversion to the desired group $R^{12}$ by reaction with an appropriate nucleophile.

F. Synthesis of Compounds of Structures IV and V

The compounds of general structure IV and V are prepared similarly to those of general structure II, by coupling a heteroaromatic thiolate with cephem triflate 1. The requisite heteroaromatic thiols are prepared by a variety of methods known in the literature, as described in the Examples.

III. Pharmaceutical Applications and Preparations

According to this invention, a therapeutically or pharmaceutically effective amount of a cephalosporin and particularly, a compound of Structure II, is administered to a mammal suffering from an β-lactam resistant bacterial infection, especially resistant *S. aureus*, in an amount effective to at least partially relieve the infection. Especially important are infections resulting from β-lactam resistant strains having similar β-lactam resistant activity to strains such as *S. aureus* ATCC 29213, *S. aureus* ATCC 25913, *S. aureus* ATCC 31432, *S. aureus* col (Meth$^R$)(lac$^-$), *S. aureus* 76 (Meth$^R$) (lac$^+$), *S. aureus* ColBA (Meth$^S$)(lac$^-$), *E. faecium* ATCC 35667, or *E. faecalis* ATCC 29212.

The compositions containing the compound(s) of the invention can be administered for prophylactic and/or therapeutic treatments. In therapeutic applications, the compositions are administered to a patient already suffering from an infection, as described above, in an amount sufficient to cure or at least partially arrest the symptoms of the infection. An amount adequate to accomplish this is defined as "therapeutically effective amount or dose." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to or otherwise at risk of a particular infection. Such an amount is defined to be a "prophylactically effective amount or dose." In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compound of the invention will be in the range of 0.1 to 1000 milligram (mg) per recipient per day, preferably in the range of 1 to 100

18 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 250 mg/kg of patient body weight, between about one to four times per day.

While it is possible to administer the active ingredient of this invention alone, it is preferable to present it as part of a pharmaceutical formulation. The formulations of the present invention comprise at least one compound or inhibitor of this invention in a therapeutically or pharmaceutically effective dose together with one or more pharmaceutically or therapeutically acceptable carriers. Solid carriers include, e.g., starch, lactose, dicalcium phosphate, microcrystalline cellulose, sucrose, and kaolin, and optionally other therapeutic ingredients. Liquid carriers include, e.g., sterile water, polyethylene glycols, non-ionic surfactants, and edible oils such as corn, peanut and sesame oils. In addition, various adjuvants such as are commonly used in the art may be included. For example: flavoring agents, coloring agents, preservatives, and antioxidants, e.g., vitamin E, ascorbic acid, BHT and BHA. Various other considerations are described, e.g., in Gilman et al. (eds) (1990) Goodman and Gilman's: The Pharmacological Basis of Therapeutics, 8th Ed., Pergamon Press; and Remington's supra. Methods for administration are discussed therein, e.g., for oral, intravenous, intraperitoneal, or intramuscular administration, and others. Pharmaceutically acceptable carriers will include water, saline, buffers, and other compounds described, e.g., in the MERCK INDEX, Merck & Co., Rahway, N.J. Generally, preferred routes of administration are intravenous and intraperitoneal.

These pharmacological agents can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Generally, a pharmacologically acceptable salt of the compound will be used to simplify preparation of the composition. Preferred salts include sodium, potassium, arginine, glycine, alanine, threonine. These are prepared, preferably, in water suitably mixed with a surfactant such as hydroxypropylcellulose.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular subcutaneous, intramedullary injections, as well an intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art.

In soft capsules, the active compounds may be dissolved or suspended in suitable liquids, such as fatty oils, liquid paraffin, or liquid polyethylene glycols. In addition, stabilizers may be added.

IV. Biological Activity

In Vitro Antibacterial Evaluation

The compounds of the invention were evaluated against several β-lactam resistant bacteria strains by determining the minimum inhibitory concentration (MIC, μg/ml) of each compound with respect to each strain. The MIC, the lowest concentration of antibiotic which inhibits growth of the test organism, was determined by the agar dilution method.

To determine the MIC for bacterial isolates, the test compound was incorporated in a series of two-fold dilutions into liquified Mueller-Hinton agar. Upon solidification, a number of different bacterial strains were spot inoculated with a replicating device onto the agar surface. After overnight incubation, the MIC breakpoint was determined as the lowest drug concentration that completely inhibited growth, disregarding a single colony or a faint haze. The procedures used in these studies have been standardized by the National Committee for Clinical Laboratory Standards (NCCLS), as per the NCCLS publication entitled METHODS FOR DILUTION ANTIMICROBIAL SUSCEPTIBILITY TESTS (1991), which is incorporated herein by reference.

Aliquots of antimicrobial agents were prepared in phosphate buffered saline (PBS) at pH 7.2. Tween 20 or DMSO was used as a solubilizing vehicle as needed. Standard methods of vortexing, sonicating and gentle heat were used to facilitate solubilizing the test agent. Typically, the concentration of the stock solution was 10× that of the highest drug concentration tested. A 1.28 mg/mL stock solution was used with a subsequent highest working concentration of 128 μg/mL. Serial two-fold dilutions were done through ≦0.25 μg/mL. Each drug level was tested in duplicate. Two-fold drug dilutions were done in sterile 50 mL tubes with a final drug volume of 5 mL. Upon the addition of 45 mL of molten agar, a 10-fold dilution resulted. Two, 25 mL plates were then poured into 15×150 mm square Petri plates with grids and allowed to harden.

A control plate with a reference drug, either cefotaxime, vancomycin or imipenem, was used as the positive growth control. Stock concentrations of reference antibiotics were prepared and frozen at −80° C. Upon preparation, the control plates were sealed and stored in the refrigerator for up to 1 week prior to use; however, imipenem control plates had to be prepared just prior to use. All test plates were used within 24 hours of preparation.

Satisfactory results were obtained where the inoculum contained about $10^4$ colony forming units (cfu) ±0.5 logs. Starting with pure cultures of the test isolates on agar plates, a few isolated colonies were transferred to a tube of nutrient broth and allowed to grow 4–6 hours at 35°–36° C. to reach log-phase growth. Dropwise addition of the broth culture to PBS was done to match a 0.5 McFarland turbidity standard equal to $10^8$ cfu/mL. This was further diluted ten-fold in PBS to reach a working inoculum concentration of $10^7$ cfu/mL. When 1 μL of the working inoculum was applied to the agar surface a concentration of about $10^4$ cfu per spot was obtained.

Disposable sterile 1 μL loops were used to inoculate test plates, with each isolate in a designated grid on the agar plate. An alternate method of inoculation involved the use of a replica plater, a device with 48 steel pins allowing the simultaneous inoculation of multiple isolates. After the spots had dried, the plates were incubated at 35°–36° C. for 16–20 hours. Endpoints were assessed as the minimum inhibitory concentration (MIC) of antimicrobial agent.

These results are shown in Table I below. The novel agents of this invention are notable for their enhanced activity against S. aureus Col and Enterococci (*E. faecium* and *E. faecalis*). The *S. aureus* Col strain is a high-level PBP2a producer, whereas *S. aureus* Col 8A, its isogenic partner, lacks PBP2a. Certain compounds, such as 6 ((7R)-7-(Phenylacetyl)amino]-3-(o-iodophenylthio)-3-cephem-4-carboxylic acid) and 9 ((7R)-7-[(Phenylacetyl)amino]-3-(2-biphenylthio)-3-cephem-4-carboxylic acid), show broad activity against both *S. aureus* Col and *S. aureus* Col 8A, as well as Enterococci. The *S. aureus* Col 8A strain was highly responsive to all test agents including the Cefotaxime control. Thus, the compounds of the present invention are effective against PBP2a-producing bacteria. Compound 12, while lacking activity against *S. aureus* Col, shows potent activity against enterococci. Certain other compounds of the present invention, such as 22 ((7R)-7-[(Z)-2-(aminothiazol-4-yl)-2-(hydroxyimino)acetamido]-3-(o-iodophenylthio)-3-cephem-4-carboxylic acid), are effective against *E. coli* in addition to Gram-positive organisms.

TABLE 1

Antimicrobial Properties of 7-(Acylamido)-3-(arylthio)cephems

| Organism | Cefotax. | 1 | 2 | 3 | 4 | 5 | 6 |
|---|---|---|---|---|---|---|---|
| *S. aureus* ATCC 29213 | 2 | 0.03 | 0.03 | 0.03 | 0.125 | 0.03 | <0.015 |
| *S. aureus* ATCC 25923 | <1 | <0.015 | <0.015 | <0.015 | <0.06 | <0.015 | <0.015 |
| *S. epidermidis* ATCC 31432 | 2 | <0.015 | <0.015 | <0.015 | <0.06 | <0.015 | <0.015 |
| *S. aureus* Col (Meth$^R$)(lac$^-$) | >32 | 16 | 2 | 2 | 1–2 | 2 | 1 |
| *S. aureus* 76 (Meth$^R$)(lac$^+$) | >32 | 32 | 16 | 16 | 4 | 16 | 1 |
| *S. aureus* Col8A (Meth$^S$)(lac$^-$) | 2 | 0.03 | 0.03 | 0.015 | <0.06 | 0.03 | <0.015 |
| *S. haemolyticus* (Meth$^R$) | >32 | >32 | 16 | 16 | 16 | 16 | 4 |
| *E. faecium* ATCC 35667 | >32 | 8 | 2 | 4 | 2 | 4 | 0.5 |
| *E. faecalis* ATCC 29212 | >32 | 2 | 2 | 2 | 4 | 2 | 0.5 |
| *E. coli* ATCC 25922 | <1 | >32 | >32 | >32 | >32 | >32 | >32 |
| *P. aeruginosa* ATCC 27853 | 8–16 | >32 | >32 | >32 | >32 | >32 | >32 |
| *X. maltophilia* ATCC 13637 | >32 | >32 | >32 | >32 | >32 | >32 | >32 |

| Organism | Cefotax. | 7 | 8 | 9 | 10 | 11 | 12 |
|---|---|---|---|---|---|---|---|
| *S. aureus* ATCC 29213 | 2 | <0.06 | <0.125 | 0.25 | 0.125 | 0.125 | <0.06 |
| *S. aureus* ATCC 25923 | <1 | <0.06 | <0.125 | 0.125 | <0.06 | <0.015 | <0.06 |
| *S. epidermidis* ATCC 31432 | 2 | <0.06 | <0.125 | 0.125 | <0.06 | 0.03 | <0.06 |
| *S. aureus* Col (Meth$^R$)(lac$^-$) | >32 | 4 | 4 | 4 | 8 | 1 | >32 |
| *S. aureus* 76 (Meth$^R$)(lac$^+$) | >32 | 16 | >32 | 8 | 32 | 4 | >32 |
| *S. aureus* Col8A (Meth$^S$)(lac$^-$) | 2 | 0.06 | <0.125 | 0.25 | 0.125 | 0.06 | <0.06 |
| *S. haemolyticus* (Meth$^R$) | >32 | — | — | 0.125 | — | 4–8 | — |

TABLE 1-continued

| Organism | Cefotax. | | | | | | |
|---|---|---|---|---|---|---|---|
| E. faecium ATCC 35667 | >32 | — | — | 2 | — | 4 | — |
| E. faecalis ATCC 29212 | >32 | 1 | 4 | 4 | 2 | 2 | 4 |
| E. coli ATCC 25922 | <1 | >32 | >32 | >32 | >32 | >32 | >32 |
| P. aeruginosa ATCC 27853 | 8–16 | >32 | >32 | >32 | >32 | >32 | >32 |
| X. maltophilia ATCC 13637 | >32 | >32 | >32 | >32 | >32 | >32 | >32 |

| Organism | Cefotax. | 13 | 14 | 15 | 16 | 17 | 18 |
|---|---|---|---|---|---|---|---|
| S. aureus ATCC 29213 | 2 | 0.06 | 0.25 | 0.06 | <0.5 | <0.25 | <0.25 |
| S. aureus ATCC 25923 | <1 | <0.015 | 0.06 | 0.03 | — | — | — |
| S. epidermidis ATCC 31432 | 2 | 0.03 | 0.06 | 0.03 | <0.5 | <0.25 | <0.25 |
| S. aureus Col (Meth$^R$)(lac$^-$) | >32 | 4 | 4 | — | <0.5 | 2 | 4 |
| S. aureus 76 (Meth$^R$)(lac$^+$) | >32 | 16 | 4 | 8 | 4 | 4 | 16 |
| S. aureus Col8A (Meth$^S$)(lac$^-$) | 2 | 0.06 | 0.25 | 0.06 | <0.5 | <0.25 | <0.25 |
| S. haemolyticus (Meth$^R$) | >32 | 16 | 8 | 16 | 16 | 8 | 32 |
| E. faecium ATCC 35667 | >32 | 4 | 1 | 2 | 4 | 1 | 4 |
| E. faecalis ATCC 29212 | >32 | 2 | 2 | 2 | — | — | — |
| E. coli ATCC 25922 | <1 | >32 | >32 | >32 | >16 | >64 | >32 |
| P. aeruginosa ATCC 27853 | 8–16 | >32 | >32 | >32 | — | — | — |
| X. maltophilia ATCC 13637 | >32 | >32 | >32 | >32 | — | — | — |

| Organism | Cefotax. | 19 | 20 | 21 | 22 | 23 | 24 |
|---|---|---|---|---|---|---|---|
| S. aureus ATCC 29213 | 2 | <0.25 | <0.25 | <0.25 | <0.25 | <0.25 | <0.25 |
| S. aureus ATCC 25923 | <1 | — | — | — | — | — | — |
| S. epidermidis ATCC 31432 | 2 | <0.25 | <0.25 | <0.25 | <0.25 | <0.25 | <0.25 |
| S. aureus Col (Meth$^R$)(lac$^-$) | >32 | 4 | 0.5 | 1 | 2 | 2 | 1 |
| S. aureus 76 (Meth$^R$)(lac$^+$) | >32 | 16 | 4 | 4 | 4 | 8 | 4 |
| S. aureus Col8A (Meth$^S$)(lac$^-$) | 2 | <0.25 | <0.25 | <0.25 | 0.5 | <0.25 | <0.25 |
| S. haemolyticus (Meth$^R$) | >32 | 32 | 8 | 32 | 4 | 16 | 8 |
| E. faecium ATCC 35667 | >32 | 2 | 2 | 4 | 2 | 2 | 2 |
| E. faecalis ATCC 29212 | >32 | — | — | — | — | — | — |
| E. coli ATCC 25922 | <1 | >32 | >32 | >32 | 4 | >32 | >32 |
| P. aeruginosa ATCC 27853 | 8–16 | — | — | — | — | — | — |
| X. maltophilia ATCC 13637 | >32 | — | — | — | — | — | — |

| Organism | Cefotax. | 25 | 26 | 27 | 28 | 29 | 30 |
|---|---|---|---|---|---|---|---|
| S. aureus ATCC 29213 | 2 | 0.125 | <0.25 | <0.25 | <0.25 | <0.25 | <0.25 |
| S. aureus ATCC 25923 | <1 | — | — | — | — | — | — |
| S. epidermidis ATCC 31432 | 2 | <0.06 | <0.25 | <0.25 | <0.25 | <0.25 | <0.25 |
| S. aureus Col (Meth$^R$)(lac$^-$) | >32 | 1 | 0.5 | 1 | 1 | 1 | 0.5 |
| S. aureus 76 (Meth$^R$)(lac$^+$) | >32 | 4 | 4 | 4 | 4 | 4 | 2 |
| S. aureus Col8A (Meth$^S$)(lac$^-$) | 2 | 0.125 | <0.25 | <0.25 | <0.25 | <0.25 | <0.25 |
| S. haemolyticus (Meth$^R$) | >32 | 16 | 8 | 16 | 8 | 16 | 4 |
| E. faecium ATCC 35667 | >32 | 2 | 2 | 1 | 2 | 1 | 1 |
| E. faecalis ATCC 29212 | >32 | — | — | — | — | — | — |
| E. coli ATCC 25922 | <1 | >32 | >32 | >32 | >32 | >32 | >32 |
| P. aeruginosa ATCC 27853 | 8–16 | — | — | — | — | — | 13 |
| X. maltophilia ATCC 13637 | >32 | — | — | — | — | — | — |

| Organism | Cefotax. | 31 | 32 | 33 | 34 | 35 | 36 |
|---|---|---|---|---|---|---|---|
| S. aureus ATCC 29213 | 2 | <0.25 | <0.25 | <0.25 | — | — | — |
| S. aureus ATCC 25923 | <1 | — | — | — | <0.25 | <0.25 | <0.25 |
| S. epidermidis ATCC 31432 | 2 | <0.25 | <0.25 | <0.25 | <0.25 | <0.25 | <0.25 |
| S. aureus Col (Meth$^R$)(lac$^-$) | >32 | 1 | 1 | 1 | 2 | 0.5 | 2 |
| S. aureus 76 (Meth$^R$)(lac$^+$) | >32 | 4 | 4 | 4 | 8 | 2 | 8 |
| S. aureus Col8A (Meth$^S$)(lac$^-$) | 2 | <0.25 | <0.25 | <0.25 | <0.25 | <0.25 | <0.25 |
| S. haemolyticus (Meth$^R$) | >32 | 8 | 16 | 16 | 8 | 8 | 16 |
| E. faecium ATCC 35667 | >32 | 4 | 2 | 1 | 2 | 1 | 4 |
| E. faecalis ATCC 29212 | >32 | — | — | — | 2 | 1 | 2 |
| E. coli ATCC 25922 | <1 | >32 | >32 | >32 | >32 | >32 | >32 |
| P. aeruginosa ATCC 27853 | 8–16 | — | — | — | >32 | >32 | >32 |
| X. maltophilia ATCC 13637 | >32 | — | — | — | — | — | — |

| Organism | Cefotax. | 37 | 38 | 39 | 40 | 41 | 42 |
|---|---|---|---|---|---|---|---|
| S. aureus ATCC 29213 | 2 | — | — | — | — | — | — |
| S. aureus ATCC 25923 | <1 | <0.25 | <0.25 | <0.25 | <0.25 | <0.25 | <0.25 |
| S. epidermidis ATCC 31432 | 2 | <0.25 | <0.25 | <0.25 | <0.25 | <0.25 | <0.25 |
| S. aureus Col (Meth$^R$)(lac$^-$) | >32 | 2 | 4 | 0.5 | 4 | 1 | 4 |
| S. aureus 76 (Meth$^R$)(lac$^+$) | >32 | 8 | 16 | 4 | 16 | 4 | 8 |
| S. aureus Col8A (Meth$^S$)(lac$^-$) | 2 | <0.25 | <0.25 | <0.25 | <0.25 | <0.25 | 0.5 |
| S. haemolyticus (Meth$^R$) | >32 | 16 | 32 | 8 | 32 | 16 | 16 |
| E. faecium ATCC 35667 | >32 | 2 | 4 | 2 | 4 | 2 | 2 |
| E. faecalis ATCC 29212 | >32 | 2 | 4 | 2 | 4 | 4 | 2 |

TABLE 1-continued

| Organism | Cefotax. | | | | | | |
|---|---|---|---|---|---|---|---|
| E. coli ATCC 25922 | <1 | >32 | >32 | >32 | >32 | >32 | 32 |
| P. aeruginosa ATCC 27853 | 8–16 | >32 | >32 | >32 | >32 | >32 | >32 |
| X. maltophilia ATCC 13637 | >32 | — | — | — | — | — | — |

| Organism | Cefotax. | 43 | 44 | 45 | 46 | 47 | 48 |
|---|---|---|---|---|---|---|---|
| S. aureus ATCC 29213 | 2 | — | — | — | — | — | — |
| S. aureus ATCC 25923 | <1 | <0.25 | <0.25 | <0.25 | <0.25 | <0.25 | <0.25 |
| S. epidermidis ATCC 31432 | 2 | <0.25 | <0.25 | <0.25 | <0.25 | <0.25 | <0.25 |
| S. aureus Col (Meth$^R$)(lac$^-$) | >32 | 4 | 2 | 4 | 1 | 1 | 4 |
| S. aureus 76 (Meth$^R$)(lac$^+$) | >32 | 8 | 4–8 | 16 | 8 | 8 | 16 |
| S. aureus Col8A (Meth$^S$)(lac$^-$) | 2 | <0.25 | <0.25 | 0.5 | <0.25 | <0.25 | 0.5 |
| S. haemolyticus (Meth$^R$) | >32 | 16 | 8 | 32 | 16 | 16 | 16 |
| E. faecium ATCC 35667 | >32 | 4 | 4 | 4 | 2 | 2 | 4 |
| E. faecalis ATCC 29212 | >32 | 4 | 4 | 4 | 2 | 4 | 4 |
| E. coli ATCC 25922 | <1 | >32 | >32 | >32 | >32 | >32 | >32 |
| P. aeruginosa ATCC 27853 | 8–16 | >32 | >32 | >32 | >32 | >32 | >32 |
| X. maltophilia ATCC 13637 | >32 | — | — | — | — | — | — |

| Organism | Cefotax. | 49 | 50 | 51 | 52 | 53 | 54 |
|---|---|---|---|---|---|---|---|
| S. aureus ATCC 29213 | 2 | — | — | 0.5 | 0.5 | 1 | <0.25 |
| S. aureus ATCC 25923 | <1 | <0.25 | <0.25 | <0.25 | <0.25 | — | — |
| S. epidermidis ATCC 31432 | 2 | <0.25 | <0.25 | <0.25 | <0.25 | — | <0.25 |
| S. aureus Col (Meth$^R$)(lac$^-$) | >32 | 4 | 2 | 4 | 4 | 4 | 1 |
| S. aureus 76 (Meth$^R$)(lac$^+$) | >32 | 16 | 8 | 8 | 16 | 8 | 8 |
| S. aureus Col8A (Meth$^S$)(lac$^-$) | 2 | 0.5 | <0.25 | <0.25 | 0.5 | 1 | <0.25 |
| S. haemolyticus (Meth$^R$) | >32 | 32 | 8 | 32 | 16 | 8 | 16 |
| E. faecium ATCC 35667 | >32 | 4 | 4 | 4 | 2 | 8 | 4 |
| E. faecalis ATCC 29212 | >32 | 4 | 4 | 4 | 4 | 8 | — |
| E. coli ATCC 25922 | <1 | >32 | 8 | >32 | >32 | 1 | >32 |
| P. aeruginosa ATCC 27853 | 8–16 | >32 | >32 | >32 | >32 | 8 | >32 |
| X. maltophilia ATCC 13637 | >32 | — | — | — | — | — | — |

| Organism | Cefotax. | 55 | 56 | 57 |
|---|---|---|---|---|
| S. aureus ATCC 29213 | 2 | — | — | — |
| S. aureus ATCC 25923 | <1 | <0.25 | <0.25 | <0.25 |
| S. epidermidis ATCC 31432 | 2 | <0.25 | <0.25 | <0.25 |
| S. aureus Col (Meth$^R$)(lac$^-$) | >32 | 4 | 1 | 0.5 |
| S. aureus 76 (Meth$^R$)(lac$^+$) | >32 | 16 | 4 | 2 |
| S. aureus Col8A (Meth$^S$)(lac$^-$) | 2 | <0.25 | <0.25 | <0.25 |
| S. haemolyticus (Meth$^R$) | >32 | 16 | 16 | 4 |
| E. faecium ATCC 35667 | >32 | 8 | 4 | 1 |
| E. faecalis ATCC 29212 | >32 | 16 | 2 | 2 |
| E. coli ATCC 25922 | <1 | >32 | >32 | 32 |
| P. aeruginosa ATCC 27853 | 8–16 | >32 | >32 | 32 |
| X. maltophilia ATCC 13637 | >32 | — | — | — |

| Organism | Cefotax. | 58 | 59 | 60 | 61 | 62 | 63 |
|---|---|---|---|---|---|---|---|
| S. aureus ATCC 29213 | 2 | — | — | — | — | — | — |
| S. aureus ATCC 25923 | <1 | <0.25 | <0.25 | <0.25 | <0.25 | <0.25 | <0.25 |
| S. epidermidis ATCC 31432 | 2 | <0.25 | <0.25 | <0.25 | <0.25 | <0.25 | <0.25 |
| S. aureus Col (Meth$^R$)(lac$^-$) | >32 | <0.25 | 2 | 0.5 | 4 | 4 | 4 |
| S. aureus 76 (Meth$^R$)(lac$^+$) | >32 | 4 | 8 | 4 | 16 | 16 | 16 |
| S. aureus Col8A (Meth$^S$)(lac$^-$) | 2 | <0.25 | <0.25 | <0.25 | 0.5 | <0.25 | <0.25 |
| S. haemolyticus (Meth$^R$) | >32 | 4 | 16 | 4–8 | >32 | 32 | 32 |
| E. faecium ATCC 35667 | >32 | 0.5 | 4 | 1 | 4 | 4 | 1 |
| E. faecalis ATCC 29212 | >32 | 1 | 4 | 1 | 4 | 2 | 1 |
| E. coli ATCC 25922 | <1 | 32 | >32 | >32 | >32 | >32 | 8 |
| P. aeruginosa ATCC 27853 | 8–16 | >32 | >32 | >32 | >32 | >32 | >32 |

| Organism | Cefotax. | 64 | 65 | 66 | 67 | 68 | 69 |
|---|---|---|---|---|---|---|---|
| S. aureus ATCC 29213 | 2 | <0.25 | <0.25 | — | <0.25 | <0.25 | <0.25 |
| S. aureus ATCC 25923 | <1 | <0.25 | <0.25 | <0.25 | <0.25 | <0.25 | <0.25 |
| S. epidermidis ATCC 31432 | 2 | <0.25 | <0.25 | <0.25 | <0.25 | <0.25 | <0.25 |
| S. aureus Col (Meth$^R$)(lac$^-$) | >32 | 0.5 | 8 | 2 | 4 | 8 | 4 |
| S. aureus 76 (Meth$^R$)(lac$^+$) | >32 | 4 | 32 | 8 | 16 | 16 | 16 |
| S. aureus Col8A (Meth$^S$)(lac$^-$) | 2 | <0.25 | <0.25 | <0.25 | <0.25 | <0.25 | <0.25 |
| S. haemolyticus (Meth$^R$) | >32 | 8 | 32 | 8 | 16 | 32 | 32 |
| E. faecium ATCC 35667 | >32 | 0.5 | 2 | 1 | 2 | 4 | 2 |
| E. faecalis ATCC 29212 | >32 | 1 | 1 | 4 | 2 | 4 | 2 |
| E. coli ATCC 25922 | <1 | >32 | >32 | >32 | >32 | >32 | >32 |
| P. aeruginosa ATCC 27853 | 8–16 | >32 | >32 | >32 | >32 | >32 | >32 |

TABLE 1-continued

| Organism | Cefotax. | 70 | 71 | 72 | 73 | 74 | 75 |
|---|---|---|---|---|---|---|---|
| S. aureus ATCC 29213 | 2 | <0.25 | <0.25 | <0.25 | <0.25 | <0.25 | <0.25 |
| S. aureus ATCC 25923 | <1 | <0.25 | <0.25 | <0.25 | <0.25 | <0.25 | <0.25 |
| S. epidermidis ATCC 31432 | 2 | <0.25 | <0.25 | <0.25 | <0.25 | <0.25 | <0.25 |
| S. aureus Col (Meth$^R$)(lac$^-$) | >32 | 4 | 16 | 4 | 4 | 16 | 8 |
| S. aureus 76 (Meth$^R$)(lac$^+$) | >32 | 16 | >32 | 16 | 16 | 32 | 32 |
| S. aureus Col8A (Meth$^S$)(lac$^-$) | 2 | <0.25 | <0.25 | <0.25 | <0.25 | <0.25 | <0.25 |
| S. haemolyticus (Meth$^R$) | >32 | 32 | >32 | 32 | 32 | >32 | >32 |
| E. faecium ATCC 35667 | >32 | 2 | 2 | 2 | 1 | 2 | 2 |
| E. faecalis ATCC 29212 | >32 | 0.5 | 1 | 1 | 0.5 | 1 | 1 |
| E. coli ATCC 25922 | <1 | >32 | >32 | >32 | >32 | >32 | >32 |
| P. aeruginosa ATCC 27853 | 8–16 | >32 | >32 | >32 | >32 | >32 | >32 |

| Organism | Cefotax. | 76 | 77 | 78 | 79 | 80 |
|---|---|---|---|---|---|---|
| S. aureus ATCC 29213 | 2 | <0.25 | <0.25 | 0.25 | 0.06 | <0.06 |
| S. aureus ATCC 25923 | <1 | <0.25 | <0.25 | — | — | — |
| S. epidermidis ATCC 31432 | 2 | <0.25 | <0.25 | — | — | — |
| S. aureus Col (Meth$^R$)(lac$^-$) | >32 | 2 | 8 | 4 | 4 | 2 |
| S. aureus 76 (Meth$^R$)(lac$^+$) | >32 | 8 | 32 | 16 | 8 | 8 |
| S. aureus Col8A (Meth$^S$)(lac$^-$) | 2 | <0.25 | <0.25 | 0.25 | 0.06 | <0.06 |
| S. haemolyticus (Meth$^R$) | >32 | 32 | >32 | >32 | 32 | 8 |
| E. faecium ATCC 35667 | >32 | 2 | 2 | 4 | 2 | 2 |
| E. faecalis ATCC 29212 | >32 | 1 | 1 | 4 | 1 | 1 |
| E. coli ATCC 25922 | <1 | >32 | >32 | >32 | >32 | 16 |
| P. aeruginosa ATCC 27853 | 8–16 | >32 | >32 | >32 | >32 | >32 |

| Organism | Cefotax. | 81 | 82 | 83 | 84 | 85 | 86 |
|---|---|---|---|---|---|---|---|
| S. aureus ATCC 29213 | 2 | — | — | — | — | <0.25 | 1 |
| S. aureus ATCC 25923 | <1 | <0.25 | <0.25 | <0.25 | <0.25 | <0.25 | — |
| S. epidermidis ATCC 31432 | 2 | <0.25 | <0.25 | <0.25 | <0.25 | <0.25 | — |
| S. aureus Col (Meth$^R$)(lac$^-$) | >32 | 2 | 4 | 4 | 2 | 4 | 8 |
| S. aureus 76 (Meth$^R$)(lac$^+$) | >32 | 4 | 16 | 16 | 8 | 16 | 16 |
| S. aureus Col8A (Meth$^S$)(lac$^-$) | 2 | <0.25 | <0.25 | <0.25 | <0.25 | <0.25 | 1 |
| S. haemolyticus (Meth$^R$) | >32 | 16 | 32 | 32 | 8 | 16 | 16 |
| E. faecium ATCC 35667 | >32 | 1 | 4 | 2 | 1 | 2 | 2 |
| E. faecalis ATCC 29212 | >32 | 2 | 1 | 1 | 1 | 4 | 4 |
| E. coli ATCC 25922 | <1 | >32 | >32 | >32 | >32 | >32 | 2 |
| P. aeruginosa ATCC 27853 | 8–16 | >32 | >32 | >32 | >32 | >32 | 32 |

| Organism | Cefotax. | 87 | 88 | 89 | 90 | 91 | 92 |
|---|---|---|---|---|---|---|---|
| S. aureus ATCC 29213 | 2 | — | — | 0.5 | 1 | — | <0.25 |
| S. aureus ATCC 25923 | <1 | <0.25 | <0.25 | <0.25 | 0.5 | <0.25 | <0.25 |
| S. epidermidis ATCC 31432 | 2 | <0.25 | <0.25 | <0.25 | <0.25 | <0.25 | <0.25 |
| S. aureus Col (Meth$^R$)(lac$^-$) | >32 | 1 | 4 | 2 | 8 | 4 | 2 |
| S. aureus 76 (Meth$^R$)(lac$^+$) | >32 | 4 | 16 | 4 | 16 | 16 | 16 |
| S. aureus Col8A (Meth$^S$)(lac$^-$) | 2 | <0.25 | <0.25 | 0.5 | 1 | <0.25 | <0.25 |
| S. haemolyticus (Meth$^R$) | >32 | 16 | 16 | 8 | 32 | >32 | 8 |
| E. faecium ATCC 35667 | >32 | 1–2 | 2 | 4 | 16 | 2 | 16 |
| E. faecalis ATCC 29212 | >32 | 2 | 4 | 2 | 32 | 1 | 16 |
| E. coli ATCC 25922 | <1 | >32 | >32 | 2 | 4 | >32 | >32 |
| P. aeruginosa ATCC 27853 | 8–16 | >32 | >32 | 8 | 16 | >32 | >32 |

| Organism | Cefotax. | 93 | 94 | 95 | 96 | 97 | 98 |
|---|---|---|---|---|---|---|---|
| S. aureus ATCC 29213 | 2 | <0.25 | — | — | 0.25 | 0.06 | 0.5 |
| S. aureus ATCC 25923 | <1 | <0.25 | <0.25 | <0.25 | — | — | — |
| S. epidermidis ATCC 31432 | 2 | <0.25 | <0.25 | <0.25 | — | — | — |
| S. aureus Col (Meth$^R$)(lac$^-$) | >32 | 2 | 4 | 4 | 8 | 2 | 2 |
| S. aureus 76 (Meth$^R$)(lac$^+$) | >32 | 8 | 16 | 8 | 16 | 4 | 8 |
| S. aureus Col8A (Meth$^S$)(lac$^-$) | 2 | <0.25 | <0.25 | <0.25 | 0.5 | 0.125 | — |
| S. haemolyticus (Meth$^R$) | >32 | 8 | >32 | 16 | 16 | 8 | 8 |
| E. faecium ATCC 35667 | >32 | 0.5 | 2 | 4 | 4 | 1 | 4 |
| E. faecalis ATCC 29212 | >32 | <0.25 | 1 | 4 | 1 | 0.5 | 1 |
| E. coli ATCC 25922 | <1 | >32 | >32 | >32 | >32 | >32 | 8 |
| P. aeruginosa ATCC 27853 | 8–16 | >32 | >32 | >32 | >32 | >32 | 16 |

| Organism | Cefotax. | 99 | 100 | 101 | 102 | 103 | 104 |
|---|---|---|---|---|---|---|---|
| S. aureus ATCC 29213 | 2 | 0.125 | <0.06 | 0.25 | 0.125 | 0.25 | 0.5 |
| S. aureus ATCC 25923 | <1 | — | — | — | — | — | — |
| S. epidermidis ATCC 31432 | 2 | — | — | — | — | — | — |
| S. aureus Col (Meth$^R$)(lac$^-$) | >32 | 4 | 4 | 4 | 4 | 2 | 2 |
| S. aureus 76 (Meth$^R$)(lac$^+$) | >32 | 16 | 8 | 8 | 16 | 8 | 4 |
| S. aureus Col8A (Meth$^S$)(lac$^-$) | 2 | — | — | 0.25 | 0.125 | 0.25 | 0.5 |
| S. haemolyticus (Meth$^R$) | >32 | 16 | 16 | 16 | 32 | 4 | 4 |

TABLE 1-continued

| Organism | Cefotax. | | | | | | |
|---|---|---|---|---|---|---|---|
| E. faecium ATCC 35667 | >32 | 1 | 4 | 2 | 4 | 2 | 4 |
| E. faecalis ATCC 29212 | >32 | 1 | 1 | 1 | 2 | 1 | 2 |
| E. coli ATCC 25922 | <1 | >32 | >32 | >32 | 32 | >32 | 8 |
| P. aeruginosa ATCC 27853 | 8–16 | >32 | >32 | >32 | >32 | >32 | 16 |

| Organism | Cefotax. | 105 | 106 | 107 | 108 | 109 | 110 |
|---|---|---|---|---|---|---|---|
| S. aureus ATCC 29213 | 2 | 0.25 | 0.25 | 0.25 | 0.5 | 0.125 | 0.25 |
| S. aureus ATCC 25923 | <1 | — | — | — | — | — | — |
| S. epidermidis ATCC 31432 | 2 | — | — | — | — | — | — |
| S. aureus Col (Meth$^R$)(lac$^-$) | >32 | 4 | 1 | 4 | 4 | 4 | 2 |
| S. aureus 76 (Meth$^R$)(lac$^+$) | >32 | 16 | 8 | 16 | 8 | 16 | 8 |
| S. aureus Col8A (Meth$^S$)(lac$^-$) | 2 | 0.25 | 0.125 | 0.25 | 0.5 | 0.125 | 0.25 |
| S. haemolyticus (Meth$^R$) | >32 | 32 | 32 | 32 | 16 | 32 | >16 |
| E. faecium ATCC 35667 | >32 | 2 | 4 | 8 | 16 | 4 | 2 |
| E. faecalis ATCC 29212 | >32 | 1 | 4 | 8 | 16 | 4 | 2 |
| E. coli ATCC 25922 | <1 | >32 | >32 | >32 | 4 | >32 | >32 |
| P. aeruginosa ATCC 27853 | 8–16 | >32 | >32 | >32 | 16 | >32 | >32 |

| Organism | Cefotax. | 111 | 112 | 113 | 114 | 115 | 116 |
|---|---|---|---|---|---|---|---|
| S. aureus ATCC 29213 | 2 | 0.5 | <0.06 | 0.125 | 0.25 | 0.25 | 0.25 |
| S. aureus ATCC 25923 | <1 | — | — | — | — | — | — |
| S. epidermidis ATCC 31432 | 2 | — | — | — | — | — | — |
| S. aureus Col (Meth$^R$)(lac$^-$) | >32 | 8 | 4 | 4 | 4 | 4 | 4 |
| S. aureus 76 (Meth$^R$)(lac$^+$) | >32 | 16 | 16 | 16 | 16 | 8 | 16 |
| S. aureus Col8A (Meth$^S$)(lac$^-$) | 2 | 0.25 | <0.06 | 0.125 | 0.125 | 0.25 | 0.125 |
| S. haemolyticus (Meth$^R$) | >32 | 32 | 32 | >32 | 32 | 32 | 16 |
| E. faecium ATCC 35667 | >32 | 4 | 4 | 4 | 2 | 8 | 2 |
| E. faecalis ATCC 29212 | >32 | 4 | 4 | 1 | 1 | 4 | 2 |
| E. coli ATCC 25922 | <1 | >32 | >32 | >32 | >32 | >32 | >32 |
| P. aeruginosa ATCC 27853 | 8–16 | >32 | >32 | >32 | >32 | >32 | >32 |

| Organism | Cefotax. | 117 | 118 | 119 | 120 | 121 | 122 |
|---|---|---|---|---|---|---|---|
| S. aureus ATCC 29213 | 2 | 0.25 | 0.25 | 0.125 | 0.25 | 0.5 | 0.25 |
| S. aureus ATCC 25923 | <1 | — | — | — | — | — | — |
| S. epidermidis ATCC 31432 | 2 | — | — | — | — | — | — |
| S. aureus Col (Meth$^R$)(lac$^-$) | >32 | 8 | 4 | 2 | 8 | 4 | 4 |
| S. aureus 76 (Meth$^R$)(lac$^+$) | >32 | 16 | 8 | 8 | 16 | 8 | 8 |
| S. aureus Col8A (Meth$^S$)(lac$^-$) | 2 | 0.125 | 0.125 | 0.06 | 0.25 | 0.5 | 0.25 |
| S. haemolyticus (Meth$^R$) | >32 | 32 | 32 | 16 | 32 | 16 | 16 |
| E. faecium ATCC 35667 | >32 | 1 | 4 | 1 | 8 | 2 | 4 |
| E. faecalis ATCC 29212 | >32 | 2 | 4 | 1 | 4 | 0.5–1 | 4 |
| E. coli ATCC 25922 | <1 | >32 | >32 | >32 | >32 | >32 | >32 |
| P. aeruginosa ATCC 27853 | 8–16 | >32 | >32 | >32 | >32 | >32 | >32 |

| Organism | Cefotax. | 123 | 124 | 125 | 126 | 127 | 128 |
|---|---|---|---|---|---|---|---|
| S. aureus ATCC 29213 | 2 | 0.06 | 0.25 | 0.5 | 0.125 | ≦0.06 | ≦0.06 |
| S. aureus ATCC 25923 | <1 | — | — | — | — | — | — |
| S. epidermidis ATCC 31432 | 2 | — | — | — | — | — | — |
| S. aureus Col (Meth$^R$)(lac$^-$) | >32 | 4 | 4 | 4 | 8 | 4 | 8 |
| S. aureus 76 (Meth$^R$)(lac$^+$) | >32 | 8 | 16 | 8 | 16 | 8 | 16 |
| S. aureus Col8A (Meth$^S$)(lac$^-$) | 2 | ≦0.06 | 0.25 | 0.5 | 0.125 | ≦0.06 | ≦0.06 |
| S. haemolyticus (Meth$^R$) | >32 | 16 | 16 | 8 | — | — | — |
| E. faecium ATCC 35667 | >32 | 4 | 1 | 2 | 2 | 1 | 2 |
| E. faecalis ATCC 29212 | >32 | 2 | 1 | 0.25 | 1 | 1 | 2 |
| E. coli ATCC 25922 | <1 | >32 | >32 | >32 | >32 | >32 | >32 |
| P. aeruginosa ATCC 27853 | 8–16 | >32 | >32 | >32 | >32 | >32 | >32 |

| Organism | Cefotax. | 129 | 130 | 131 | 132 | 133 | 134 |
|---|---|---|---|---|---|---|---|
| S. aureus ATCC 29213 | 2 | ≦0.06 | 0.125 | ≦0.06 | 0.125 | 0.125 | 0.125 |
| S. aureus ATCC 25923 | <1 | — | — | — | — | — | — |
| S. epidermidis ATCC 31432 | 2 | — | — | — | — | — | — |
| S. aureus Col (Meth$^R$)(lac$^-$) | >32 | 8 | 2 | 1 | 8 | 2–4 | 2 |
| S. aureus 76 (Meth$^R$)(lac$^+$) | >32 | 8 | 4 | 4 | 32 | 8 | 8 |
| S. aureus Col8A (Meth$^S$)(lac$^-$) | 2 | ≦0.06 | 0.25 | ≦0.06 | 0.25 | 0.125 | 0.125 |
| S. haemolyticus (Meth$^R$) | >32 | 16 | 4 | 32 | >32 | 16 | 16 |
| E. faecium ATCC 35667 | >32 | — | 0.5 | 1 | 4 | 1 | 1 |
| E. faecalis ATCC 29212 | >32 | 0.25 | 0.25 | 0.5 | 4 | 1 | 0.5 |
| E. coli ATCC 25922 | <1 | 2 | >32 | >32 | >32 | >32 | >32 |
| P. aeruginosa ATCC 27853 | 8–16 | >32 | >32 | >32 | >32 | >32 | >32 |

| Organism | Cefotax. | 135 | 136 | 137 |
|---|---|---|---|---|
| S. aureus ATCC 29213 | 2 | 0.125 | 0.125 | 0.125 |
| S. aureus ATCC 25923 | <1 | — | — | — |

TABLE 1-continued

| | | | | |
|---|---|---|---|---|
| S. epidermidis ATCC 31432 | 2 | — | — | — |
| S. aureus Col (Meth$^R$)(lac$^-$) | >32 | 8 | 2 | 2 |
| S. aureus 76 (Meth$^R$)(lac$^+$) | >32 | 16 | 4 | 4 |
| S. aureus Col8A (Meth$^S$)(lac$^-$) | 2 | ≦0.06 | — | 0.06 |
| S. haemolyticus (Meth$^R$) | >32 | 32 | 4 | 16 |
| E. faecium ATCC 35667 | >32 | 2–4 | 1 | 0.25 |
| E. faecalis ATCC 29212 | >32 | 2–4 | 0.5 | 0.5 |
| E. coli ATCC 25922 | <1 | >32 | >32 | 4 |
| P. aeruginosa ATCC 27853 | 8–16 | >32 | >32 | >32 |

Test Compound Legend

| | |
|---|---|
| Cefotaxime | (7R)-3-Acetoxymethyl-7-[(Z)-2-(aminothiazol-4-yl)-2-(methoxyimino)acetamido]-3-cephem-4-carboxylic acid |
| Cmpd 1 | (7R)-7-[(Phenylacetyl)amino]-3-(p-fluorophenylthio)-3-cephem-4-carboxylic acid |
| Cmpd 2 | (7R)-7-[(Phenylacetyl)amino]-3-(m-iodophenylthio)-3-cephem-4-carboxylic acid |
| Cmpd 3 | (7R)-7-[(Phenylacetyl)amino]-3-(p-chlorophenylthio)-3-cephem-4-carboxylic acid |
| Cmpd 4 | (7R)-7-[(Phenylacetyl)amino]-3-(o-bromophenylthio)-3-cephem-4-carboxylic acid |
| Cmpd 5 | (7R)-7-[(Phenylacetyl)amino]-3-(p-bromophenylthio)-3-cephem-4-carboxylic acid |
| Cmpd 6 | (7R)-7-[(Phenylacetyl)amino]-3-(o-iodophenylthio)-3-cephem-4-carboxylic acid |
| Cmpd 7 | (7R)-7-[(Phenylacetyl)amino]-3-(dibenzofuranyl-3-thio)-3-cephem-4-carboxylic acid |
| Cmpd 8 | (7R)-7-[(Phenylacetyl)amino]-3-(4-biphenylthio)-3-cephem-4-carboxylic acid |
| Cmpd 9 | (7R)-7-((Phenylacetyl)amino]-3-(2-biphenylthio)-3-cephem-4-carboxylic acid |
| Cmpd 10 | (7R)-7-[(Phenylacetyl)amino]-3-(3-biphenylthio)-3-cephem-4-carboxylic acid |
| Cmpd 11 | (7R)-7-[(Phenylacetyl)amino]-3-(2-bromo-4-biphenylthio)-3-cephem-4-carboxylic acid |
| Cmpd 12 | (7R)-7-[(Phenylacetyl)amino]-3-(4-biphenylmethylthio)-3-cephem-4-carboxylic acid |
| Cmpd 13 | (7R)-7-[(Phenylacetyl)amino]-3-(2-fluoro-4-biphenylthio)-3-cephem-4-carboxylic acid |
| Cmpd 14 | (7R)-7-[(Phenylacetyl)amino]-3-(4-bromo-2-biphenylthio)-3-cephem-4-carboxylic acid |
| Cmpd 15 | (7R)-7-[(Phenylacetyl)amino]-3-(o-chlorophenylthio)-3-cephem-4-carboxylic acid |
| Cmpd 16 | (7R)-7-[(Phenylacetyl)amino]-3-(2,5-dichlorophenylthio)-3-cephem-4-carboxylic acid |
| Cmpd 17 | (7R)-7-[(Cyanoacetyl)amino]-3-(o-iodophenylthio)-3-cephem-4-carboxylic acid |
| Cmpd 18 | (7R)-7-[(Phenylacetyl)amino]-3-(3,4-dichlorophenylthio)-3-cephem-4-carboxylic acid |
| Cmpd 19 | (7R)-7-[(Phenylacetyl)amino]-3-(o-carbomethoxyphenylthio)-3-cephem-4-carboxylic acid |
| Cmpd 20 | (7R)-7-[(2-Thienylacetyl)amino]-3-(o-bromophenylthio)-3-cephem-4-carboxylic acid |
| Cmpd 21 | (7R)-7-[(Phenylacetyl)amino]-3-(dibenzofuranyl-1-thio)-3-cephem-4-carboxylic acid |
| Cmpd 22 | (7R)-7-[(Z)-2-(aminothiazol-4-yl)-2-(hydroxyimino)acetamido]-3-(o-iodophenylthio)-3-cephem-4-carboxylic acid |
| Cmpd 23 | (7R)-7-[(Phenylacetyl)amino]-3-(2-(4-cyanophenyl)phenylthio)-3-cephem-4-carboxylic acid |
| Cmpd 24 | (7R)-7-[(Phenylacetyl)amino]-3-(2,3-dichlorophenylthio)-3-cephem-4-carboxylic acid |
| Cmpd 25 | (7R)-7-[(2-Thienylacetyl)amino]-3-(o-iodophenylthio)-3-cephem-4-carboxylic acid |
| Cmpd 26 | (7R)-7-[(2-Thienylacetyl)amino]-3-(2,5-dichlorophenylthio)-3-cephem-4-carboxylic acid |
| Cmpd 27 | (7R)-7-[(Phenylacetyl)amino]-3-(2-(2-furyl)phenylthio)-3-cephem-4-carboxylic acid |
| Cmpd 28 | (7R)-7-[(Phenylacetyl)amino]-3-(2,4-dichlorophenylthio)-3-cephem-4-carboxylic acid |
| Cmpd 29 | (7R)-7-[(p-Methoxyphenylacetyl)amino]-3-(o-iodophenylthio)-3-cephem-4-carboxylic acid |
| Cmpd 30 | (7R)-7-[(p-Chlorophenoxyacetyl)amino]-3-(o-iodophenylthio)-3-cephem-4-carboxylic acid |
| Cmpd 31 | (7R)-7-[(p-Chlorophenoxyacetyl)amino]-3-(2,5-dichlorophenylthio)-3-cephem-4-carboxylic acid |
| Cmpd 32 | (7R)-7-[(p-Methoxyphenylacetyl)amino]-3-(2,5-dichlorophenylthio)-3-cephem-4-carboxylic acid |

TABLE 1-continued

| | |
|---|---|
| Cmpd 33 | (7R)-7-[(Phenylacetyl)amino]-3-(2-bromo-5-fluorophenylthio)-3-cephem-4-carboxylic acid |
| Cmpd 34 | (7R)-7-[(Cyanoacetyl)amino]-3-(2-biphenylthio)-3-cephem-4-carboxylic acid |
| Cmpd 35 | (7R)-7-[(Phenylthioacetyl)amino]-3-(2,5-dichlorophenylthio)-3-cephem-4-carboxylic acid |
| Cmpd 36 | (7R)-7-[(Phenylacetyl)amino]-3-(2-vinylphenylthio)-3-cephem-4-carboxylic acid |
| Cmpd 37 | (7R)-7-[(Phenylacetyl)amino]-3-(2-(2-thienyl)phenylthio)-3-cephem-4-carboxylic acid |
| Cmpd 38 | (7R)-7-[(Phenylacetyl)amino]-3-(2-hydroxymethylphenylthio)-3-cephem-4-carboxylic acid |
| Cmpd 39 | (7R)-7-[(Phenylacetyl)amino]-3-(2,4-dibromophenylthio)-3-cephem-4-carboxylic acid |
| Cmpd 40 | (7R)-7-[(Phenylacetyl)amino]-3-(4-trifluoromethylphenylthio)-3-cephem-4-carboxylic acid |
| Cmpd 41 | (7R)-7-[(Phenylacetyl)amino]-3-(2-cyanophenylthio)-3-cephem-4-carboxylic acid |
| Cmpd 42 | (7R)-7-[(Z)-2-(aminothiazol-4-yl)-2-(hydroxyimino)acetamido]-3-(2-biphenylthio)-3-cephem-4-carboxylic acid |
| Cmpd 43 | (7R)-7-[(Phenylacetyl)amino]-3-(2-(2-(4-methoxyphenylmethyl)thien-5-yl)phenylthio)-3-cephem-4-carboxylic acid |
| Cmpd 44 | (7R)-7-[(Phenylacetyl)amino]-3-(2-methylthiophenylthio)-3-cephem-4-carboxylic acid |
| Cmpd 45 | (7R)-7-[(Phenylacetyl)amino]-3-(2-(2-(N-methylimidazoliummethyl)thien-5-yl)phenylthio)-3-cephem-4-carboxylic acid |
| Cmpd 46 | (7R)-7-[(Phenylacetyl)amino]-3-(2-tert-butylphenylthio)-3-cephem-4-carboxylic acid |
| Cmpd 47 | (7R)-7-[(Phenylacetyl)amino]-3-(2-iso-propyloxyphenylthio)-3-cephem-4-carboxylic acid |
| Cmpd 48 | (7R)-7-[(Phenylacetyl)amino]-3-(2-(3-(N-methylimidazoliummethyl)furan-2-yl)phenylthio)-3-cephem-4-carboxylic acid |
| Cmpd 49 | (7R)-7-[(Phenylacetyl)amino]-3-(4-cyano-2-nitrophenylthio)-3-cephem-4-carboxylic acid |
| Cmpd 50 | (7R)-7-[(Phenylacetyl)amino]-3-(2-formylphenylthio)-3-cephem-4-carboxylic acid |
| Cmpd 51 | (7R)-7-[(Phenylacetyl)amino]-3-(2,4-dicyanophenylthio)-3-cephem-4-carboxylic acid |
| Cmpd 52 | (7R)-7-[(Cyanoacetyl)amino]-3-(2-cyanophenylthio)-3-cephem-4-carboxylic acid |
| Cmpd 53 | (7R)-7-[(Z)-2-(aminothiazol-4-yl)-2-(cyclopentyloxyimino)acetamido]-3-(2-cyanophenylthio)-3-cephem-4-carboxylic acid |
| Cmpd 54 | (7R)-7-[(Phenylacetyl)amino]-3-(1-naphthalenylthio)-3-cephem-4-carboxylic acid |
| Cmpd 55 | (7R)-7-[(Phenylacetyl)amino]-3-(2,3-dihydro-2,2-dimethylbenzofuran-7-yl)-3-cephem-4-carboxylic acid |
| Cmpd 56 | (7R)-7-[(Phenylacetyl)amino]-3-(5,6,7,8-tetrahydronaphthalen-1-ylthio)-3-cephem-4-carboxylic acid |
| Cmpd 57 | (7R)-7-[(Phenylacetyl)amino]-3-(1-bromo-naphthalen-2-ylthio)-3-cephem-4-carboxylic acid |
| Cmpd 58 | (7R)-7-[(Phenylacetyl)amino]-3-(4-isothiouroniummethyl-2-iodophenylthio)-3-cephem-4-carboxylic acid |
| Cmpd 59 | (7R)-7-[(Phenylacetyl)amino]-3-(4-(2-imidazolin-2-ylthiomethyl)-2-iodophenylthio)-3-cephem-4-carboxylic acid |
| Cmpd 60 | (7R)-7-[(Phenylacetyl)amino]-3-(4-(N-amidino)isothiouroniummethyl-2-iodophenylthio)-3-cephem-4-carboxylate, inner salt |
| Cmpd 61 | (7R)-7-[(Phenylacetyl)amino]-3-(4-(N-morpholinoethyl)isothiouroniummethyl-2-iodophenylthio)-3-cephem-4-carboxylate, inner salt |
| Cmpd 62 | (7R)-7-[(Phenylacetyl)amino]-3-(4-tetra-methylisothiouroniummethyl-2-iodophenylthio)-3-cephem-4-carboxylate, inner salt |
| Cmpd 63 | (7R)-7-[(Phenylacetyl)amino]-3-(4-isothiouroniummethylphenylthio)-3-cephem-4-carboxylate, inner salt |
| Cmpd 64 | (7R)-7-[(Phenylacetyl)amino]-3-(2-isothiouroniummethylphenylthio)-3-cephem-4-carboxylate, inner salt |
| Cmpd 65 | (7R)-7-[(Phenylacetyl)amino]-3-(4-(1,2,4-triazol-5-ylthiomethyl)phenylthio)-3-cephem-4-carboxylic acid |

TABLE 1-continued

| | |
|---|---|
| Cmpd 66 | (7R)-7-[(Cyanoacetyl)amino]-3-(4-isothiouroniummethyl-2-iodophenylthio)-3-cephem-4-carboxylate, inner salt |
| Cmpd 67 | (7R)-7-[(Phenylacetyl)amino]-3-(2-(1,2,4-triazol-5-ylthiomethyl)phenylthio)-3-cephem-4-carboxylic acid |
| Cmpd 68 | (7R)-7-[(Phenylacetyl)amino]-3-(2-(2-imidazolin-4-on-2-yl)thiomethyl)phenylthio)-3-cephem-4-carboxylic acid |
| Cmpd 69 | (7R)-7-[(Phenylacetyl)amino]-3-(2-tetramethylisothiouroniummethylphenylthio)-3-cephem-4-carboxylate, inner salt |
| Cmpd 70 | (7R)-7-[(Phenylacetyl)amino]-3-(2-(pyridin-4-yl)thiomethyl)phenylthio)-3-cephem-4-carboxylic acid |
| Cmpd 71 | (7R)-7-[(Phenylacetyl)amino]-3-(1-N-methyltetrazol-5-yl)thiomethyl)phenylthio)-3-cephem-4-carboxylic acid |
| Cmpd 72 | (7R)-7-[(Phenylacetyl)amino]-3-(2-(2-imidazolin-2-yl)thiomethyl)phenylthio)-3-cephem-4-carboxylic acid |
| Cmpd 73 | (7R)-7-[(Phenylacetyl)amino]-3-(2-(N-methylpyridin-4-ium)thiomethyl)phenylthio)-3-cephem-4-carboxylate, inner salt |
| Cmpd 74 | (7R)-7-[(Phenylacetyl)amino]-3-(2-N,N'-diethylisothiouroniummethylphenylthio)-3-cephem-4-carboxylate, inner salt |
| Cmpd 75 | (7R)-7-[(Phenylacetyl)amino]-3-(2-(pyrimidine-2-yl)thiomethyl)phenylthio)-3-cephem-4-carboxylic acid |
| Cmpd 76 | (7R)-7-[(Phenylacetyl)amino]-3-(2-N-methylisothiouroniummethylphenylthio)-3-cephem-4-carboxylate, inner salt |
| Cmpd 77 | (7R)-7-[(Phenylacetyl)amino]-3-(2-(2-methyl-1,3,4-thiadiazol-5-yl)thiomethyl)phenylthio)-3-cephem-4-carboxylic acid |
| Cmpd 78 | (7R)-7-[(Phenylacetyl)amino]-3-(2-N-acetylamidinothiomethylphenylthio)-3-cephem-4-carboxylic acid |
| Cmpd 79 | (7R)-7-[(Phenylacetyl)amino]-3-(2-N-cyclopropylisothiouroniummethylphenylthio)-3-cephem-4-carboxylate, inner salt |
| Cmpd 80 | (7R)-7-[(Phenylacetyl)amino]-3-(3-isothiouroniummethylphenylthio)-3-cephem-4-carboxylate, inner salt |
| Cmpd 81 | (7R)-7-[(Phenylacetyl)amino]-3-(2-phenylpyridin-3-ylthio)-3-cephem-4-carboxylic acid |
| Cmpd 82 | (7R)-7-[(Phenylacetyl)amino]-3-(2-phenyl-N-methylpyridin-3-iumthio)-3-cephem-4-carboxylate |
| Cmpd 83 | (7R)-7-[(Phenylacetyl)amino]-3-(2-phenyl-N-benzylpyridin-3-iumthio)-3-cephem-4-carboxylate |
| Cmpd 84 | (7R)-7-[(4-Chlorophenylacetyl)amino]-3-(2-phenylpyridin-3-ylthio)-3-cephem-4-carboxylic acid |
| Cmpd 85 | (7R)-7-[(Cyanoacetyl)amino]-3-(2-phenylpyridin-3-ylthio)-3-cephem-4-carboxylic acid |
| Cmpd 86 | (7R)-7-[(Z)-2-(aminothiazol-4-yl)-2-(cyclopentyloxyimino)acetamido]-3-(2-phenylpyridin-3-ylthio)-3-cephem-4-carboxylic acid |
| Cmpd 87 | (7R)-7-[(Phenylacetyl)amino]-3-(1-N-phenylpyrazol-5-ylthio)-3-cephem-4-carboxylic acid |
| Cmpd 88 | (7R)-7-[(Cyanoacetyl)amino]-3-(1-N-phenylpyrazol-5-ylthio)-3-cephem-4-carboxylic acid |
| Cmpd 89 | (7R)-7-[(Z)-2-(aminothiazol-4-yl)-2-(cyclopentyloxyimino)acetamido]-3-(1-N-phenylpyrazol-5-ylthio)-3-cephem-4-carboxylic acid |
| Cmpd 90 | (7R)-7-[(Z)-2-(aminothiazol-4-yl)-2-(2-fluoroethyloxyimino)acetamido]-3-(1-N-phenylpyrazol-5-ylthio)-3-cephem-4-carboxylic acid |
| Cmpd 91 | (7R)-7-[(Phenylacetyl)amino]-3-(1-N-phenyl-1,2,3-triazol-5-ylthio)-3-cephem-4-carboxylic acid |
| Cmpd 92 | (7R)-7-[(Phenylacetyl)amino]-3-(2-amino-4-phenyl-thiazol-5-ylthio)-3-cephem-4-carboxylic acid |
| Cmpd 93 | (7R)-7-[(Phenylacetyl)amino]-3-(4-phenyl-1,2,3-thiadiazol-5-ylthio)-3-cephem-4-carboxylic acid |
| Cmpd 94 | (7R)-7-[(Phenylacetyl)amino]-3-(1-N-phenyltetrazol-5-ylthio)-3-cephem-4-carboxylic acid |
| Cmpd 95 | (7R)-7-[(Phenylacetyl)amino]-3-(2-oxazol-5-ylphenylthio)-3-cephem-4-carboxylic acid |
| Cmpd 96 | (7R)-7-[((2-aminomethylphenyl)acetyl)amino]-3-(1-N-phenylpyrazol-5-ylthio)-3-cephem-4-carboxylic acid |
| Cmpd 97 | (7R)-7-[((4-isothiouroniummethylphenyl)acetyl)amino]-3-(2-isothiouroniummethylphenylthio)-3-cephem-4-carboxylate, trifluoroacetic acid salt |

TABLE 1-continued

| | |
|---|---|
| Cmpd 98 | (7R)-7-[(Z)-2-(2-amino-5-chlorothiazol-4-yl)-2-(2-fluoroethyloxyimino)acetamido]-3-(1-N-phenylpyrazol-5-ylthio)-3-cephem-4-carboxylic acid |
| Cmpd 99 | (7R)-7-[((4-Hydroxyphenyl)acetyl)amino]-3-(2-isothiouroniummethylphenylthio)-3-cephem-4-carboxylic acid, inner salt |
| Cmpd 100 | (7R)-7-[(Phenylacetyl)amino]-3-(2-(2-isothiouronium)ethylphenylthio)-3-cephem-4-carboxylate, inner salt |
| Cmpd 101 | (7R)-7-[((2-Aminomethylphenyl)acetyl)amino]-3-(2-isothiouroniummethylphenylthio)-3-cephem-4-carboxylate, trifluoroacetic acid salt |
| Cmpd 102 | (7R)-7-[(Phenylacetyl)amino]-3-(2-cyanopyridin-3-ylthio)-3-cephem-4-carboxylic acid |
| Cmpd 103 | (7R)-7-[(Phenylacetyl)amino]-3-(2-(pyrazol-1-yl)pyridin-3-ylthio)-3-cephem-4-carboxylic acid |
| Cmpd 104 | (7R)-7-[(Z)-2-(aminothiazol-4-yl)-2-(3-pentyloxyimino)acetamido]-3-(1-N-phenylpyrazol-5-ylthio)-3-cephem-4-carboxylic acid |
| Cmpd 105 | (7R)-7-[(Phenylacetyl)amino]-3-(1-N-(pyridin-2-yl)pyrazol-5-ylthio)-3-cephem-4-carboxylic acid |
| Cmpd 106 | (7R)-7-[(methylthioacetyl)amino]-3-(1-N-phenylpyrazol-5-ylthio)-3-cephem-4-carboxylic acid |
| Cmpd 107 | (7R)-7-[(cyclopropylacetyl)amino]-3-(1-N-phenylpyrazol-5-ylthio)-3-cephem-4-carboxylic acid |
| Cmpd 108 | (7R)-7-[(Z)-2-(2-aminothiazol-4-yl)-2-(cyclopropylmethyloxyimino)acetamido]-3-(1-N-phenylpyrazol-5-ylthio)-3-cephem-4-carboxylic acid |
| Cmpd 109 | (7R)-7-[(hexanoyl)amino]-3-(1-N-phenylpyrazol-5-ylthio)-3-cephem-4-carboxylic acid |
| Cmpd 110 | (7R)-7-[(4-pyridylthioacetyl)amino]-3-(1-N-phenylpyrazol-5-ylthio)-3-cephem-4-carboxylic acid |
| Cmpd 111 | (7R)-7-[(2-furylacetyl)amino]-3-(1-N-phenylpyrazol-5-ylthio)-3-cephem-4-carboxylic acid |
| Cmpd 112 | (7R)-7-[(phenyloxyacetyl)amino]-3-(1-N-phenylpyrazol-5-ylthio) -3-cephem-4-carboxylic acid |
| Cmpd 113 | (7R)-7-[(Phenylacetyl)amino]-3-(1-N-(3-nitrophenyl)pyrazol-5-ylthio)-3-cephem-4-carboxylic acid |
| Cmpd 114 | (7R)-7-[(Phenylacetyl)amino]-3-(1-N-(4-methoxyphenyl)pyrazol-5-ylthio)-3-cephem-4-carboxylic acid |
| Cmpd 115 | (7R)-7-[(2-dithiolanylcarbonyl)amino]-3-(1-N-phenylpyrazol-5-ylthio)-3-cephem-4-carboxylic acid |
| Cmpd 116 | (7R)-7-[(2-thienylacetyl)amino]-3-(1-N-phenylpyrazol-5-ylthio)-3-cephem-4-carboxylic acid |
| Cmpd 117 | (7R)-7-[(Phenylacetyl)amino]-3-(1-N-(3-methoxyphenyl)pyrazol-5-ylthio)-3-cephem-4-carboxylic acid |
| Cmpd 118 | (7R)-7-[(2-methyl-1,3,4-thiadiazol-5-ylthio)acetyl)amino]-3-(1-N-phenylpyrazol-5-ylthio)-3-cephem-4-carboxylic acid |
| Cmpd 119 | (7R)-7-[(phenylthioacetyl)amino]-3-(1-N-phenylpyrazol-5-ylthio)-3-cephem-4-carboxylic acid |
| Cmpd 120 | (7R)-7-[(2-amino-1,3,4-thiadiazol-5-ylthio)acetyl)amino]-3-(1-N-phenylpyrazol-5-ylthio)-3-cephem-4-carboxylic acid |
| Cmpd 121 | (7R)-7-[2-(2-furyl)-2-(hydroxyimino)acetamido]-3-(1-N-phenylpyrazol-5-ylthio)-3-cephem-4-carboxylic acid |
| Cmpd 122 | (7R)-7-[(cyanomethylthioacetyl)amino]-3-(1-N-phenylpyrazol-5-ylthio)-3-cephem-4-carboxylic acid |
| Cmpd 123 | (7R)-7-[(Phenylacetyl)amino]-3-(1-N-(4-fluorophenyl)pyrazol-5-ylthio)-3-cephem-4-carboxylic acid |
| Cmpd 124 | (7R)-7-[((4-aminomethylphenyl)acetyl)amino]-3-(2-isothiouroniummethylphenylthio)-3-cephem-4-carboxylate, trifluoroacetic acid salt |
| Cmpd 125 | (7R)-7-[((N,N'-diisopropylisothiouronium)acetyl)amino]-3-(2-isothiouroniummethylphenylthio)-3-cephem-4-carboxylate, trifluoroacetic acid salt |
| Cmpd 126 | (7R)-7-[(methylthioacetyl)amino]-3-(2-(N-amidino)isothiouroniummethylphenylthio)-3-cephem-4-carboxylate, inner salt |
| Cmpd 127 | (7R)-7-[(methylthioacetyl)amino]-3-(2-isothiouroniummethylphenylthio)-3-cephem-4-carboxylate, inner salt |
| Cmpd 128 | (7R)-7-[(Phenylacetyl)amino]-3-(2-guanidiniummethylphenylthio)-3-cephem-4-carboxylate, inner salt |

TABLE 1-continued

| | |
|---|---|
| Cmpd 129 | (7R)-7-[(Z)-2-(Aminothiazol-4-yl)-2-(hydroxyimino)acetamido]-3-(2-isothiouroniummethylphenylthio)-3-cephem-4-carboxylate, inner salt |
| Cmpd 130 | (7R)-7-[(Z)-2-(Phenyl)-2-(hydroxyimino)acetamido]-3-(1-N-(phenyl)pyrazol-5-ylthio)-3-cephem-4-carboxylic acid |
| Cmpd 131 | (7R)-7-[((Z-2-Chlorovinyl)thioacetyl)amino]-3-(1-N-phenylpyrazol-5-ylthio)-3-cephem-4-carboxylic acid |
| Cmpd 132 | (7R)-7-[(Phenylacetyl)amino]-3-(2-(pyrazol-1-yl)phenylthio)-3-cephem-4-carboxylic acid |
| Cmpd 133 | (7R)-7-[(methylthioacetyl)amino]-3-(2-(N-amino)isothiouroniummethylphenylthio)-3-cephem-4-carboxylate, inner salt |
| Cmpd 134 | (7R)-7-[(3-iodoprop-1-ylthioacetyl)amino]-3-(2-isothiouroniummethylphenylthio)-3-cephem-4-carboxylate, inner salt |
| Cmpd 135 | (7R)-7-[(Methylthioacetyl)amino]-3-(2-guanidiniummethylphenylthio)-3-cephem-4-carboxylate, inner salt |
| Cmpd 136 | (7R)-7-[(Z)-2-(Phenyl)-2-(hydroxyimino)acetamido]-3-(2-isothiouroniummethylphenylthio)-3-cephem-4-carboxylate, inner salt |
| Cmpd 137 | (7R)-7-[((2-guanidinoethylthio)acetyl)amino]-3-(2-isothiouroniummethylphenylthio)-3-cephem-4-carboxylate, trifluoroacetic acid salt |

In Vivo Antibacterial Evaluation

Compounds with superior activity in vitro when compared to reference antibiotics, are further evaluated in a murine model for lethal bacteremic peritonitis.

Groups of 5 female Swiss-Webster mice (Simonsen, Gilroy, Calif.) each are challenged by the intraperitoneal (IP) route with ten-fold increments of a bacterial inoculum. This permits calculation of the mean lethal dose ($LD_{50}$) and the $LD_{100}$. For preliminary evaluation of a new antibiotic, mice are challenged IP with an $LD_{100}$ titer of bacteria. In two equal doses administered at the time of bacterial challenge and 2 hours later, groups of 10 mice each are treated subcutaneously with two-fold increments of the test drug and an antibiotic of known efficacy in mice and humans (i.e., positive control). Mice are observed for 72 h. Those alive at 72 h are considered long term survivors. The total drug dose in mg/kg that protects 50% of mice in a group from death is termed the mean protective dose ($PD_{50}$). $PD_{50}$s are similarly determined for several pathogens. The quantitative endpoints for the new drug are then compared with those obtained with reference antibiotics.

Six ten-fold dilutions of inoculum suspended in 0.5 mL of sterilized 7% hog gastric mucin (Sigma) are injected IP in groups of 5 mice each. A control group of 5 mice receive mucin alone. Mice are observed for 72 h. Those alive at 72 h are considered long term survivors. The mean lethal dose ($LD_{50}$) and 100% lethal dose ($LD_{100}$) are determined by the probit test.

For antibiotic efficacy studies, mice are challenged IP with bacterial titers that will afford an $LD_{100}$ for the test strain. In two equal doses administered at the time of bacterial challenge and 2 hours later, groups of 10 mice each are treated by the subcutaneous route (SC) with twofold increments of the test antibiotic; another group is treated similarly with a reference antibiotic of known efficacy in animals and man. Drug doses can range from 0.01 to 512 mg/kg. If the drug is poorly soluble, Tween 20 or propylene glycol will be employed to solubilize the drug. Animals are observed for 72 h. The 50% protective dose ($PD_{50}$) is calculated in mg/kg by the probit method. The $PD_{50}$ is the same as the 50% effective dose ($ED_{50}$) and the 50% curative dose ($CD_{50}$). Samples of blood from the hearts of all animals that die and from half the mice that survive are cultured on brain-heart infusion agar. Animals that received a protective dosage of the test drug will be alive at 72 h, although they may appear moderately ill to very ill during the observation period. Infected, placebo-treated control mice and those receiving non-effective i.e. lower dosages of the test drug will demonstrate a high rate of mortality. Most of these mice will die within 6 to 48 h. Those alive at 72 h will be considered long term survivors.

| | Mortality Compound: | | | | |
|---|---|---|---|---|---|
| | Vancomycin | 6 | 17 | 81 | 87 |
| Dose | | | | | |
| 16 mg/kg | 0/10 | 0/10 | 0/10 | 2/10 | 0/10 |
| 8 mg/kg | 0/10 | 1/10 | 0/10 | 5/10 | 0/10 |
| 4 mg/kg | 2/10 | 5/10 | 5/10 | 10/10 | 3/10 |
| 2 mg/kg | 8/10 | 8/10 | 8/10 | 8/10 | 4/10 |
| $ED_{50}$ (mg/kg) | 2.81 | 3.65 | 3.41 | 8.46 | 1.89 |
| Challenge str MIC (µg/ml) | 1 | <0.5 | 0.125 | 0.125 | 0.06 |

-continued

| | Mortality Compound: | | | | |
|---|---|---|---|---|---|
| | Vancomycin | Cefotaxime | 6 | 41 | 88 |
| Dose | | | | | |
| 40 mg/kg | | 1/10 | | | |
| 20 mg/kg | | 4/10 | | | |
| 10 mg/kg | 2/10 | 3/10 | 1/10 | 0/10 | 0/10 |
| 5 mg/kg | 5/10 | 5/10 | 1/10 | 0/10 | 0/10 |
| 2.5 mg/kg | 5/10 | 8/10 | 4/10 | 0/10 | 0/10 |
| 1.25 mg/kg | 6/10 | | 4/10 | 6/10 | 1/10 |
| 0.625 mg/kg | 8/10 | | 9/10 | 8/10 | 2/10 |
| 0.3125 mg/kg | | | | | |
| $ED_{50}$ (mg/kg) | 2.79 | 7.47 | 1.57 | 1.13 | 0.31 |
| 95% conf. interval | 0.79–4.80 | 2.91–12.04 | 0.83–2.31 | 0.81–1.45 | 0.12–0.74 |
| Challenge str MIC (μg/ml) | 1 | 2 | 0.03 | 0.06 | 0.25 |

| | Mortality Compound: | | | | |
|---|---|---|---|---|---|
| | 89 | 97 | 101 | 103 | 104 |
| Dose | | | | | |
| 40 mg/kg | | | | | |
| 20 mg/kg | | | | | |
| 10 mg/kg | 8/10 | | 0/10 | 0/10 | 9/10 |
| 5 mg/kg | 8/10 | 0/10 | 0/10 | 5/10 | 8/10 |
| 2.5 mg/kg | 9/10 | 2/10 | 0/10 | 7/10 | 8/10 |
| 1.25 mg/kg | 9/10 | 3/10 | 2/10 | 7/10 | 10/10 |
| 0.625 mg/kg | 9/10 | 5/10 | 5/10 | 7/10 | 6/10 |
| 0.3125 mg/kg | | 8/10 | | | |
| $ED_{50}$ (mg/kg) | >10 | 0.74 | 0.65 | 2.67 | >10 |
| 95% conf. interval | — | 0.39–1.08 | 0.36–0.94 | 1.13–4.21 | — |
| Challenge str MIC (μg/ml) | 0.5 | 0.062 | 0.125 | 0.125 | 0.5 |

| | Mortality Compound: | | | | |
|---|---|---|---|---|---|
| | 102 | 106 | 115 | 108 | 110 |
| Dose | | | | | |
| 40 mg/kg | | | | | |
| 20 mg/kg | | | | | |
| 10 mg/kg | | | 0/10 | 10/10 | 0/10 |
| 5 mg/kg | 0/10 | | 4/10 | 10/10 | 6/10 |
| 2.5 mg/kg | 5/10 | 1/10 | 7/10 | 9/10 | 8/10 |
| 1.25 mg/kg | 7/10 | 2/10 | 9/10 | 8/10 | 7/10 |
| 0.625 mg/kg | 8/10 | 6/10 | 8/10 | 9/10 | 8/10 |
| 0.3125 mg/kg | 10/10 | 9/10 | | | |
| 0.1562 mg/kg | | 9/10 | | | |
| $ED_{50}$ (mg/kg) | 1.75 | 0.72 | 3.04 | >10 | 3.45 |
| 95% conf. interval | 1.12–2.38 | 0.44–1.00 | 1.73–4.34 | — | 1.58–5.32 |
| Challenge str MIC (μg/ml) | 0.125 | 0.125 | 0.25 | 0.5 | 0.25 |

| | Mortality Compound: | | | | |
|---|---|---|---|---|---|
| | 107 | 118 | 119 | 122 | 125 |
| Dose | | | | | |
| 40 mg/kg | | | | | |
| 20 mg/kg | | | | | |
| 10 mg/kg | 0/10 | 2/10 | | 0/10 | 7/10 |
| 5 mg/kg | 0/10 | 4/10 | 8/10 | 0/10 | 4/9 |
| 2.5 mg/kg | 5/10 | 8/10 | 7/10 | 0/10 | 7/10 |
| 1.25 mg/kg | 6/10 | 6/10 | 10/10 | 6/10 | 10/10 |
| 0.625 mg/kg | 8/10 | 8/10 | 9/10 | 8/10 | 9/10 |
| 0.3125 mg/kg | | | 10/10 | | |
| 0.1562 mg/kg | | | | | |

-continued

| | | | | | |
|---|---|---|---|---|---|
| ED$_{50}$ (mg/kg) | 1.58 | 3.38 | >5 | 1.13 | >10 |
| 95% conf. interval | 0.99–2.17 | 1.10–5.66 | — | 0.81–1.45 | — |
| Challenge str MIC (µg/ml) | 0.125 | 0.06 | 0.25 | 0.125 | — |

| | Mortality Compound: | | | |
|---|---|---|---|---|
| | 127 | 130 | 131 | 137 |
| Dose | | | | |
| 40 mg/kg | | | | |
| 20 mg/kg | | | | |
| 10 mg/kg | | 6/10 | 0/10 | |
| 5 mg/kg | 1/10 | 6/10 | 0/10 | |
| 2.5 mg/kg | 2/10 | 9/10 | 4/10 | |
| 1.25 mg/kg | 4/10 | 7/10 | 7/10 | |
| 0.625 mg/kg | 5/10 | 10/10 | 9/10 | 6/10 |
| 0.3125 mg/kg | 6/10 | | | 5/10 |
| 0.1562 mg/kg | | | | 7/10 |
| 0.0781 mg/kg | | | | 9/10 |
| 0.0391 mg/kg | | | | 8/10 |
| ED$_{50}$ (mg/kg) | 0.59 | >10 | 1.73 | 0.75 |
| 95% conf. interval | 0.11–1.07 | — | 1.18–2.27 | 0–1.75 |
| Challenge str MIC (µg/ml) | — | 0.125 | 0.06 | 0.06 |

(Compound numbers correspond to those in MIC tables;
data reported for challenge with methicillin-susceptible *S. aureus* strain ATCC 13709.)
(Compound numbers correspond to those in MIC tables)

EXAMPLES

The present invention will be more fully described in conjunction with the following specific examples which are not to be construed in any way as limiting the scope of the invention.

Example 1

(7R)-7-[(phenylacetyl)amino]-3-(4-biphenylthio)-3-cephem-4-carboxylate, benzhydryl ester To a stirred solution of (7R)-7-[(phenylacetyl)amino]-3-trifluoromethanesulfonyloxy-3-cephem-4-carboxylate, benzhydryl ester (760 mg, 1.2 mmol) in dry DMF (12 mL) at −60° under nitrogen was added a solution of sodium 4-phenylbenzenethiolate in DMF (3 mL), prepared from 4-phenylbenzenethiol (320 mg, 1.56 mmol) and sodium hexamethyldisilazide (1.2 mL of a 1M solution in THF, 1.2 mmol). After 25 min. the reaction was quenched by addition of aqueous 10% ammonium chloride solution (1 mL) and water (120 mL). The resulting milky solution was extracted with dichloromethane (3×50 mL) and 10% EtOAc/hexane (3×50 mL). The organic extracts were dried over sodium sulfate and filtered, and the solvent was removed with a rotary evaporator. The crude product was purified by chromatography on silica gel (chromatotron, 4 mm plate, 5% EtOAc/hexane, then 0.25% MeOH/dichloromethane) to afford 450 mg (56%) of the title compound. $^1$H NMR (CDCl$_3$) δ3.17 (d, 1H, J=18), 3.31 (d, 1H, J=17), 3.63 (d, 1H, J=16), 3.69 (d, 1H, J=16), 5.01 (d, 1H, J=4), 5.79 (dd, 1H, J=4,9), 6.06 (d, 1H, J=9), 7.00 (s, 1H), 7.2–7.7 (m, 25H).

Example 2

(7R)-7-[(phenylacetyl)amino]-3-(4-bromophenylthio)-3-cephem-4-carboxylate, benzhydryl ester To a well-stirred suspension of (7R)-7[(phenylacetyl)amino]-3-trifluoromethanesulfonyloxy-3-cephem-4-carboxylate, benzhydryl ester (190 mg, 0.30 mmol) in dry THF (20 mL) at −78° under nitrogen was added a suspension of sodium 4-bromobenzenethiolate in THF (5 mL), prepared from 4-phenylbenzenethiol (62 mg, 0.33 mmol) and sodium hexamethyldisilazide (0.30 mL of a 1M solution in THF, 0.30 mmol). After 1 h, the reaction was quenched by addition of aqueous 5% ammonium chloride solution (3 mL). The resulting mixture was extracted with dichloromethane (3×25 mL), and the extracts were washed with water and saturated sodium chloride solution. The organic phase was dried over sodium sulfate and filtered, and the solvent was removed with a rotary evaporator. The crude product-was purified by chromatography on silica gel (chromatotron, 2 mm plate, 0.25% MeOH/dichloromethane) to afford 85 mg (42%) of the title compound. $^1$H NMR (CDCl$_3$) δ3.10 (d, 1H, J=18), 3.28 (d, 1H, J=17), 3.63 (d, 1H, J=16), 3.69 (d, 1H, J=16), 5.00 (d, 1H, J=4), 5.81 (dd, 1H, J=4,9), 6.07 (d, 1H, J=9), 6.98 (s, 1H), 7.2–7.5 (m, 20H).

Substantially following the methods described in Examples 1–2, the compounds of the invention listed below in Examples 3–14 were obtained.

Example 3

(7R )-7-[(phenylacetyl)amino]-3-(4-iodophenylthio)-3-cephem-4-carboxylate, benzhydryl ester This was prepared by a procedure similar to that for Example 1, but sodium 4-iodo-phenylthiolate was used.

Example 4

(7R)-7-[(phenylacetyl)amino]-3-[2-bromo-4-(phenyl)phenylthio]-3-cephem-4-carboxylate, benzhydryl ester This was prepared by a procedure similar to that for Example 1, but sodium 2-bromo-4-(phenyl)phenylthiolate was used.

Example 5

(7R)-7-[(phenylacetyl)amino]-3-[2-phenyl-4-bromophenylthio]-3-cephem-4-carboxylate, benzhydryl ester This was prepared by a procedure similar to that for Example 1, but sodium 2-phenyl-4-bromophenylthiolate was used.

Example 6

(7R)-7-[(phenylacetyl)amino]-3-(3-iodophenylthio)-3-cephem-4-carboxylate, benzhydryl ester This was prepared by a procedure similar to that for Example 1, but sodium 3-iodo-phenylthiolate was used.

Example 7

(7R)-7-[(phenylacetyl)amino]-3-(2,4dichlorophenylthio)-3-cephem-4-carboxylate, benzhydryl ester This was prepared by a procedure similar to that for Example 1, but sodium 2,4-dichlorophenylthiolate was used.

Example 8

(7R)-7-[(phenylacetyl)amino]-3-[4-(2-imidazolyl)phenylthio]-3-cephem-4-carboxylate, benzhydryl ester This was prepared by a procedure similar to that for Example 1, but sodium 4-(2-imidazolyl)phenylthiolate was used.

Example 9

(7R)-7-[(phenylacetyl)amino]-3-(dibenzofuran-3-ylthio)-3-cephem-4-carboxylate, benzhydryl ester This was prepared by a procedure similar to that for Example 1, but sodium dibenzofuran-3-thiolate was used.

Example 10

(7R)-[(phenylacetyl)amino]-3-(dibenzofuranyl-2-ylthio)-3-cephem-4-carboxylate, benzhydryl ester This was prepared by a procedure similar to that for Example 1, but sodium dibenzofuran-2-thiolate was used.

Example 11

(7R)-7-[(phenylacetyl)amino]-3-(dibenzofuran-1-ylthio)-3-cephem-4-carboxylate, benzhydryl ester This was prepared by a procedure similar to that for Example 1, but sodium dibenzofuran-1-thiolate was used.

Example 12

(7R)-7-[(phenylacetyl)amino]-3-(dibenzofuran-4-ylthio)-3-cephem-4-carboxylate, benzhydryl ester This was prepared by a procedure similar to that for Example 1, but sodium dibenzofuran-4-thiolate was used.

Example 13

(7R)-7-[(phenylacetyl)amino]-3-[6-(hydroxymethyl)dibenzofuran-3-ylthio]-3-cephem-4-carboxylate, benzhydryl ester This was prepared by a procedure similar to that for Example 1, but sodium 6-(hydroxymethyl)dibenzofuran-3-thiolate was used.

Example 14

(7R)-7-[(phenylacetyl)amino]-3-[7-(hydroxymethyl)dibenzofuran-3-ylthio]-3-cephem-4-carboxylate, benzhydryl ester This was prepared by a procedure similar to that for Example 1, but sodium 7-(hydroxymethyl)dibenzofuran-3-thiolate was used.

Example 15

(7R)-7-[(phenylacetyl)amino]-3-(2-biphenylthio)-3-cephem-4-carboxylate, 4-methoxybenzyl ester To a stirred solution of (7R)-7-[(phenylacetyl)amino]-3-trifluoromethanesulfonyloxy-3-cephem-4-carboxylate, 4-methoxybenzyl ester (700 mg, 1.2 mmol) in dry DMF (12 mL) at −60° under nitrogen was added a solution of sodium 2-phenylbenzenethiolate in DMF (3 mL), prepared from 2-phenylbenzenethiol (320 mg, 1.56 mmol) and sodium hexamethyldisilazide (1.2 mL of a 1M solution in THF, 1.2 mmol). After 25 min. the reaction was quenched by addition of aqueous 10% ammonium chloride solution (1 mL) and water (120 mL). The resulting milky solution was extracted with dichloromethane (3×50 mL) and 10% EtOAc/hexane (3×50 mL). The organic extracts were dried over sodium sulfate and filtered, and the solvent was removed with a rotary evaporator. The crude product was purified by chromatography on silica gel (chroma-totron, 4 mm plate, 5% EtOAc/hexane, then 0.25% MeOH/dichloromethane) to afford 450 mg (56%) of the title compound.

Substantially following the methods described in Example 15, the compounds of the invention listed below in Examples 16–32 were obtained.

Example 16

(7R)-7-[(phenylacetyl)amino]-3-[2-(4-cyanophenyl)phenylthio]-3-cephem-4-carboxylate, 4-methoxybenzyl ester This was prepared by a procedure similar to that for Example 15, but sodium 2-(4-cyanophenyl)phenylthiolate was used.

Example 17

(7R)-7-[(phenylacetyl)amino]-3-[2,3-dichlorophenylthio]-3-cephem-4-methoxybenzyl ester This was prepared by a procedure similar to that for Example 15, but sodium 2,3-dichlorophenylthiolate was used.

Example 18

(7R)-7-[(phenylacetyl)amino]-3-[2,5-dichlorophenylthio]-3-cephem-4-carboxylate, 4-methoxybenzyl ester This was prepared by a procedure similar to that for Example 15, but sodium 2,5-dichlorophenylthiolate was used.

Example 19

(7R)-7-[(phenylacetyl)amino]-3-(2-bromo-5-fluorophenylthio)-3-cephem-4-carboxylate, methoxybenzyl ester This was prepared by a procedure similar to that for Example 15, but sodium 2-bromo-5-fluorophenylthiolate was used.

Example 20

(7R)-7-[(phenylacetyl)amino]-3-(2-bromolohenylthio)-3-cephem-4-carboxylate, 4-methoxybenzyl ester This was prepared by a procedure similar to that for Example 15, but sodium 2-bromophenylthiolate was used.

Example 21

(7R)-7-[(phenylacetyl)amino]-3-(4-chlorophenylthio)-3-cephem-4-carboxylate, 4-methoxybenzyl ester This was prepared by a procedure similar to that for Example 15, but sodium 4-chlorophenylthiolate was used.

EXAMPLE 22

(7R)-7-[(phenylacetyl)amino]-3-[4-(ethoxycarbonyl)phenylthio]-3-cephem-4-carboxylate, 4-methoxybenzyl ester This was prepared by a procedure similar to that for Example 15, but sodium 4-(ethoxycarbonyl)phenyl thiolate was used.

Example 23

(7R)-7-[(phenylacetyl)amino]-3-[2-(ethoxycarbonyl)phenylthio]-3-cephem-4-carboxylate, 4-methoxybenzyl ester This was prepared by a procedure similar to that for Example 15, but sodium 2-(ethoxycarbonyl)phenyl thiolate was used.

Example 24

(7R)-7-[(phenylacetyl)amino]-3-[2-iodophenylthio]-3-cephem-4-carboxylate, 4-methoxybenzyl ester This was prepared by a procedure similar to that for Example 15, but sodium 2-iodophenyl thiolate was used.

Example 25

(7R)-7-[(phenylacetyl)amino]-3-(2-chlorophenylthio)-3-cephem-4-carboxylate, 4-methoxybenzyl ester This was prepared by a procedure similar to that for Example 15, but sodium 2-chlorophenyl thiolate was used.

Example 26

(7R)-7-[(phenylacetyl)amino]-3-[4-bromo-3-(trifluoromethoxy)-phenylthio]-3-cephem-4-carboxylate, 4-methoxybenzyl ester This was prepared by a procedure similar to that for Example 15, but sodium 4-bromo-3-(trifluoromethoxy)phenyl thiolate was used.

Example 27

(7R)-7-[(phenylacetyl)amino]-3-[[4-(2-imidazolyl)methyl]phenyl-thio]-3-cephem-4-carboxylate, 4-methoxybenzyl ester This was prepared by a procedure similar to that for Example 15, but potassium 4-[(2-imidazolyl)methyl]phenyl thiolate was used.

Example 28

(7R)-7-[(phenylacetyl)amino]-3-[[4-(1-methyl-2-imidazolyl)methyl]-phenylthio]-3-cephem-4-carboxylate, 4-methoxybenzyl ester This was prepared by a procedure similar to that for Example 15, but potassium 4-[(1-methyl-2-imidazolyl)methyl]phenyl thiolate was used.

Example 29

(7R)-7-[(phenylacetyl)amino]-3-[2-fluoro-4-(phenyl)phenylthio]-3-cephem-4-carboxylate, 4-methoxybenzyl ester This was prepared by a procedure similar to that for Example 15, but potassium 2-fluoro-4-(phenyl)phenylthiolate was used.

Example 30

(7R)-7-[(2-Phenylacetyl)amino]-3-[3-(2-thienyl)phenylthio]-3-cephem-4-carboxylate, 4-methoxybenzyl ester This was prepared by a procedure similar to that for Example 15, but sodium 3-(2-thienyl)phenyl thiolate was used.

Example 31

(7R)-7-[(2-Phenylacetyl)amino]-3-[3,4-dichlorophenylthio]-3-cephem-4-carboxylate, 4-methoxybenzyl ester This was prepared by a procedure similar to that for Example 15, but sodium 3,4-dichlorophenyl thiolate was used.

Example 32

(7R)-7-[(2-Thienylacetyl)amino]-3-[5-bromo-4-(1-methyl-2-imidazolyl)phenylthio]-3-cephem-4-carboxylate, 4-methoxybenzyl ester This was prepared by a procedure similar to that for Example 15, but (7R)-7-[(2-thienylacetyl)amino]-3-trifluoromethanesulfonyloxy-3-cephem-4-carboxylate, 4-methoxybenzyl ester and sodium 5-bromo-4-(1-methyl-2-imidazolyl)phenyl thiolate was used.

Example 33

(7R)-7-Amino-3-(2-bromophenylthio)-3-cephem-4-carboxylate, benzhydryl ester

To a solution of (7R)-7-(phenylacetyl)amino-3-(2-bromophenylthio)-3-cephem-4-carboxylate, benzhydryl ester (812 mg, 1.21 mmol) and pyridine (195 μL, 2.42 mmol) in dichloromethane (5 mL) at 0° was added slowly a solution of phosphorus pentachloride (403 mg, 1.94 mmol) in dichloromethane (9 mL). After 15 min at 0°, isobutyl alcohol (1.1 mL, 12.1 mmol) was added in one portion. The mixture was diluted with dichloromethane (20 mL), and was washed with 5% aqueous sodium bicarbonate solution (20 mL). The organic layer was dried with sodium sulfate, and the solvent was removed with a rotary evaporator. The residue was subjected to flash chromatography on silica gel (33% to 50% ethyl acetate/hexane) to afford 300 mg (45%) of the title compound.

Example 34

(7R)-7-Amino-3-(2-iodophenylthio)-3-cephem-4-carboxylate, 4-methoxybenzyl ester

A mixture of (7R)-7-(phenylacetyl)amino-3-(2-iodophenylthio)-3-cephem-4-carboxylate, 4-methoxybenzyl ester (850 mg, 1.21 mmol) and pyridine (195 μL, 2.42 mmol) in dichloromethane (5 mL) at 0° was treated slowly with a solution of phosphorus penta-chloride (403 mg, 1.94 mmol) in dichloromethane (9 mL). After 15 min at 0°, isobutyl alcohol (1.1 mL, 12.1 mmol) was added in one portion. The mixture was diluted with dichloromethane (20 mL), and was washed with 5% aqueous sodium bicarbonate solution (20 mL). The organic layer was dried with sodium sulfate, and the solvent was removed with a rotary evaporator. The residue was subjected to flash chromatography on silica gel (33% to 50% ethyl acetate/hexane) to afford 300 mg (50%) of the title compound.

Substantially following the methods described in Examples 33–34, the compounds of the invention listed below in Examples 35–50 can be obtained.

Example 35

(7R)-7-Amino-3-(4-biphenylthio)-3-cephem-4-carboxylate, benzhydryl ester

The procedure of Example 33 is employed, except (7R)-7-[(phenylacetyl)amino]-3-(4-biphenylthio)-3-cephem-4-carboxylate, benzhydryl ester is used.

Example 36

(7R)-7-Amino-3-[4-(2-imidazolyl)phenylthio]-3-cephem-4-carboxylate, benzhydryl ester The procedure of Example 33 is employed, except (7R)-7-[(phenylacetyl)amino]-3-[4-(2-imidazolyl)phenylthio]-3-cephem-4-carboxylate, benzhydryl ester is used.

Example 37

(7R)-7-Amino-3-[3-bromo-4-(phenyl)phenylthio]-3-cephem-4-carboxylate, benzhydryl ester The procedure of Example 33 is employed, except (7R)-7-[(phenylacetyl)amino]-3-[3-bromo-4-(phenyl)phenylthio]-3-cephem-4-carboxylate, benzhydryl ester is used.

Example 38

(7R)-7-Amino-3-[(2-trifluoromethoxy)phenylthio]-3-cephem-4-carboxylate, benzhydryl ester The procedure of Example 33 is employed, except (7R)-7-[(phenylacetyl)amino]-3-[(2-trifluoromethoxy)phenylthio]-3-cephem-4-carboxylate, benzhydryl ester is used.

Example 39

(7R)-7-Amino-3-(dibenzofuran-2-ylthio)-3-cephem-4-carboxylate, benzhydryl ester

The procedure of Example 33 is employed, except (7R)-7-[(phenylacetyl)amino]-3-(dibenzofuran-2-ylthio)-3-cephem-4-carboxylate, benzhydryl ester is used.

Example 40

(7R)-7-Amino-3-[4-(2-thienyl)phenylthio]-3-cephem-4-carboxylate, benzhydryl ester The procedure of Example 33 is employed, except (7R)-7-[(phenylacetyl)amino]-3-[4-(2-thienyl)phenylthio]-3-cephem-4-carboxylate, benzhydryl ester is used.

Example 41

(7R)-7-Amino-3-[(6-chloromethyl)dibenzofuran-2-ylthio]-3-cephem-4-carboxylate, 4-methoxybenzyl ester A procedure similar to Example 33 is employed, except (7R)-7-[(phenylacetyl)amino]-3-[6-(hydroxymethyl)dibenzofuran-2-ylthio]-3-cephem-4-carboxylate, 4-methoxybenzyl ester is used in the presence of a second equivalent of phosphorus pentachloride and pyridine.

Example 42

(7R)-7-Amino-3-[(7-chloromethyl)dibenzofuran-3-ylthio]-3-cephem-4-carboxylate, 4-methoxybenzyl ester Procedure similar to Example 33 is employed, except (7R)-7-[(phenylacetyl)amino]-3-[7-(hydroxymethyl)dibenzofuran-3-ylthio]-3-cephem-4-carboxylate, 4-methoxybenzyl ester is used in the presence of a second equivalent of phosphorus pentachloride and pyridine.

Example 43

(7R)-7-Amino-3-(2,5-dichlorophenylthio)-3-cephem-4-carboxylate, 4-methoxybenzyl ester Procedure similar to Example 33 is employed, except (7R)-7-[(phenylacetyl)amino]-3-(2,5-dichlorophenylthio)-3-cephem-4-carboxylate, 4-methoxybenzyl ester is used.

Example 44

(7R)-7-Amino-3-[4-(2-oxazolylmethyl)phenylthio]-3-cephem-4-carboxylate, 4-methoxybenzyl ester Procedure similar to Example 33 is employed, except (7R)-7-[(phenylacetyl)amino]-3-[4-(2-oxazolylmethyl)phenylthio]-3-cephem-4-carboxylate, 4-methoxybenzyl ester is used.

Example 45

(7R)-7-Amino-3-[4-(1-imidazolylmethyl)phenylthio]-3-cephem-4-carboxylate, 4-methoxybenzyl ester Procedure similar to Example 33 is employed, except (7R)-7-[(phenylacetyl)amino]-3-[4-(1-imidazolylmethyl)phenylthio]-3-cephem-4-carboxylate, 4-methoxybenzyl ester is used.

Example 46

(7R)-7-Amino-3-[4-(1-imidazolylmethyl)phenylthio]-3-cephem-4-carboxylate, 4-methoxybenzyl ester Procedure similar to Example 33 is employed, except (7R)-7-[(phenylacetyl)amino]-3-[4-(1-imidazolylmethyl)phenylthio]-3-cephem-4-carboxylate, 4-methoxybenzyl ester is used.

Example 47

(7R)-7-Amino-3-[2-bromo-4-(ethoxycarbonyl)phenylthio]-3-cephem-4-carboxylate, 4-methoxybenzyl ester Procedure similar to Example 33 is employed, except (7R)-7-[(phenylacetyl)amino]-3-[2-bromo-4-(ethoxycarbonyl)phenylthio]-3-cephem-4-carboxylate, 4-methoxybenzyl ester is used.

Example 48

(7R)-7-Amino-3-[4-(2-thiazolyl)phenylthio]-3-cephem-4-carboxylate, 4-methoxybenzyl ester Procedure similar to Example 33 is employed, except (7R)-7-[(phenylacetyl)amino]-3-[4-(thiazolyl)phenylthio]-3-cephem-4-carboxylate, 4-methoxybenzyl ester is used.

Example 49

(7R)-7-Amino-3-[4-(cyanamido)phenylthio]-3-cephem-4-carboxylate, 4-methoxybenzyl ester Procedure similar to Example 33 is employed, except (7R)-7-[(phenylacetyl)amino]-3-[4-(cyanamido)phenylthio]-3-cephem-4-carboxylate, 4-methoxybenzyl ester is used.

Example 50

(7R)-7-Amino-3-[4-(2-furyl)phenylthio]-3-cephem-4-carboxylate, 4-methoxybenzyl ester Procedure similar to Example 33 is employed, except (7R)-7-[(phenylacetyl)amino]-3-[4-(2-furyl)phenylthio]-3-cephem-4-carboxylate, 4-methoxybenzyl ester is used.

Example 51

(7R)-7-[[2-(2-Amino-4-thiazolyl)-2-(syn-methoxyimino)acetyl]-amino-3-(4-bromophenylthio)-3-cephem-4-carboxylate, benzhydryl ester.

To solution of 2-(2-amino-4-thiazolyl)-2-(syn-methoxyimino)]acetic acid (40 mg, 0.20 mmol) and 1-hydroxybenzotriazole (27 mg, 0.20 mmol) in DMF (2 mL) is added dicyclohexylcarbodiimide (45 mg, 0.22 mmol). After stirring for 15 min, a solution of (7R)-7-amino-3-(2-bromophenylthio)-3-cephem-4-carboxylate, benzhydryl ester (110 mg, 0.20 mmol) in DMF (1.5 mL) is added. The mixture is stirred at room temperature overnight, and is partitioned between 20% hexane/EtOAc (20 mL) and water (50 mL). The organic layer is dried over sodium sulfate, and the solvent is removed with a rotary evaporator. The crude product was chromatographed on silica gel (30% EtOAc/hexane), to afford 74 mg (50%) of the title compound.

Using substantially the same procedure as in Example 51, the items of the following Examples 52–82 can similarly be prepared.

Example 52

(7R)-7-[[2-(2-Amino-4-thiazolyl)-2-(syn-methoxyimino)acetyl]-amino]-3-(biphenylthio)-3-cephem-4-carboxylate, benzhydryl ester The procedure of Example 51 is employed, but the reactants are 2-(2-amino-4-thiazolyl)-2-(syn-methoxyimino)acetic acid and (7R)-7-amino-3-(biphenylthio)-3-cephem-4-carboxylate, benzyhydryl ester.

EXAMPLE 53

(7R)-7-[[2-(2-Amino-4-thiazolyl)-2-(syn-hydroxyimino) acetyl]-amino]-3-(biphenylthio)-3-cephem-4-carboxylate, benzhydryl ester The procedure of Example 51 is employed, but the reactants are 2-(2-amino-4-thiazolyl)-2-(syn-hydroxyimino) acetic acid and (7R)-7-amino-3-(biphenylthio)-3-cephem-4-carboxylate, benzyhydryl ester.

Example 54

(7R)-7-[[2-(2-Amino-4-thiazolyl)-2-(syn-hydroxyimino)acetyl]-amino]-3-(2-iodophenylthio)-3-cephem-4-carboxylate, 4-methoxybenzyl ester The procedure of Example 51 is employed, but the reactants are 2-(2-amino-4-thiazolyl)-2-(syn-hydroxyimino)acetic acid and (7R)-7-amino-3-(2-iodophenylthio)-3-cephem-4-carboxylate, 4-methoxybenzyl ester.

Example 55

(7R)-7-[[2-(2-Amino-4-thiazolyl)-2-(syn-hydroxyimino)acetyl]-amino]-3-[4-(ethoxycarbonyl)phenylthio)]-3-cephem-4-carboxylate, 4-methoxybenzyl ester The procedure of Example 51 is employed, but the reactants are 2-(2-amino-4-thiazolyl)-2-(syn-hydroxyimino)acetic acid and (7R)-7-amino-3-[4-(ethoxycarbonyl)phenylthio]-3-cephem-4-carboxylate, 4-methoxybenzyl ester.

Example 56

(7R)-7-[[2-(2-Amino-4-thiazolyl)-2-[[[syn-(tert-butoxy)carbonyl-methoxyimino]acetyl]amino]-3-[4-(2-thienyl)phenylthio]-3-cephem-4-carboxylate, 4-methoxybenzyl ester The procedure of Example 51 is employed, but the reactants are 2-(2-amino-4-thiazolyl)-2-[syn-(tert-butoxy)carbonylmethoxyimino]acetic acid and (7R)-7-amino-3-[4-(2-thienyl)phenylthio]-3-cephem-4-carboxylate, 4-methoxybenzyl ester.

Example 57

(7R)-7-[[2-(2-Amino-4-thiazolyl)-2-[[[syn-(tert-butoxy)carbonylmethoxy-iminoacetyl]amino]-3-[4-(2-furyl)phenylthio]-3-cephem-4-carboxylate,4-methoxybenzyl ester The procedure of Example 51 is employed, but the reactants are 2-(2-amino-4-thiazolyl)-2-[syn-(tert-butoxy) carbonylmethoxyimino]acetic acid and (7R)-7-amino-3-[4-(2-furyl)phenylthio]-3-cephem-4-carboxylate, 4-methoxybenzyl ester.

Example 58

(7R)-7-[[2-(2-Amino-4-thiazolyl)-2-(syn-2-fluoroethoxyimino)-acetyl]amino]-3-(2-iodophenylthio)-3-cephem-4-carboxylate, 4-methoxybenzyl ester The procedure of Example 51 is employed, but the reactants are 2-(2-amino-4-thiazolyl)-2-(syn-2-fluoroethoxyimino)acetic acid and (7R)-7-amino-3-(2-iodophenylthio)-3-cephem-4-carboxylate, 4-methoxybenzyl ester.

Example 59

(7R)-[(2-Thienylacetyl)amino]-3-[6-(chloromethyl) dibenzofuran-3-ylthio]-3-cephem-4-carboxylate, benzhydryl ester The procedure of Example 51 is employed, but the reactants are 2-thienylacetyl chloride-pyridine and (7R)-7-amino-3-[6-(chloromethyl)dibenzofuran-3-ylthio]-3-cephem-4-carboxylate, benzhydryl ester.

Example 60

(7R)-[(2-Thienylacetyl)amino]-3-[6-(chloromethyl) dibenzofuran-1-ylthio]-3-cephem-4-carboxylate, benzhydryl ester The procedure of Example 51 is employed, but the reactants are 2-thienylacetyl chloride-pyridine and (7R)-7-amino-3-[6-(chloromethyl)dibenzofuran-1-ylthio]-3-cephem-4-carboxylate, benzhydryl ester.

Example 60

(7R)-[(2-Thienylacetyl)amino]-3-[6-(chloromethyl) dibenzofuran-1-ylthio]-3-cephem-4-carboxylate, benzhydryl ester The procedure of Example 51 is employed, but the reactants are 2-thienylacetyl chloride-pyridine and (7R)-7-amino-3-[6-(chloromethyl)dibenzofuran-1-ylthio]-3-cephem-4-carboxylate, benzhydryl ester.

Example 61

(7R)-[[(2-Amino-4-thiazolyl)acetyl]amino]-3-(2-bromophenylthio)-3-cephem-4-carboxylate, 4-methoxybenzyl ester The procedure of Example 51 was employed, but the reactants are (2-amino-4-thiazolyl)acetic acid and (7R)-7-amino-3-(2-bromophenylthio)-3-cephem-4-carboxylate, 4-methoxybenzyl ester.

EXAMPLE 62

(7R)-[[(2-Amino-4-thiazolyl)acetyl]amino]-3-(2-iodophenylthio)-3-cephem-4-carboxylate, 4-methoxybenzyl ester The procedure of Example 51 was employed, but the reactants are (2-amino-4-thiazolyl)acetic acid and (7R)-7-amino-3-(2-iodophenylthio)-3-cephem-4-carboxylate, 4-methoxybenzyl ester.

Example 63

(7R)-[(2-Furylacetyl)amino]-3-[4-(2-oxazolylmethyl)phenylthio]-3-cephem-4-carboxylate, 4-methoxybenzyl ester The procedure of Example 51 was employed, but the reactants are 2-furylacetic acid and (7R)-7-amino-3-[4-(2-oxazolylmethyl)phenylthio)-3-cephem-4-carboxylate, 4-methoxybenzyl ester.

Example 63a (7R)-[(2-Furylacetyl)amino]-3-[4-(2-imidazolylmethyl) phenylthio]-3-cephem-4-carboxylate, benzhydryl ester The procedure of Example 51 was employed, but the reactants are 2-furylacetic acid and (7R)-7-amino-3-[4-(2-imidazolylmethyl)phenylthio)-3-cephem-4-carboxylate, benzhydryl ester.

Example 64

(7R)-[(4-Bromophenylacetyl)amino]-3-[dibenzofuran-3-ylthio]-3-cephem-4-carboxylate, benzyhydryl ester The procedure of Example 51 was employed, but the reactants are 4-bromophenylacetyl chloride and (7R)-7-amino-3-dibenzofuran-3-ylthio]-3-cephem-4-carboxylate, benzhydryl ester.

Example 65

(7R)-[(2-Iodophenylacetyl)amino]-3-[2-bromophenylthio]-3-cephem-4-carboxylate, benzyhydryl ester The procedure of Example 51 was employed, but the reactants are 2-iodophenylacetyl chloride and (7R)-7-amino-3-[2-bromophenylthio]-3-cephem-4-carboxylate, benzhydryl ester.

Example 66

(7R)-[[(2-Iodophenylthio)acetyl]amino]-3-[2-iodohenylthio]-3-cephem-4-carboxylate, 4-methoxybenzyl, ester The procedure of Example 51 was employed, but the reactants are 2-(iodophenythio)acetic acid and (7R)-7-amino-3-[2-iodophenylthio]-3-cephem-4-carboxylate, 4-methoxybenzyl ester.

Example 67

(7R)-[[(2-Iodophenylthio)acetyl]amino]-3-(biphenylthio)-3-cephem-4-carboxylate, 4-methoxybenzyl ester The procedure of Example 51 was employed, but the reactants are 2-(iodophenythio)acetic acid and (7R)-7-amino-3-(biphenylthio)-3-cephem-4-carboxylate, 4-methoxybenzyl ester.

Example 68

(7R)-[[(Trifluoromethylthio)acetyl]amino]-3-[4-(2-oxazolyl)phenyl-thio]-3-cephem-4-carboxylate, 4-methoxybenzyl ester The procedure of Example 51 was employed, but the reactants are (trifluoromethylthio)acetic acid and (7R)-7-amino-3-[4-(2-oxazolyl)phenylthio]-3-cephem-4-carboxylate, 4-methoxybenzyl ester.

Example 69

(7R)-[[(Trifluoromethylthio)acetyl]amino]-3-[2-bromo-4-(ethoxycarbonyl)phenylthio]-3-cephem-4-carboxylate, 4-methoxybenzyl ester The procedure of Example 51 was employed, but the reactants are (trifluoromethylthio)acetic acid and (7R)-7-amino-3-[2-bromo-4-(ethoxycarbonyl)phenylthio]-3-cephem-4-carboxylate, 4-methoxybenzyl ester.

Example 70

(7R)-7-[[2-(2-Furyl)-2-(syn-methoxyimino) acetyl] amino]-3-(2-bromophenylthio)-3-cephem-4-carboxylate, benzhydryl ester The procedure of Example 51 was employed, but the reactants are 2-(2-furyl)-2-(syn-methoxyimino)acetic acid and (7R)-7-amino-3-(2-bromophenylthio)-3-cephem-4-carboxylate, benzhydryl ester.

Example 71

(7R)-7-[[2-(2-Furyl)-2-(syn-methoxyimino)acetyl] amino]-3-(dibenzo-furan-2-ylthio)-3-cephem-4-carboxylate, benzhydryl ester The procedure of Example 51 was employed, but the reactants are 2-(2-furyl)-2-(syn-methoxyimino)acetic acid and (7R)-7-amino-3-(dibenzofuran-2-ylthio)-3-cephem-4-carboxylate, benzhydryl ester.

Example 72

(7R)-7-[[2-(2-Furyl)-2-(syn-methoxyimino)acetyl]
amino]-3-[4-(1-methyl-2-imidazolyl)phenylthio]-3-
cephem-4-carboxylate, benzhydryl ester The procedure of Example 51 was employed, but the reactants are 2-(2-furyl)-2-(syn-methoxyimino)acetic acid and (7R)-7-amino-3-[4-(1-methyl-2-imidazolyl)-3-cephem-4-carboxylate, benzhydryl ester.

Example 73

(7R)-7-[[2-(2-Furyl)-2-(methoxyimino)acetyl]
amino]-3-[6-(hydroxy-methyl)dibenzofuran-3-
ylthio]-3-cephem-4-carboxylate, benzhydryl ester The procedure of Example 51 was employed, but the reactants are 2-(2-furyl)-2-(syn-methoxyimino)acetic acid and (7R)-7-amino-3-[6-(hydroxymethyl)dibenzofuran-3-ylthio]-3-cephem-4-carboxylate, benzhydryl ester.

Example 74

(7R)-7-[(D-Phenylglycyl)amino]-3-(dibenzofuran-1-
ylthio)-ceph-3-em-4-carboxylate, benzhydryl ester This was prepared by the reaction of D-phenylglycyl chloride hydrochloride and (7R)-7-amino-3-(dibenzofuran-1-ylthio)-3-cephem-4-carboxylate, benzhydryl ester in the presence of tetrahydrofuran and aqueous sodium bicarbonate.

Example 75

(7R)-7-[(D-Phenylglycyl)amino]-3-(dibenzofuran-2-
ylthio)-ceph-3-em-4-carboxylate, benzhydryl ester This was prepared by the reaction of D-phenylglycyl chloride hydrochloride and (7R)-7-amino-3-(dibenzofuran-2-ylthio)-3-cephem-4-carboxylate, benzhydryl ester in the presence of tetrahydrofuran and aqueous sodium bicarbonate.

Example 76

(7R)-7-[(D-Phenylglycyl)amino]-3-(dibenzofuran-3-
ylthio)-ceph-3-em-4-carboxylate, benzhydryl ester This was prepared by the reaction of D-phenylglycyl chloride hydrochloride and (7R)-7-amino-3-(dibenzofuran-3-ylthio)-3-cephem-4-carboxylate, benzhydryl ester in the presence of tetrahydrofuran and aqueous sodium bicarbonate.

Example 77

(7R)-7-[(D-(2-Formyloxy)phenylacetyl)amino]-3-[4-
(2-furyl)phenyl-thio]-3-cephem-4-carboxylate,
4-methoxybenzyl ester The procedure of Example 51 was employed, but the reactants are D-(2-formyloxy)phenylacetic acid and (7R)-7-amino-3-[4-(2-furyl)phenylthio)-3-cephem-4-carboxylate, 4-methoxybenzyl ester.

Example 78

(7R)-7-[(Cyanoacetyl)amino]-3-[3-(imidazolylm-
ethyl) phenylthio]-3-cephem-4-carboxylate, 4-meth-
oxybenzyl ester The procedure of Example 51 was employed, but the reactants are cyanoacetic acid and (7R)-7-amino-3-[3-(imidazolylmethyl)phenylthio]-3-cephem-4-carboxylate, 4-methoxybenzyl ester.

Example 79

(7R)-7-[(Cyanoacetyl)amino]-3-[3-dibenzothien-1-
ylthio]-3-cephem-4-carboxylate, 4-methoxybenzyl
ester This was prepared by a procedure similar to that for Example 51, but the reactants are cyanoacetic acid and (7R)-7-amino-3-[3-dibenzothien-1-ylthio]-3-cephem-4-carboxylate, 4-methoxybenzyl ester.

Example 80

(7R)-7-[(Cyanoacetyl)amino]-3-[4-(trifluoromethyl)
phenylthio]-3-cephem-4-carboxylate, 4-methoxy-
benzyl ester This was prepared by a procedure similar to that for Example 51, but the reactants are cyanoacetic acid and (7R)-7-amino-3-[4-(trifluoromethyl)phenylthio]-3-cephem-4-carboxylate, 4-methoxybenzyl ester.

Example 81

(7R)-7-[(α-[D-4-Ethyl-2,3-dioxo-1-piperazinecar-
boxamido]-α-phenylacetyl)amino]-3-[2-iodo-4-(cy-
anamido)phenylthio]-3-cephem-4-carboxylate,
4-methoxybenzyl ester This was prepared by the reaction of α-[D-4-ethyl-2,3-dioxo-1-piperazine-carboxamido]-α-phenylacetyl chloride and (7R)-7-amino-3-[2-iodo-4-(cyanamido)phenylthio]-3-cephem-4-carboxylate, 4-methoxybenzyl ester in the presence of tetrahydrofuran and aqueous sodium bicarbonate.

Example 82

(7R)-7-[(α-[D-4-Ethyl-2,3-dioxo-1-piperazinecarboxamido]-α-phenylacetyl)amino]-3-[dibenzofuran-3-ylthio]-3-cephem-4-carboxylate, 4-methoxybenzyl ester This was prepared by the reaction of α-[D-4-ethyl-2,3-dioxo-1-piperazine-carboxamido]-α-phenylacetyl chloride and (7R)-7-amino-3-[dibenzofuran-3-ylthio]-3-cephem-4-carboxylate, 4-methoxybenzyl ester in the presence of tetrahydrofuran and aqueous sodium bicarbonate.

Example 83

(7R)-7-[(phenylacetyl)amino]-3-[6-(chloromethyl)dibenzofuran-3-ylthio]-3-cephem-4-carboxylate, benzhydryl ester This was prepared by the reaction of (7R)-7-(phenylacetyl) amino]-3-[6-(hydroxymethyl)dibenzofuran-3-ylthio]-3-cephem-4-carboxylate, benzhydryl ester with 1.1 equivalents of thionyl chloride and pyridine in methylene chloride at 0° C.

Under substantially the same procedure as in Example 83, the items of the following Examples 84–88 are similarly prepared.

Example 84

(7R)-7-[(phenylacetyl)amino]-3-[7-(chloromethyl)dibenzofuran-3-ylthio]-3-cephem-4-carboxylate, 4-methoxybenzyl ester This was prepared by the reaction of (7R)-7(phenylacetyl)amino]-3-[7-(hydroxymethyl)dibenzofuran-3-ylthio]-3-cephem-4-carboxylate, 4-methoxybenzyl ester with 1.1 equivalents of thionyl chloride and pyridine in methylene chloride at 0° C.

Example 85

(7R)-7-[(2-Furylacetyl)amino]-3-[7-(chloromethyl)dibenzofuran-3-ylthio]-3-cephem-4-carboxylate, 4-methoxybenzyl ester This was prepared by the reaction of (7R)-7-[(2-furylacetyl) amino]-3-[7-(hydroxy-methyl) dibenzofuran-3-ylthio]-3-cephem-4-carboxylate, 4-methoxybenzyl ester with 1.1 equivalents of thionyl chloride and pyridine in methylene chloride at 0° C.

Example 86

(7R)-7-[2-(2-Thienylacetyl)-2-(syn-methoxyimino)acetyl]amino]-3-[4-[4'-(chloromethyl)phenyl]phenylthio]-3-cephem- 4-carboxylate, 4-methoxybenzyl ester This was prepared by the reaction of (7R)-7-[(2-thienylacetyl) amino]-3-[4-[4'-(hydroxymethyl)phenyl]phenylthio]-3-cephem-4-carboxylate, 4-methoxybenzyl ester with 1.1 equivalents of thionyl chloride and pyridine in methylene chloride at 0° C.

Example 87

(7R)-7-[[2-(2-Amino-4-thiazolyl)-2-(syn-2-fluoroethoxyimino)-acetyl]amino]-3-[4-(chloromethyl) phenylthio]-3-cephem-4-carboxylate, 4-methoxybenzyl ester This was prepared by the reaction of (7R)-7-[[2-(2-amino-4-thiazolyl)-2-(syn-2-fluoroethoxyimino)acetyl)amino]-3-[4-(hydroxymethyl)phenylthio]-3-cephem-4-carboxylate, 4-methoxybenzyl ester with 1.1 equivalents of thionyl chloride and pyridine in methylene chloride at 0° C.

Example 88

(7R)-7-[(α-[D-4-Ethyl-2,3-dioxo-1-piperazinecarboxamido]-α-phenylacetyl)amino]-3-[4-(chloromethyl)phenylthio]-3-cephem-4-carboxylate, 4-methoxybenzyl ester This was prepared by the reaction of 7-[(α-[D-4-ethyl-2,3-dioxo-1-piperazine-carboxamido]-α-phenylacetyl)amino]-3-[4-(hydroxymethyl)phenylthio]-3-cephem-4-carboxylate, 4-methoxybenzyl ester with 1.1 equivalents of thionyl chloride and pyridine in methylene chloride at 0° C.

Example 89

(7R)-7-[(phenylacetyl)amino]-3-[6-(pyridin-1-iummethyl)dibenzofuran-3-ylthio]-3-cephem-4-carboxylate, benzhydryl ester, chloride salt This was made by the reaction of (7R)-7-(phenylacetyl)amino]-3-[6-(chloromethyl)dibenzofuran-3-ylthio]-3-cephem-4-carboxylate,-benzhydryl ester with 4.0 equivalents of pyridine in acetonitrile. Desired material was obtained by precipitation with diethyl ether.

Example 90

(7R)-7-[(phenylacetyl)amino]-3-[6-(N-methylimidazol-1-iummethyl)-dibenzofuran-3-ylthio]-ceph-3-em4-carboxylate, benzhydryl ester, chloride salt This was made by the reaction of (7R)-7-(phenylacetyl)amino]-3-[6-(chloromethyl)dibenzofuran-3-ylthio]-3-cephem-4-carboxylate, benzhydryl ester with 4.0 equivalents of 1-methylimidazole in acetonitrile. Desired material was obtained by precipitation with diethyl ether.

Example 91

(7R)-7-[(phenylacetyl)amino]-3-[7-(pyridin-1-iummethyl)-dibenzofuran-3-ylthio]-ceph-3-em-4-carboxylate, benzhydryl ester, chloride salt This was made by the reaction of (7R)-7-(phenylacetyl)amino]-3-[7-(chloromethyl)dibenzofuran-3-ylthio]-3-cephem-4-carboxylate, benzhydryl ester with 4.0 equivalents of pyridine in acetonitrile. Desired material was obtained by precipitation with diethyl ether.

Example 92

(7R)-7-[(2-Furylacetyl)amino]-3-[7-(N-methylimidazol-1-iummethyl)-dibenzofuran-3-ylthio]-ceph-3-em-4-carboxylate, 4-methoxybenzyl ester, chloride salt This was made by the reaction of (7R)-7-[(2-furylacetyl)amino]-3-[7-(chloromethyl)dibenzofuran-3-ylthio]-3-cephem-4-carboxylate, 4-methoxybenzyl with 4.0 equivalents of pyridine in acetonitrile. Desired material was obtained by precipitation with diethyl ether.

Example 93

(7R)-7-[(2-Furylacetyl)amino]-3-[6-(pyridin-1-iummethyl)dibenzo-furan-2-ylthio]-ceph-3-em-4-carboxylate, 4-methoxybenzyl ester, chloride salt This was made by the reaction of (7R)-7-[(2-furylacetyl)amino]-3-[6-(chloromethyl)dibenzofuran-3-ylthio]-3-cephem-4-carboxylate, 4-methoxybenzyl with 4.0 equivalents of pyridine in acetonitrile. Desired material was obtained by precipitation with diethyl ether.

Example 94

(7R)-7-[[2-(2-Thienyl)-2-(syn-methoxyimino)acetyl]amino]-3-[4-(N-pyridin-1-iummethyl)phenylthio]-ceph-3-em-4-carboxylate, 4-methoxybenzyl ester, chloride salt This was made by the reaction of (7R)-7-[[2-(2-thienylacetyl)-2-(syn-methoxy-imino)acetyl]amino]-3-[4-(chloromethyl)phenylthio]-ceph-3-em-4-carboxylate, 4-methoxybenzyl ester with 4.0 equivalents of pyridine in acetonitrile. Desired material was obtained by precipitation with diethyl ether.

Example 95

(7R)-7-[[2-(2-Amino-4-thiazolyl)-2-(syn-2-fluoroethoxyimino) acetyl]-amino]-3-[4-(N-methylimidazol-1-iummethyl)phenylthio]- ceph-3-em-4-carboxylate, 4-methoxybenzyl ester, chloride salt This was made by the reaction of (7R)-7-[[2-(2-amino-4-thiazolyl)-2-(syn-2-fluoroethoxyimino)acetyl]amino]-3-[4-(chloromethyl)phenylthio]-ceph-3-em-4-carboxylate, 4-methoxybenzyl ester with 4.0 equivalents of 1-methylimidazole in acetonitrile. Desired material was obtained by precipitation with diethyl ether.

Example 96

(7R)-7-[[2-(2-Amino-4-thiazolyl)-2-(syn-(tert-butoxy)carbonyl-methoxyimino)acetyl]-amino]-3-[4-(N-methylimidazol-1-iummethyl)phenylthio]-ceph-3-em-4-carboxylate, 4-methoxybenzyl ester, chloride salt This was made by the reaction of (7R)-7-[[2-(2-amino-4-thiazolyl)-2-(syn-(tert-butoxy)carbonylmethoxyimino)acetyl]amino]-3-[4(chloromethyl)phenylthio]-ceph-3-em-4-carboxylate, 4-methoxybenzyl ester with 4.0 equivalents of 1-methylimidazole in acetonitrile. Desired material was obtained by precipitation with diethyl ether.

Example 97

(7R)-7-[(α-[D-4-Ethyl-2,3-dioxo-1-piperazinecarboxamido]-α-phenylacetyl)amino]-3-[4-(pyridin-1-iummethyl)phenylthio]-3-cephem-4-carboxylate, 4-methoxybenzyl ester, chloride salt This was made by the reaction of (7R)-7-[(α-[D-4-ethyl-2,3-dioxo-1-piperazine-carboxamido]-α-phenylacetyl)amino]-3-[4-(chloromethyl)phenylthio]-3-cephem-4-carboxylate, 4-methoxybenzyl ester with 4.0 equivalents of pyridine in acetonitrile. Desired material was obtained by precipitation with diethyl ether.

Example 98

(7R)-7-[(2,4-Dibromophenylacetyl)amino]-3-[4'-(pyridin-1-ium-methyl)biphenylthio]-ceph-3-em-4-carboxylate, 4-methoxy-benzyl ester, chloride salt This was made by the reaction of (7R)-7-[(2,4-dibromophenylacetyl)amino]-3-[4'-(chloromethyl)biphenylthio]-3-cephem-4-carboxylate, 4-methoxybenzyl ester with 4.0 equivalents of pyridine in acetonitrile. Desired material was obtained by precipitation with diethyl ether.

Example 99

(7R)-7-[[(2,4-Dichlorophenylthio)acetyl]amino]-3-[2-bromo-4-(N-methylimidazol-1-iummethyl)phenylthio]-ceph-3-em-4-carboxylate, 4-methoxybenzyl ester, chloride salt This was made by the reaction of (7R)-7-[[(2,4-dichlorophenylthio)acetyl]amino]-3-[2-bromo-4-(chloromethyl)phenylthio]-3-cephem-4-carboxylate, 4-methoxy-benzyl ester with 4.0 equivalents of 1-methylimidazole in acetonitrile. Desired material was obtained by precipitation with diethyl ether.

Example 100

(7R)-7-[[(2,4-Dichlorophenylthio)acetyl]amino]-3-[2-bromo-4-(pyridin-1-iummethyl)phenylthio]-ceph-3-em-4-carboxylate, 4-methoxybenzyl ester, chloride salt This was made by the reaction of (7R)-7-[[(2,4-dichlorophenylthio)acetyl]amino]-3-[2-bromo-4-(chloromethyl)phenylthio]-3-cephem-4-carboxylate, 4-methoxybenzyl ester with 4.0 equivalents of pyridine in acetonitrile. Desired material was obtained by precipitation with diethyl ether.

Example 101

(7R)-7-[(phenylacetyl)amino]-3-(4-biphenylthio)-3-cephem-4-carboxylic acid

A solution of (7R)-7-[(phenylacetyl)amino]-3-(4-biphenylthio)-3-cephem-4-carboxylate, benzhydryl ester (450 mg, 0,670 mmol) and anisole (0.4 mL) in dichloromethane (3 mL) at 0° was treated with trifluoroacetic acid (4 mL).

After 1 h, the volatiles are removed with a rotary evaporator. The residue was subjected to column chromatography on silica gel (dichloromethane, then 10% AcOH/dichloromethane), affording 232 mg (69%) of the title compound. $^1$H NMR (acetone-d$_6$) δ3.37 (d, 1H, J=18), 3.63 (d, 1H, J=18), 3.84 (d, 1H, J=16), 3.92 (d, 1H, J=16), 5.25 (d, 1H, J=5), 5.93 (dd, 1H, J=5,9), 7.2–7.8 (m, 14H), 8.15 (d, 1H, J=9); IR (KBr) 1513, 1619, 1713, 1784, 3377cm$^{-1}$.

Example 102

(7R)-7-[(phenylacetyl)amino]-3-(4-bromophenylthio)-3-cephem-4-carboxylic acid

To a solution of (7R)-7-[(phenylacetyl)amino]-3-(4-bromophenylthio)-3-cephem-4-carboxylate, benzhydryl ester (80 mg, 0.12 mmol) in phenol (230 mg) at 45° was added trifluoroacetic acid (9 μL). After 1.5 h, the volatiles are removed with a rotary evaporator, and the residue was triturated with isopropanol/hexane. The resulting white solid was washed with ether and dried in vacuo, affording 48 mg (79%) of the title compound. $^1$H NMR (acetone-d$_6$) δ3.67 (d, 1H, J=16), 3.75 (d, 1H, J=16), 3.64 (d, 1H, J=18), 3.67 (d, 1H, J=18), 5.25 (d, 1H, J=5), 5.92 (d, 1H, J=5), 7.2–7.7 (m, 9H); IR (KBr) 1347, 1386, 1606, 1756, 3276 cm$^{-1}$.

Example 103

(7R)-7-[[2-(2-Amino-4-thiazolyl)-2-(syn-methoxyimino)acetyl]amino]-3-(4-bromophenylthio)-3-cephem-4-carboxylic acid To a mixture of (7R)-7-[[[2-(2-amino-4-thiazolyl)-2-(syn-methoxyimino)]acetyl]-amino]-3-(4-bromophenylthio)-3-cephem-4-carboxylate, benzhydryl ester (71 mg, 0.096 mmol) and anisole (0.2 mL) at 0° was added trifluoroacetic acid. After 1 h, the volatiles are removed with a rotary evaporator. The crude product was subjected to reverse-phase chromatography on C$_{18}$ adsorbent (acetonitrile/water 3:2), affording 11.6 mg (21%) of the title compound.

Under substantially the same procedures as in Examples 101–103, the items of the following Examples 104–141 can similarly be obtained.

Example 104

(7R)-7-[[(2-Amino-4-thiazolyl)acetyl]amino]-3-(2-bromophenylthio)-3-cephem-4-carboxylic acid Example 105

(7R)-7-[[(2-Amino-4-thiazolyl)acetyl]amino]-3-(2-iodophenylthio)-3-cephem-4-carboxylic acid Example 106

(7R)-7-[[2-(2-Amino-4-thiazolyl)-2-(syn-hydroxyimino) acetyl]amino]-3-[4-(ethoxycarbonyl)phenylthio]-3-cephem-4-carboxylic acid Example 107

(7R)-7-[[2-(2-Amino-4-thiazolyl)-2-(syn-methoxyimino)acetyl]amino]-3-(2-iodophenylthio) cephem-4-carboxylic acid Example 108

(7R)-7-[[2-(2-Amino-4-thiazolyl)-2-(syn-2-fluoroethoxyimino)acetyl]amino]-3-(2-iodophenylthio)-3-cephem-4-carboxylic acid Example 109

(7R)-7-[[2-(2-Amino-4-thiazolyl)-2-(syn-carboxymethoxyimino)acetyl]amino]-3-[4-(2thienyl)phenylthio]-3-cephem-4-carboxylic acid Example 110

(7R)-7-[(α-[D-4-Ethyl-2,3-dioxo-1-piperazinecarboxamido]-α-(hydroxyphenyl)acetyl)amino]-3-[2-iodo-4-(cyanoamido)phenylthio]-3-cephem-4-carboxylic acid Example 111

(7R)-7-[(α-[D-4-Ethyl-2,3-dioxo-1-piperazinecarboxamido]-α-(hydroxyphenyl)acetyl)amino]-3-[dibenzofuran-3-ylthio]-3-cephem-4-carboxylic acid Example 112

(7R)-7-[(2-Iodophenylthioacetyl)amino]-3-(2-iodophenylthio)-3-cephem-4-carboxylic acid Example 113

(7R)-7-[(2-Iodophenylthioacetyl)amino]-3-(biphenylthio)-3-cephem-4-carboxylic acid Example 114

(7R)-7-[(Cyanoacetyl)amino]-3-[3-(imidazolylmethyl) phenylthio]-3-cephem-4-carboxylic acid Example 115

(7R)-7-[(Cyanoacetyl)amino]-3-(dibenzothienyl-1-ylthio)-3-cephem-4-carboxylic acid Example 116

(7R)-7-[(Cyanoacetyl)amino]-3-[4-(trifluoromethyl) phenylthio]-3-cephem-4-carboxylic acid

Example 117

(7R)-7-[(2-Thienylacetyl)amino]-3-[6-(chloromethyl) dibenzofuran-3-ylthio]-3-cephem-4-carboxylic acid

Example 118

(7R)-7-[(2-Thienylacetyl)amino]-3-[dibenzofuran-3-ylthio]-3-cephem-4-carboxylic acid

Example 119

(7R)-7-[(2-Furylacetyl)amino]-3-[4-(2-oxazolylmethyl) phenylthio]-3-cephem-4-carboxylic acid

Example 120

(7R)-7-[(2-Furylacetyl)amino]-3-[4-(1-imidazolylmethyl) phenylthio]-3-cephem-4-carboxylic acid

Example 121

(7R)-7-[((Trifluoromethyl)thioacetyl)amino]-3-[4-(2-oxazolyl)phenylthio]-3-cephem-4-carboxylic

Example 122

(7R)-7-[((Trifluoromethyl)thioacetyl)amino]-3-[2-bromo-4-(ethoxy-carbonyl)phenylthio]-3-cephem-4-carboxylic acid

Example 123

(7R)-7-[(D-(2-Formyloxy)phenylacetyl)amino]-3-[4-(2-furyl)phenylthio]-3-cephem-4-carboxylic acid

Example 124

(7R)-7-[(phenylacetyl)amino]-3-(dibenzofuran-1-ylthio)-3-cephem-4-carboxylic acid

Example 125

(7R)-7-[(phenylacetyl)amino]-3-(dibenzofuran-3-ylthio)-3-cephem-4-carboxylic acid

Example 126

(7R)-7-[(phenylacetyl)amino]-3-(6-hydroxymethyldibenzofuran-3-ylthio)-3-cephem-4-carboxylic acid

Example 127

(7R)-7-[(phenylacetyl)amino]-3-(7-hydroxymethyldibenzofuran-3-ylthio)-3-cephem-4-carboxylic acid

Example 128

(7R)-7-[(D-Phenylglycyl)amino]-3-(dibenzofuran-1-ylthio)-3-cephem-4-carboxylic acid

Example 129

(7R)-7-[(D-Phenylglycyl)amino]-3-(dibenzofuran-2-ylthio)-3-cephem-4-carboxylic acid

Example 130

(7R)-7-{[2-(2-Furyl)-2-(syn-methoxyimino)acetyl]amino}-3-(dibenzofuran-1-ylthio)-3-cephem-4-carboxylic acid

Example 131

(7R)-7-{[2-(2-Furyl)-2-(syn-methoxyimino)acetyl]amino}-3-(dibenzofuran-2-ylthio)-3-cephem-4-carboxylic acid

Example 132

(7R)-7-[(2-(2-Amino-4-thiazolyl)-2-(syn-methoxyimino) acetyl)amino]-3-(6-hydroxymethyldibenzofuran-2-ylthio)-3-cephem-4-carboxylic acid

Example 133

(7R)-7-[((2-Amino-4-thiazolyl)acetyl)amino]-3(6-hydroxymethyldibenzo-furan-3-yl-thio)-3-cephem-4-carboxylic acid

Example 134

(7R)-7-{[2-(2-Furyl)-2-(methoxyimino)acetyl]amino}-3-(7-hydroxymethyl-dibenzofuran-3-ylthio)-3-cephem-4-carboxylic acid

Example 135

(7R)-7-{[2-(2-Furyl)-2-(methoxyimino)acetyl]amino}-3-(7-hydroxymethyl-dibenzofuran-1-ylthio)-3-cephem-4-carboxylic acid

Example 136

(7R)-7-[(phenylacetyl)amino]-3-[6-(pyridin-immethyl-1) dibenzofuran-3-ylthio]-3-cephem-4-carboxylate, inner salt

Example 137

(7R)-7-[(phenylacetyl)amino]-3-[6-(N-methylimidazol-1-iummethyl)dibenzofuran-3-ylthio]-ceph-3-em-4-carboxylic acid, inner salt

Example 138

(7R)-7-[(2-Thienylacetyl)amino]-3-[6-(N-methylimidazol-1-iummethyl)dibenzofuran-3-ylthio]-ceph-3-em-4-carboxylic acid, inner salt

Example 139

(7R)-7-[(2-Thienylacetyl)amino]-3-[6-(pyridiniummethyl)dibenzofuran-3-ylthio]ceph-3-em-4-carboxylic acid, inner salt

Example 140

(7R)-7-[(2-Thienylacetyl)amino]-3-[6-(pyridiniummethyl)dibenzofuran-2-ylthio]-ceph-3-em-4-carboxylic acid, inner salt

Example 141

(7R)-7-[(2-(2-Amino-4-thiazolyl)-2-(syn-hydroxyimino)acetyl]amino-3-(2-iodophenylthio)-3-cephem-4-carboxylic acid

Example 142

(7R)-7-[(phenylacetyl)amino]-3-[4-[(3-hydroxymethyl) phenyl]-phenylthio]-3-cephem-4-carboxylic acid, sodium salt (Pd coupling)

To a stirred solution of (7R)-7-(phenylacetyl)amino]-3-(4-iodophenyl-thio)-3-cephem-4-carboxylic acid (25.0 mg, 0.045 mmol), 3-hydroxymethyl-1-trimethylstannylbenzene (16.3 mg, 0.060 mmol), tri (2-furyl)phosphine (1.1 mg), sodium bicarbonate (4.2 mg, 0.045 mmol) and 2,6-di-t-butyl-4-methylphenol (2 mg) in N-methylpyrrolidinone (0.3 mL) was added tris (dibenzylideneacetone)dipalladium(0) (4.5 mg, 0.0049 mmol). The mixture was heated at 65° for 2 h, at which time the reaction was quenched by addition of 1% aqueous sodium bicarbonate solution (10 mL). The resulting solution was subjected to reverse phase chromatography ($C_{18}$ adsorbent, 30% acetonitrile/water), affording 9.2 mg (37%) of the title compound. $^1$H NMR (acetone-$d_6$) δ3.35 (d, 1H, J=16), 3.38 (d, 1H, J=16), 3.64 (d, 1H, J=18), 3.67 (d, 1H, J=18), 5.23 (d, 1H, J=5), 5.83 (dd, 1H, J=5,9), 7.2–7.8 (m, 13H), 8.15 (d, 1H, J=9); IR (KBr) 1387, 1610, 1654, 1762, 3264cm$^{-1}$.

Substantially following the method described in detail hereinabove in Example 142, the compounds of this invention listed below in Examples 143–156 can be prepared.

Example 143

(7R)-7-[(Thienylacetyl)amino]-3-[4-(2-imidazolyl) phenylthio]-3-cephem-4-carboxylic acid, sodium salt

Example 144

(7R)-7-[(2,4-Dichlorophenylthio)acetylamino]-3-[4-[(1-methyl-imidazol-4-yl)phenylthio]]-3-cephem-4-carboxylic acid, sodium salt

Example 145

(7R)-7-[(2,4-Difluorophenylthio)acetylamino]-3-[4-[(1-methyl-imidazol-4-yl)phenylthio]]-3-cephem-4-carboxylic acid, sodium salt

Example 146

(7R)-7-[[2-(2-Furyl)-2-(syn-methoxyimino) acetyl]amino]-3-[4-[(1-methylimidazol-4-yl)phenylthio]]-3-cephem-4-carboxylic acid, sodium salt

Example 147

(7R)-7-[a-[D-4-Ethyl-2,3-dioxo-1-piperazinecarboxamido]phenylacetylamino]-3-[4-[(1-methylimidazol-4-yl)phenylthio]]-3-cephem-4-carboxylic acid, sodium salt

Example 148

(7R)-7-[D-[(2-Formyloxy)phenylacetyl]amino]-3-[4-[(1-methyl-imidazol-4-yl)phenylthio]]-3-cephem-4-carboxylic acid, sodium salt

Example 149

(7R)-7-[(2-(2-Amino-4-thiazolyl)-2-(syn-methoxyimino) acetyl]amino-3-[4-[(1-methylimidazol-4-yl) phenylthio]]-3-cephem-4-carboxylic acid, sodium salt

Example 150

(7R)-7-[(2-(2-Amino-4-thiazolyl)-2-(syn-cyclopentoxyimino)acetyl]amino-3-[4-[(1-methylimidazol-4-yl) phenylthio]]-3-cephem-4-carboxylic acid, sodium salt

Example 151

(7R)-7-[(2-(2-Amino-4-thiazolyl)-2-(syn-cyclobutoxyimino)acetyl]amino-3-[4-[(1-methylimidazol-4-yl) phenylthio]]-3-cephem-4-carboxylic acid, sodium salt

Example 152

(7R)-7-[(D-(2-Formyloxy)phenylacetyl)amino]-3-[4-(2-furyl)phenylthio]-3-cephem-4-carboxylic acid, sodium salt

Example 153

(7R)-7-[(4-Chlorophenylacetyl)amino]-3-[2-(2-furyl)phenylthio]-3-cephem-4-carboxylic acid, sodium salt

Example 154

(7R)-7-[[(4-Methoxyphenylthio)acetyl]amino]-3-[4-(trifluoro-methoxy)-2-(phenyl)phenylthio]-3-cephem-4-carboxylic acid, sodium salt

Example 155

(7R)-7-[(2-Thienylacetyl)amino]-3-[2-(3,4-dicyanophenyl)phenylthio]-3-cephem-4-carboxylic acid, sodium salt

Example 156

(7R)-7-[(phenylacetyl)amino]-3-[2-(2-furyl)phenylthio]-3-cephem-4-carboxylic acid, sodium salt

Example 157

(7R)-7-[(phenylacetyl)amino]-3-(2-hydroxymethylphenylthio)-3-cephem-4-carboxylate, benzhydryl ester A solution of sodium 2-hydroxymethylbenzenethiolate was prepared by addition of a solution of sodium bis(trimethylsilyl)amide (1.0M in THF, 1.86 mL, 1.86 mmol) to a solution of 2-mercaptobenzyl alcohol (276 mg, 1.96 mmol) in DMF (8 mL). After 10 min, the resulting yellow-orange solution was concentrated with a rotary evaporatory in order to remove the THF. This solution was added dropwise to a stirring solution of (7R)-7-[(phenylacetyl)amino]-3-(trifluoromethanesulfonyloxy)-3-cephem-4-carboxylate, benzhydryl ester (1.00 g, 1.58 mmol) in dry DMF (15 mL) at −45° C. under argon. After 20 min at −45° C., the mixture was quenched by addition of saturated aqueous ammonium chloride solution, and was poured into stirring water (200 mL). After 10 min, the resulting white precipitate was filtered and dried, affording 0.93 g (95%) of the title compound. $^1$H NMR (CDCl$_3$) δ3.03 (d, 1, J=18), 3.09 (d, 1, J=18), 3.62 (d, 1, J=16), 3.66 (d, 1, J=16), 4.72 (d, 1, J=14), 4.76 (d, 1, J=14), 4.97 (d, 1, J=4), 5.75 (dd, 1, J=4,9), 6.05 (d, 1, J=9), 6.98 (s, 1), 7.2–7.6 (m, 19).

Example 158

(7R)-7-[(phenylacetyl)amino]-3-(2-bromomethylphenylthio)-3-cephem-4-carboxylate, benzhydryl ester To a stirring solution of triphenylphosphine (90.5 mg, 0.34 mmol) in THF (5 mL) at room temperature under argon was added carbon tetrabromide (80 mg, 0.24 mmol). After 20 min, to this cloudy white mixture was added a solution of (7R)-7-[(phenylacetyl)amino]-3-(2-hydroxymethylphenylthio)-3-cephem-4-carboxylate, benzhydryl ester (124 mg, 0.20 mmol) in THF (3 mL). After stirring overnight at room temperature, the mixture was concentrated with a rotary evaporator, and the residue was subjected to flash chromatography on silica gel (5 g, 2% methanol/dichloromethane), affording 66 mg (48%) of the title compound. $^1$H NMR (CDCl$_3$) δ3.15 (d, 1, J=18), 3.23 (d, 1, J=18), 3.60 (d, 1, J=16), 3.64 (d, 1, J=16), 4.61 (s, 2), 5.00 (d, 1, J=4), 5.78 (dd, 1, J=4,9), 6.17 (d, 1, J=9), 6.99 (s, 1), 7.2–7.6 (m, 19).

Example 159

(7R)-7-[(phenylacetyl)amino]-3-(2-isothiouroniummethylphenylthio)-3-cephem-4-carboxylate, benzhydryl ester, bromide salt To a stirring solution of (7R)-7-[(phenylacetyl)amino]-3-(2-bromomethylphenylthio)-3-cephem-4-carboxylate, benzhydryl ester (66 mg, 0.096 mmol) in acetonitrile (1 mL) was added thiourea (6.0 mg, 0.079 mmol). After 1.5 h, the mixture was concentrated to a yellow oil and subjected to flash chromatography on silica gel (10% methanol/dichloromethane), affording 30 mg (50%) of the title compound. $^1$H NMR (CDCl$_3$/CD$_3$OD) δ2.80 (d, 1, J=18), 3.31 (d, 1, J=18), 3.63 (s, 2), 4.46 (s, 2), 5.05 (d, 1, J=4), 5.57 (d, 1, J=4), 6.91 (s, 1), 7.1–7.5 (m, 19).

Example 160

(7R)-7-[(phenylacetyl)amino]-3-(2-isothiouroniummethylphenylthio)-3-cephem-4-carboxylic acid, trifluoroacetate salt To a stirring solution of (7R)-7-[(phenylacetyl)amino]-3-(2-isothiouroniummethylphenylthio)-3-cephem-4-carboxylate, benzhydryl ester, bromide salt (30 mg) in dichloromethane (0.5 mL) at 0° C. was added a solution of anisole (0.2 mL) in trifluoroacetic acid (0.4 mL). After 1 h at 0° C., the mixture was concentrated with a rotary evaporator, and the residue was triturated with ether, filtered and dried to afford 11.8 mg of the title compound. $^1$H NMR (CDCl$_3$/CD$_3$OD) δ3.12 (d, 1, J=18), 3.21 (d, 1, J=18), 3.58 (d, 1, J=16), 3.62 (d, 1, J=16), 4.60 (d, 1, J=12), 4.71 (d, 1, J=12), 5.01 (d, 1, J=4), 5.58 (d, 1, J=4), 6.89 (d, 1, J=10), 7.2–7.5 (m, 7) 7.58 (d, 1, J=10).

Example 161

(7R)-7-[(phenylacetyl)amino]-3-(2-hydroxymethylphenylthio)-3-cephem-4-carboxylate, 4-methoxybenzyl ester To a mixture of sodium methoxide (969 mg, 17.9 mmol) in dry THF (50 mL) at 0° C. was added dropwise a solution of 2-mercaptobenzyl alcohol (2.51 g, 17.9 mmol) in dry THF (25 mL). The resulting yellow solution was stirred at 0° C. for 30 min, after which the solvent was removed in vacuo. To the resulting thiolate salt was added (7R)-7-[(phenylacetyl)amino]-3-trifluoromethanesulfonyloxy-3-cephem-4-carboxylate, 4-methoxybenzyl ester (10.0 g, 17.0 mmol), and this solid mixture was cooled to −40° C. Dry DMF (100 mL) at −45° C. was introduced via cannula, and the resulting mixture was stirred at −45° C., forming a yellow solution. After 30 min, the temperature was allowed to rise over 30 min to −10° C., and the mixture was poured into ice water (1 L). After stirring for 15 min, the mixture was filtered, and the precipitate was washed thoroughly with water and air-dried. Further washing with ether afforded the title compound (6.90 g, 71%) as an off-white solid. $^1$H NMR (CDCl$_3$) δ2.43 (br s, 1), 3.06 (d, 1, J=18), 3.15 (d, 1, J=18), 3.60 (d, 1, J=16), 3.63 (d, 1, J=16), 3.81 (s, 3), 4.75 (d, 1, J=14), 4.78 (d, 1, J=14), 4.93 (d, 1, J=4), 5.24 (s, 2), 5.70 (dd, 1, J=4,9), 6.32 (d, 1, J=9), 6.88 (d, 2, J=10), 7.2–7.6 (m, 11).

Example 162

(7R)-7-[(phenylacetyl)amino]-3-(2-bromomethylphenylthio)-3-cephem-4-carboxylate, 4-methoxybenzyl ester This was prepared by a procedure similar to that for example 158, but (7R)-7-[(phenylacetyl)amino]-3-(2-hydroxymethylphenylthio)-3-cephem-4-carboxylate, 4-methoxybenzyl ester was used.

Example 163

(7R)-7-amino-3-(2-bromomethylphenylthio)-3-cephem-4-carboxylate, 4-methoxybenzyl ester To a stirring solution of (7R)-7-[(phenylacetyl)amino]-3-(2-bromomethylphenylthio)-3-cephem-4-carboxylate, 4-methoxybenzyl ester (1.24 g, 1.98 mmol) and pyridine (0.320 mL, 3.96 mmol) in dichloromethane (7 mL) at −10° C. was added slowly a solution of phosphorus pentachloride in dichloromethane (7.32 mL, 3.17 mmol). After 2.5 h at −10° C., the mixture was cooled to −40° C., and isobutanol (1.82 mL, 19.8 mmol) was added. The mixture was allowed to warm to −10° C., was stirred for 1 h, and was partitioned between water and dichloromethane. The organic phase was washed with 10% aqueous HCl and saturated aqueous sodium bicarbonate, dried (sodium sulfate), and concentrated with a rotary evaporator. the resulting beige solid was triturated with ether and dried, affording 504 mg (48%) of the title compound. $^1$H NMR (CD$_3$OD) δ3.26 (d, 1, J=18), 3.42 (d, 1, J=18), 3.58 (s, 3), 4.71 (d, 1, J=8), 4.77 (d, 1, J=8), 4.82 (s, 2), 5.01 (d, 1, J=4), 5.28 (d, 1, J=4), 6.86 (d, 2, J=10), 7.33 (d, 2, J=10), 7.3–7.6 (m, 4).

Example 164

(7R)-7-[(4-bromomethylphenylacetyl)amino]-3-(2-bromomethylphenylthio)-3-cephem-4-carboxylate, 4-methoxybenzyl ester To a stirring suspension of (7R)-7-amino-3-(2-bromomethylphenylthio)-3-cephem-4-carboxylate, 4-methoxybenzyl ester (200 mg, 0.374 mmol) and 4-bromomethylphenylacetic acid (103 mg, 0.449 mmol) in THF (2 mL) at −40° C. was added phosphorus oxychloride (41.7 μL, 0.449 mmol) followed be diisopropylethylamine (0.26 mL, 1.50 mmol). The mixture was allowed to stir overnight at −10° C. Water was added, and the mixture was extracted with dichloromethane. The organic phase was washed with saturated aqueous sodium bicarbonate, 1M phosphoric acid solution, and brine, dried (sodium sulfate), filtered, and concentrated with a rotary evaporator. The crude product was purified by column chromatography on silica gel (0.5% methanol/dichloromethane), affording 168 mg (61%) of the title compound. $^1$H NMR (CDCl$_3$) δ3.15 (d, 1, J=18), 3.27 (d, 1, J=18), 3.61 (s, 2), 3.82 (s, 3), 4.46 (s, 2), 4.65 (d, 1, J=8), 4.68 (d, 1, J=8), 4.95 (d, 1, J=4), 5.26 (s, 2), 5.74 (dd, 1, J=4, 9), 6.20 (d, 1, J=9), 6.86 (d, 2, J=10), 7.2–7.5 (m, 10).

Example 165

(7R)-7-[(4-isothiouroniummethylphenylacetyl)amino]-3-(2-isothiouroniummethylphenylthio)-3-cephem-4-carboxylate, 4-methoxybenzyl ester, dibromide salt To a stirring solution of (7R)-7-[(4-bromomethylphenylacetyl)amino]-3-(2-bromomethylphenylthio)-3-cephem-4-carboxylate, 4-methoxybenzyl ester (168 mg, 0.229 mmol) in acetonitrile (5 mL) was added thiourea (34.9 mg, 0.458 mmol). After stirring overnight at room temperature, the solvent was removed with a rotary evaporator, affording 203 mg (100%) of the title compound as a white-yellow powdery solid. $^1$H NMR (CD$_3$OD) δ4.02 (d, 1, J=18), 4.31 (s, 2), 4.36 (d, 1, J=18), 4.54 (s, 3), 5.25 (s, 2), 5.40 (d, 1, J=10), 5.43 (d, 1, J=10), 5.95 (d, 1, J=12), 5.99 (d, 1, J=12), 6.02 (d, 1, J=4), 6.50 (dd, 1, J=4, 9), 7.65 (d, 2, J=10), 8.0–8.2 (m, 10), 8.39 (d, 1, J=9), 9.97 (m, 8).

Example 166

(7R)-7-[(4-isothiouroniummethylphenylacetyl)amino]-3-(2-isothiouroniummethylphenylthio)-3-cephem-4-carboxylic acid, trifluoroacetate salt To a stirring suspension of (7R)-7-[(4-isothiouromethylphenylacetyl)amino]-3-(2-isothiouroniummethylphenylthio)- 3-cephem-4-carboxylate, 4-methoxybenzyl ester, dibromide salt (203 mg, 0.229 mmol) and anisole (0.1 mL) in dichloromethane (1 mL) at 0° C. was added trifluoroacetic acid (1 mL). A solution formed, the reaction was stirred for 30 min, and the solvent was removed with a rotary evaporator. The residue was dissolved in water (150 mL, with sonication), washed with diethyl ether, and filtered. The filtrate was lyophilized to afford 205 mg of the title compound. $^1$H NMR (D$_2$O) δ3.20 (d, 1, J=18), 3.38 (d, 1, J=18), 3.61 (s, 2), 4.40 (s, 2), 4.61 (d, 1, J=8), 4.64 (d, 1, J=8), 5.15 (d, 1, J=4), 5.59 (d, 1, J=4), 7.2–7.6 (m, 8).

Example 167

(7R)-7-[(phenylacetyl)amino]-3-(2-phenylpyrid-3-ylthio)-3-cephem-4-carboxylate, benzhydryl ester A mixture of 2-bromo-3-hydroxypyridine (2.20 g, 12.6 mmol), phenylboronic acid (2.00 g, 16.3 mmol) and palladium (tetrakis)triphenylphosphine (250 mg) in toluene (30 mL), ethanol (15 mL) and 5% aqueous sodium hydroxide (15 mL) was degassed with a stream of nitrogen and stirred vigorously at 100° C. overnight. The mixture was diluted with water (50 mL) and ethyl acetate (100 mL), and the organic layer was dried over sodium sulfate and concentrated, affording a yellow solid. This material was suspended in water (100 mL), a few mL of 1N HCl was added, and the resulting solution was extracted with ethyl acetate. The aqueous layer was neutralized with saturated aqueous sodium bicarbonate, and again was extracted with ethyl acetate. The combined organic extracts were dried with sodium sulfate and concentrated to an oily solid, which was triturated with 2:1 hexane/ethylacetate, affording 0.98 g of 3-hydroxy-2-phenylpyridine.

To a stirring solution of 3-hydroxy-2-phenylpyridine (425 mg, 2.48 mmol) in DMF (8 mL) at room temperature was added a solution of sodium bis(trimethylsilyl)amide in DMF (2M, 1.36 mL, 2.72 mmol). After a few minutes, to this mixture was added a solution of N,N-dimethylthiocarbamoyl chloride (338 mg, 2.72 mmol) in DMF (2 mL). After stirring overnight, the mixture was partitioned between water and ethyl acetate, and the organic phase was concentrated and subjected to flash chromatography on silica gel, affording 536 mg of 3-N,N-dimethylthiocarbamoyl-2-phenylpyridine. $^1$H NMR (CDCl$_3$) $\delta$3.23 (s, 3), 3.40 (s, 3), 7.3–7.7 (m, 7), 8.60 (d, 1, J=6). This material was heated in a sealed vial at 250°–255° C. for 1.5 h. The product was dissolved in ethanol (10 mL), 10% aqueous potassium hydroxide was added (4 mL), and the resulting mixture was heated under nitrogen at 95°–100° C. for 2 h. The mixture was partitioned between ethyl acetate and aqueous acetic acid, the organic phase was concentrated, and the residue was subjected to chromatography on silica gel, eluting with 6:1 hexane/ethyl acetate, affording 337 mg of 3-mercapto-2-phenylpyridine. $^1$H NMR (CDCl$_3$) $\delta$3.47 (s, 1), 7.11 (m, 1), 7.45 (m, 3), 7.64 (m, 3), 8.47, (d, 1, J=5).

To a stirring solution of 3-mercapto-2-phenylpyridine (65 mg, 0.35 mmol) in DMF (1 mL) at 0° C. was added a solution of sodium bis(trimethylsilyl)amide in THF (0.175 mL of 2M solution, 0.35 mmol). The resulting solution was transferred via cannula into a stirring solution of (7R)-7-[(phenylacetyl)amino]-3-(trifluoromethanesulfonyloxy)-3-cephem-4-carboxylate, benzhydryl ester (233 mg, 0.368 mmol) in DMF (5 mL) at −40° C. After 30 min at −40° C., the reaction was quenched by addition of 10% aqueous ammonium chloride solution, and the mixture was partitioned between water and ethyl acetate. The organic phase was dried over sodium sulfate, and was concentrated with a rotary evaporator. The crude product was purified by chromatography on silica gel (5% methanol/dichloromethane) to afford 165 mg of the title compound. $^1$H NMR (CDCl$_3$) $\delta$3.02 (d, 1, J=18 ), 3.23 (d, 1, J=18), 3.61 (d, 1, J=16), 3.64 (d, 1, J=16), 4.81 (d, 1, J=4), 5.79 (dd, 1, J=4,9), 6.20 (d, 1, J=9), 7.01 (s, 1), 7.2–7.6 (m, 21), 7.67 (d, 1, J=10), 8.61 (d, 1, J=5).

Example 168

(7R)-7-[(phenylacetyl)amino]-3-(2-phenylpyrid-3-ylthio)-3-cephem-4-carboxylic acid, trifluoroacetic acid salt To a stirring solution of (7R)-7-[(phenylacetyl)amino]-3-(2-phenylpyrid-3-ylthio)-3-cephem-4-carboxylate, benzhydryl ester (32 mg) and anisole (0.1 mL) in dichloromethane (1 mL) at 0° C. was added trifluoroacetic acid (1 mL). After 0.5 h at 0° C., the mixture was concentrated with a rotary evaporator. The crude product was triturated with ether, filtered, and dried to afford 20.1 mg of the title compound as an off-white solid. $^1$H NMR (CD$_3$OD) $\delta$3.22 (d, 1, J=18), 3.49 (d, 1, J=18), 3.55 (d, 1, J=16), 3.60 (d, 1, J=16), 5.03 (d, 1, J=5), 5.71 (d, 1, J=5), 7.27 (m, 5), 7.55 (m, 3), 7.60 (m, 3), 8.08 (d, 1, J=10), 8.59 (d, 1, J=5).

Example 169

(7R)-7-[(phenylacetyl)amino]-3-(2-cyanopyrid-3-ylthio)-3-cephem-4-carboxylate, 4-methoxybenzyl ester To a solution of 3-hydroxypicolinamide (2.00 g, 14.5 mmol) in phosphorus oxychloride (10 mL) at room temperature was added phosphorus pentachloride (6.00 g, 28.8 mmol). The mixture was heated at reflux for 90 min, and the solvent was removed by distillation. The residue was poured into water, the aqueous solution was neutralized by addition of sodium bicarbonate, and was extracted with ethyl acetate. The organic phase was filtered through silica gel, the filtrate was concentrated, and the residue was subjected to flash chromatography on silica gel, affording 300 mg of 3-chloro-2-cyanopyridine. $^1$H NMR (CDCl$_3$) $\delta$7.50 (dd, 1, J=4.8, 8.4), 7.89 (dd, 1, J=1.6, 8.4), 8.63 (dd, 1, J=1.6, 4.8).

To a stirring solution of 4-methoxy-α-toluenethiol (268 mg, 1.74 mmol) in DMF (1 mL) at 0° C. was added a solution of sodium bis(trimethylsilyl)amide in THF (1.3 mL, 1M, 1.3 mmol). The resulting solution was added via cannula to a solution of 2-cyano-3-chloropyridine (200 mg, 1.45 mmol) in DMF (1 mL) at 0° C. After stirring for 2 h at 0° C., the mixture was poured into water and extracted with ethyl acetate, and the organic extracts were concentrated. The crude product was purified by column chromatography on silica gel, affording 2-cyano-3-(4-methoxybenzylthio)pyridine in quantitative yield. $^1$H NMR (CDCl$_3$) $\delta$3.80 (s, 3), 4.20 (s, 2), 6.83 (d, 2, J=10), 7.22 (d, 2, J=10), 7.34 (dd, 1, J=5, 8), 7.66 (d, 1, J=8), 8.50 (d, 1, J=5). To a solution of this compound (245 mg, 0.96 mmol) and anisole (0.52 mL, 4.8 mmol) in trifluoroacetic acid (1.5 mL) at 0° C. was added trifluoromethanesulfonic acid (0.25 mL, 2.8 mmol). The mixture was allowed to warm to room temperature, and was stirred for 1 h. The solvent was removed with a rotary evaporator, and the residue was purified by flash chromatography on silica gel, affording 117 mg (90%) of 2-cyano-3-mercaptopyridine. $^1$H NMR (CDCl$_3$) $\delta$4.15 (s, 1), 7.39 (dd, 1, J=5, 8), 7.78 (d, 1, J=8), 8.48 (d, 1, J=5).

To a stirring solution of 2-cyano-3-mercaptopyridine (42 mg, 0.30 mmol) in dichloromethane (3 mL) at 0° C. was added a solution of sodium bis(trimethylsilyl)amide in THF (0.29 mL of 1M solution, 0.29 mmol). This solution was added dropwise via cannula to a stirring slurry of (7R)-7-[(phenylacetyl)amino]-3-(trifluoromethanesulfonyloxy)-3-cephem-4-carboxylate, 4-methoxybenzyl ester (200 mg, 0.34 mmol) in dichloromethane (1 mL) at −40° C. The mixture was allowed to warm to room temperature and was stirred for 1 h, whereupon it was filtered through a pad of silica gel, washing with 1:1 dichloromethane/ethyl acetate. After concentrating the filtrate, the product was purified by flash chromatography on silica gel, affording 158 mg (90%) of the title compound. $^1$H NMR (CDCl$_3$) $\delta$3.15 (d, 1, J=18), 3.60 (d, 1, J=18), 3.63 (d, 1, J=16), 3.68 (d, 1, J=16), 3.80 (s, 3), 5.04 (d, 1, J=4), 5.15 (d, 1, J=12), 5.27 (d, 1, J=12), 5.90 (dd, 1, J=4, 9), 6.00 (d, 1, J=9), 6.81 (d, 2, J=10), 7.2–7.5 (m, 8), 7.70 (d, 1, J=8), 8.55 (d, 1, J=5).

Example 170

(7R)-7-[(phenylacetyl)amino]-3-(2-cyanopyrid-3-ylthio)-3-cephem-4-carboxylic acid To a stirring solution of (7R)-7-[(phenylacetyl)amino]-3-(2-cyanopyrid-3-ylthio)-3-cephem-4-carboxylate, 4-methoxybenzyl ester (158 mg, 0.277 mmol) and anisole (0.4 mL) in dichloromethane (1 mL) at 0° C. was added trifluoroacetic acid (1 mL). After 1 h at 0° C., the solvent was removed with a rotary evaporator, and the residue was triturated with ether, filtered, and dried, affording 104 mg (83%) of the title compound. $^1$H NMR (CDCl$_3$) $\delta$3.15 (d, 1, J=18), 3.54 (d, 1, J=18), 3.65 (d, 1, J=16), 3.69 (d, 1, J=16), 5.07 (d, 1, J=4), 5.89 (dd, 1, J=4, 9), 6.18 (d, 1, J=9), 7.2–7.4 (m, 5), 7.53 (dd, 1, J=5, 8), 7.90 (d, 1, J=8), 8.66 (d, 1, J=5).

Example 171

(7R)-7-[(phenylacetyl)amino]-3-(1-phenylpyrazol-1-5-ylthio)-3-cephem-4-carboxylate, 4-methoxybenzyl ester To a stirring solution of 1-phenylpyrazole (1.44 g, 10.0 mmol) in THF (7 mL) at −30° C. was added a solution of n-butyllithium in hexane (1.6M, 6.88 mL, 11.0 mmol). After 30 min at −30° C., sulfur (352 mg, 11.0 mmol) was added, and the mixture was allowed to warm to 0° C. and stir for 7 h. Saturated aqueous ammonium chloride solution and 10% aqueous HCl were added, and the mixture was extracted with ethyl acetate. The organic layer was extracted with 5% aqueous potassium carbonate solution; the aqueous phase was acidified with 10% aqueous HCl and extracted with ethyl acetate, and the organic phase was dried (sodium sulfate), filtered, and concentrated, affording 1.03 g of 5-mercapto-1-phenylpyrazole. $^1$H NMR (CDCl$_3$) δ3.42 (s, 1), 6.50 (d, 2), 7.4–7.6 (m, 5), 7.67 (d, 2).

To a stirring solution of 5-mercapto-1-phenylpyrazole (396 mg, 2.25 mmol) in THF (3 mL) at 0° C. was added a solution of sodium bis(trimethylsilyl)amide in THF (2M, 1.02 mL, 2.04 mmol). After 5 min, the solvent was removed in vacuo, the residue was dissolved in DMF (3 mL), and the resulting solution was added via syringe to a stirring solution of (7R)-7-[(phenylacetyl)amino]-3-(trifluoromethanesulfonyloxy)-3-cephem-4-carboxylate, 4-methoxybenzyl ester (1.20 g, 2.04 mmol) in DMF (10 mL) at −50° C. After 10 min at −50° C., saturated aqueous ammonium chloride solution was added, and the mixture was poured into water at 0° C. and stirred for 1 h. The precipitated product was collected by filtration and was recrystallized from isopropanol, affording 856 mg (68%) of the title compound. $^1$H NMR (CDCl$_3$) δ2.93 (d, 1, J=18), 2.99 (d, 1, J=18), 3.59 (d, 1, J=16), 3.63 (d, 1, J=16), 3.81 (s, 3), 4.63 (d, 1, J=4), 5.18 (d, 1, J=12), 5.22 (d, 1, J=12), 5.66 (dd, 1, J=4, 9), 5.95 (d, 1, J=9), 6.70 (d, 1, J=2), 6.90 (d, 2, J=10), 7.2–7.5 (m, 12), 7.76 (d, 1, J=2).

Example 172

(7R)-7-[(phenylacetyl)amino]-3-(1-phenylpyrazol-5-ylthio)-3-cephem-4-carboxylic acid To a stirring solution of (7R)-7-[(phenylacetyl)amino]-3-(1-phenylpyrazol-5-ylthio)-3-cephem-4-carboxylate, 4-methoxybenzyl ester (80 mg, 0.12 mmol ) and anisole (0.02 mL) in dichloromethane (2 mL) at 0° C. was added trifluoroacetic acid (0.5 mL). After 2 h at 0° C., the solvent was removed with a rotary evaporator, and the residue was subjected to chromatography on silica gel (3% acetic acid/ethyl acetate), affording 49 mg (83%) of the title compound. $^1$H NMR (acetone-d$_6$) δ3.21 (s, 2), 3.60 (d, 1, J=16), 3.65 (d, 1, J=16), 4.96 (d, 1, J=4), 5.71 (dd, 1, J=4, 9), 6.83 (d, 1, J=2), 7.2–7.6 (m, 10), 7.80 (d, 1, J=2), 8.05 (d, 1, J=9).

Example 173

(7R)-7-amino-3-(1-phenylpyrazol-5-ylthio)-3-cephem-4-carboxylate, 4-methoxybenzyl ester, hydrochloride salt To a stirring solution of (7R)-7-[(phenylacetyl)amino]-3-(1-phenylpyrazol-5-ylthio)-3-cephem-4-carboxylate, 4-methoxybenzyl ester (1.60 g, 2.61 mmol) and pyridine (0.53 mL, 6.5 mmol) in dry dichloromethane (10 mL) at 0° C. was added a solution of phosphorus pentachloride (1.09 g, 5.2 mmol) in dichloromethane (12 mL). After 2.5 h at 0° C., isobutanol (2.4 mL, 26 mmol) was added, and the mixture was stirred for 1.5 h. Water was added, the layers were separated, and the organic phase was washed with 5% aqueous sodium bicarbonate and 5% aqueous HCl, dried over sodium sulfate, filtered, and concentrated with a rotary evaporator. The resulting yellow oil was triturated with ether, filtered and dried to afford 1.25 g (90%) of the title compound. $^1$H NMR (CDCl$_3$/CD$_3$OD) δ2.74 (d, 1, J=18), 3.17 (d, 1, J=18), 4.65 (d, 1, J=4), 4.84 (d, 1, J=4), 6.65 (d, 1, J=2), 6.75 (d, 2, J=9), 7.20 (d, 2, J=9), 7.2–7.4 (m, 5), 7.64 (d, 1, J=2).

Example 174

(7R)-7-[(cyanoacetyl)amino]-3-(1-phenylpyrazol-5-ylthio)-3-cephem-4-carboxylate, 4-methoxybenzyl ester To a stirring solution of (7R)-7-amino-3-(1-phenylpyrazol-5-ylthio)-3-cephem-4-carboxylate, 4-methoxybenzyl ester, hydrochloride salt (110 mg, 0.222 mmol) and cyanoacetic acid (36 mg, 0.42 mmol) in dry THF (4 mL) at −30° C. was added diisopropylethylamine (0.19 mL, 1.11 mmol) followed by phosphorus oxychloride (39.5 μL, 0.42 mmol). After 1 h at −20° C., the mixture was partitioned between water and ethyl acetate. The organic phase was washed with 5% aqueous sodium bicarbonate and 5% aqueous HCl, dried over sodium sulfate, and concentrated. The crude product was purified by chromatography on silica gel (1% methanol/dichloromethane), affording 105 mg (85%) of the title compound. $^1$H NMR (CDCl$_3$) δ2.93 (d, 1, J=18), 3.09 (d, 1, J=18), 3.40 (s, 2), 3.81 (s, 3), 4.67 (d, 1, J=4), 5.20 (d, 1, J=12), 5.22 (d, 1, J=12), 5.61 (dd, 1, J=4, 9), 6.72 (d, 1, J=2), 6.87 (d, 2, J=10), 7.10 (d, 1, J=9), 7.3–7.5 (m, 7), 7.76 (d, 1, J=2).

Example 175

(7R)-7-[(cyanoacetyl)amino]-3-(1-phenylpyrazol-5-ylthio)-3-cephem-4-carboxylic acid, sodium salt To a stirring solution of (7R)-7-[(cyanoacetyl)amino]-3-(1-phenylpyrazol-5-ylthio)-3-cephem-4-carboxylate, 4-methoxybenzyl ester (105 mg, 0.187 mmol) and anisole (0.02 mL) in dichloromethane (2 mL) at 0° C. was added trifluoroacetic acid (0.5 mL). After 1 h at 0° C., the solvent was removed with a rotary evaporator. The residue was taken up in aqueous sodium bicarbonate, and was subjected to reverse-phase chromatography on C(18), eluting with water followed by 20% acetonitrile/water. The fractions containing the desired product were lyophilized, affording 47.5 mg (50%) of the title compound. A sample was treated with HCl and dried for $^1$H NMR analysis. $^1$H NMR (acetone-d$_6$) δ3.24 (d, 1, J=18), 3.30 (d, 1, J=18), 3.79 (s, 2), 5.06 (d, 1, J=4), 5.76 (d, 1, J=4), 6.87 (d, 1, J=2), 7.4–7.6 (m, 5), 7.82 (d, 1, J=2).

Example 176

(7R)-7-[(phenylacetyl)amino]-3-(1-(pyrid-2-yl)pyrazol-5-ylthio)-3-cephem-4-carboxylate, 4-methoxybenzyl ester To a stirring solution of 2-pyridylhydrazine (3.30 g, 30.2 mmol) and malonaldehyde bis(dimethylacetal) (4.96 g, 30.2 mmol) in absolute ethanol (60 mL) at room temperature was added concentrated HCl until the mixture was acidic (3 mL). The mixture was heated at reflux for 3 h, and was allowed to cool to room temperature. The mixture was concentrated with a rotary evaporator, and the residue was triturated with ether and filtered. The remaining solid was dissolved in water, basified with saturated aqueous sodium bicarbonate, and extracted with ethyl acetate. The organic extracts were washed with water and brine, dried (sodium sulfate), and concentrated with a rotary evaporator to afford 3.10 g (70%) of 1-(pyrid-2-yl)pyrazole. $^1$H NMR (CDCl$_3$) δ6.48 (dd, 1, J=1, 2), 7.20 (dd, 1, J=8, 10), 7.75 (d, 1, J=1), 7.82 (dt, 1, J=2, 10), 8.00 (d, 1, J=10), 8.42 (dd, 1, J=2, 8), 8.59 (d, 1, J=2).

To a stirring solution of 1-(pyrid-2-yl)pyrazole (1.00 g, 6.88 mmol) in THF (20 mL) at −78° C. was added a solution of n-butyllithium in hexanes (4.70 mL, 1.6M, 7.52 mmol). After 15 min at −78° C., sulfur (243 mg, 7.59 mmol) was added. The mixture was stirred at −78° C. for 15 min, and was warmed to 0° C., and stirred for 30 min. Water was added, and the THF was removed with a rotary evaporator. The residue was washed with ethyl acetate, acidified to pH 6, and extracted with ethyl acetate. The latter organic extract was washed with brine, dried (sodium sulfate), and concentrated with a rotary evaporator, affording 873 mg (73%) of 5-mercapto-1-(pyrid-2-yl)pyrazole. $^1$H NMR (CDCl$_3$) δ6.20 (br s, 1), 6.30 (d, 1, J=2), 7.22 (dd, 1, J=8, 10), 7.63 (d, 1, J=2), 7.87 (dt, 1, J=2, 10), 8.01 (d, 1, J=10), 8.44 (dd, 1, J=2, 8).

To a stirring solution of 5-mercapto-1-(pyrid-2-yl)pyrazole (95 mg, 0.540 mmol) in DMF (2 mL) at 0° C. was added a solution of sodium bis(trimethylsilylamide) in THF (0.40 mL, 1M, 0.40 mmol). This solution was added to a solution of (7R)-7-[(phenylacetyl)amino]-3-(trifluoromethanesulfonyloxy)-3-cephem-4-carboxylate, 4-methoxybenzyl ester (235 mg, 0.400 mmol) in DMF (12 mL) at −40° C. After 20 min at −40° C., the reaction was quenched by addition of saturated aqueous ammonium chloride solution (2 mL) and water. The mixture was extracted twice with ethyl acetate, and the organic extracts were washed with water and brine, and were dried over sodium sulfate and concentrated with a rotary evaporator, affording 240 mg (98%) of the title compound, containing ~10% of the Δ2 isomer. $^1$H NMR (acetoned-d$_6$) δ3.54 (d, 1, J=18), 3.63 (d, 1, J=16), 3.70 (d, 1, J=16), 3.78 (s, 3), 3.80 (d, 1, J=18), 5.17 (d, 1, J=10), 5.21 (d, 1, J=10), 5.25 (d, 1, J=4), 5.90 (dd, 1, J=4, 9), 6.33 (d, 1, J=2), 6.80 (d, 2, J=12), 7.2–7.4 (m, 8), 7.74 (d, 1, J=2), 7.94 (d, 1, J=10), 8.03 (dt, 1, J=2, 10), 8.20 (d, 1, J=9), 8.46 (dd, 1, J=2, 8).

Example 177

(7R)-7-[(phenylacetyl)amino]-3-(1-(pyrid-2-yl)pyrazol-5-ylthio)-3-cephem-4-carboxylic acid To a stirring suspension of (7R)-7-[(phenylacetyl)amino]-3-(1-(pyrid-2-yl)pyrazol-5-ylthio)-3-cephem-4-carboxylate, 4-methoxybenzyl ester (100 mg, 0.16 mmol) and anisole (0.6 mL) in dichloromethane (1.2 mL) at 0° C. was added trifluoroacetic acid (1.2 mL). After 30 min at 0° C., the solvent was removed with a rotary evaporator. The residue was dissolved in ethyl acetate, and was extracted with saturated aqueous sodium bicarbonate. The aqueous extracts were washed with ether, and were then acidified to pH 4–5 using aqueous HCl. This was extracted with ethyl acetate, and the organic extracts were washed with water and brine, and were dried (sodium sulfate) and concentrated. The resulting oil was triturated with hexane to afford the title compound (60 mg, 75%) as a pale yellow solid. $^1$H NMR (acetone-d$_6$) δ3.55 (d, 1, J=18), 3.63 (d, 1, J=16), 3.71 (d, 1, J=16), 3.79 (d, 1, J=18), 5.25 (d, 1, J=4), 5.89 (dd, 1, J=4, 9), 6.44 (d, 1, J=2), 7.2–7.4 (m, 6), 7.78 (d, 1, J=2), 7.92 (d, 1, J=10), 8.02 (dt, 1, J=2, 10), 8.18 (d, 1, J=9), 8.48 (dd, 1, J=2, 8).

Example 178

(7R)-7-[(phenylacetyl)amino]-3-(2-(pyrazol-1-yl)pyrid-3-ylthio)-3-cephem-4-carboxylate, 4-methoxybenzyl ester A mixture of 2-chloro-3-nitropyridine (942 mg, 5.94 mmol), pyrazole (967 mg, 14.2 mmol) and powdered potassium carbonate (2 g) in DMF (10 mL) was stirred vigorously at room temperature for 4 days. The mixture was diluted with water, causing precipitation of a solid, which was filtered and dried, affording 670 mg (63%) of 3-nitro-2-(pyrazol-1-yl) pyridine. $^1$H NMR (CDCl$_3$) δ6.51 (m, 1), 7.37 (dd, 1 J=5, 8), 7.76 (m, 1) 8.03 (dd, 1, J=2, 8), 8.40 (m, 1), 8.60 (dd, 1, J=2, 5).

To a suspension of 3-nitro-2-(pyrazol-1-yl) pyridine (670 mg, 3.72 mmol) in ethanol (10 mL) was added a 1M solution of SnCl$_2$.H$_2$O in 6N aqueous HCl (14.5 mL, 14.5 mmol). The mixture was heated at reflux for 10 min, and the solvent was removed with a rotary evaporator. 10% aqueous sodium hydroxide solution was added until most of the material dissolved, and the mixture was extracted with dichloromethane. The organic extracts were dried over sodium sulfate and concentrated to afford 376 mg (68%) of 3-amino-2-(pyrazol-1-yl) pyridine as a brown oil. $^1$H NMR (CDCl$_3$) δ5.62 (br s, 2), 6.46 (m, 1), 7.05 (dd, 1, J=5, 8), 7.24 (dd, 1, J=2, 8), 7.74 (m, 1), 7.85 (dd, 1, J=2, 5), 8.54 (d, 1, J=3).

To a stirring solution of 3-amino-2-(pyrazol-1-yl)pyridine (376 mg, 2.50 mmol) in 3M aqueous HCl (4.3 mL) at 0° C. was added over 10 mina solution of sodium nitrite (181 mg, 2.63 mmol) in water (1 mL). After 30 min, this solution was added to a solution of potassium ethyl xanthate (800 mg, 5.0 mmol) in water/saturated aqueous sodium bicarbonate (1:1, 22 mL) at 60° C. The mixture was heated at 60° C. for 10 min, and was extracted with ethyl acetate, dried over sodium sulfate, and concentrated. The crude product was purified by silica gel chromatography (hexane/ethyl acetate 4:1), affording 250 mg of the ethyl xanthate derivative. This material was dissolved in ethanol (4 mL) and was treated with 30% aqueous sodium hydroxide (2 mL) After 3 h, the mixture was neutralized by addition of 0.5M citric acid solution, extracted with ethyl acetate, dried over sodium sulfate, and concentrated. The crude product was purified by silica gel chromatography, affording 166 mg (40%) of 3-mercapto-2-(pyrazol-1-yl)pyridine. $^1$H NMR (CDCl$_3$) δ5.92 (br s, 1), 6.47 (m, 1), 7.08 (dd, 1, J=5, 8), 7.72 (dd, 1, J=2, 8), 7.78 (m, 1), 8.21 (dd, 1, J=2, 5), 8.42 (d, 1, J=3).

To a solution of 3-mercapto-2-(pyrazol-1-yl)pyridine (77 mg, 0.435 mmol) in DMF (1 mL) at room temperature was added a 1M solution of sodium bis(trimethylsilyl)amide in THF (0.42 mL, 0.42 mmol). After 10 min, this solution was transferred via cannula into a solution of (7R)-7-[(phenylacetyl)amino]-3-(trifluoromethanesulfonyloxy)-3-cephem-4-carboxylate, 4-methoxybenzyl ester (267 mg, 0.457 mmol) in DMF (2 mL) at –40° C. After 1 h at –40° C., the mixture was poured into water and extracted with ethyl acetate. The organic extracts were washed with water, dried over sodium sulfate, and concentrated with a rotary evaporator. The residue was triturated with 1:1 hexane/ethyl acetate and dried, affording 291 mg of the title compound. $^1$H NMR (CDCl$_3$) δ3.10 (d, 1, J=18), 3.52 (d, 1, J=18), 3.65 (d, 1, J=16), 3.69 (d, 1, J=16), 3.75 (s, 3), 5.01 (d, 1, J=4), 5.26 (d, 1, J=12), 5.28 (d, 1, J=12), 5.89 (dd, 1, J=4, 9), 6.05 (d, 1, J=9), 6.50 (m, 1), 6.72 (d, 2, J=10), 7.13 (dd, 1, J=5, 8), 7.20 (d, 2, J=10), 7.2–7.4 (m, 5), 7.59 (dd, 1, J=2, 8), 7.78 (m, 1), 8.28 (dd, 1, J=2, 5), 8.40 (m, 1).

Example 179

(7R)-7-[(phenylacetyl)amino]-3-(2-(pyrazol-1-yl)pyrid-3-ylthio)-3-cephem-4-carboxylic acid, sodium salt To a stirring solution of (7R)-7-[(phenylacetyl)amino]-3-(2-(pyrazol-1-yl)pyrid-3-ylthio)-3-cephem-4-carboxylate, 4-methoxybenzyl ester (80 mg) and anisole (0.1 mL) in dichloromethane (1 mL) at 0° C. was added trifluoroacetic acid (1 mL). After 30 min at 0° C., the mixture was concentrated to an oil, and was partitioned between ether and saturated aqueous sodium bicarbonate. The aqueous phase was subjected to reverse phase chromatography on C(18), eluting with water followed by acetonitrile/water. The fractions containing product were lyophilized, affording 43 mg of the title compound. $^1$H NMR (D$_2$O) δ3.10 (d, 1, J=18), 3.50 (d, 1, J=18), 3.64 (d, 1, J=16), 3.69 (d, 1, J=16), 5.10 (d, 1, J=4), 5.62 (d, 1, J=4), 6.61 (m, 1), 7.2–7.4 (m, 5), 7.52 (m, 1), 7.82 (m, 1), 7.93 (br d, J=8), 8.14 (m, 1), 8.37 (m, 1).

Example 180

(7R)-7-[(phenylacetyl)amino]-3-[2-(N,N'-(bis)tert-butyloxycarbonylguanidinomethyl)phenylthio]-3-cephem-4-carboxylate, 4-methoxybenzyl ester To a stirring solution of 2-mercaptobenzyl alcohol (1.00 g, 7.10 mmol) in dichloromethane (20 mL) at 0° C. was added methyl acrylate (0.70 mL, 7.70 mmol) followed by triethylamine (50 μL, 0.35 mmol). The mixture was allowed to warm to room temperature and stir for 4 h, at which point the solvent was removed with a rotary evaporator. The residue was subjected to column chromatography on silica gel (0–10% ethyl acetate in dichloromethane), affording 1.40 g (86%) of methyl 3-(2-hydroxymethylphenylthio)propionate. $^1$H NMR (CDCl$_3$) δ2.63 (t, 2, J=7), 3.18 (t, 2, J=7), 3.68 (s, 3), 4.79 (s, 2), 7.27 (m, 2), 7.43 (m, 2).

To a stirring solution of methyl 3-(2-hydroxymethylphenylthio)propionate (1.40 g, 5.10 mmol), triphenylphosphine (2.00 g, 7.60 mmol), and N,N'-(bis)tert-butyloxycarbonylguanidine (2.60 g, 10.2 mmol) in THF (30 mL) at 0° C. was slowly added diisopropyl azodicarboxylate (1.50 mL, 7.60 mmol). The mixture was allowed to warm to room temperature and was stirred for 5 h. The solvent was removed with a rotary evaporator, and the residue was subjected to column chromatography on silica gel, affording 1.62 g (68%) of methyl 3-[2-(N,N'-(bis) tert-butyloxycarbonylguanidinomethyl)phenylthio]propionate. $^1$H NMR (CDCl$_3$) δ1.25 (s, 9), 1.46 (s, 9), 2.62 (t, 2, J=7), 3.13 (t, 2, J=7), 3.69 (s, 3), 5.39 (s, 2), 7.0–7.4 (m, 4), 9.42 (br s, 1), 9.53 (br s, 1).

To a stirring solution of methyl 3-[2-(N,N'-(bis)tert-butyloxycarbonylguanidinomethyl)phenylthio]propionate (63 mg, 0.13 mmol) in DMF (1 mL) at room temperature was added potassium tert-butoxide (15 mg, 0.13 mmol). After 4 h, this mixture was transferred by cannula into a stirring solution of (7R)-7-[(phenylacetyl)amino]-3-trifluoromethanesulfonyloxy-3-cephem-4-carboxylate, 4-methoxybenzyl ester (79 mg, 0.13 mmol) in DMF (0.5 mL) at –40° C. The mixture was stirred for 40 min at –40° C., and was quenched by addition of saturated ammonium chloride solution. The mixture was extracted with ethyl acetate/hexane, and the organic phase was dried over sodium sulfate and concentrated with a rotary evaporator. Column chromatography on silica gel (50% ethyl acetate in hexane) afforded 44 mg (40%) of the title compound. $^1$H NMR (CDCl$_3$) δ1.28 (s, 9), 1.42 (s, 9), 3.05 (d, 1, J=18), 3.33 (d, 1, J=18), 3.59 (d, 1, J=16), 3.62 (d, 1, J=16), 3.81 (s, 3), 5.00 (d, 1, J=4), 5.07 (d, 1, J=18), 5.26 (s, 2), 5.32 (d, 1, J=18), 5.78 (dd, 1, J=4,9), 6.15 (d, 1, J=9), 6.89 (d, 2, J=12), 7.03 (d, 1, J=10), 7.2–7.4 (m, 9), 7.52 (d, 1, J=10), 9.39 (br s, 1), 9.44 (br s, 1).

Example 181

(7R)-7-[(phenylacetyl)amino]-3-[2-(guanidinomethyl)phenylthio]-3-cephem-4-carboxylate, inner salt To a stirring solution of (7R)-7-[(phenylacetyl)amino]-3-[2-(N,N'-(bis)tert-butyloxycarbonylguanidinomethyl) phenylthio]-3-cephem-4-carboxylate, 4-methoxybenzyl ester (44 mg, 0.055 mmol) and anisole (0.2 mL) in dichloromethane (0.4 mL) at 0° C. was added trifluoroacetic acid (1 mL). The mixture was allowed to warm to room temperature and stir for 40 min. The solvent was removed in vacuo, and the residue was triturated with ether and filtered, affording the title compound (25 mg, 95%) as a light yellow powder. $^1$H NMR (CD$_3$OD) δ3.10 (d, 1, J=17), 3.41 (d, 1, J=17), 3.54 (d, 1, J=12), 3.58 (d, 1, J=12), 4.48 (s, 2), 5.04 (d, 1, J=5), 5.59 (d, 1, J=5), 7.2–7.4 (m, 9).

Example 182

(7R)-7-[(phenylacetyl)amino]-3-(2-chloromethylphenylthio)-3-cephem-4-carboxylate, 4-methoxybenzyl ester To dry DMF (100 mL) at 0° C. was added thionyl chloride (1.3 mL, 17.8 mmol). After 30 min at 0° C., to this solution was added (7R)-7-[(phenylacetyl)amino]-3-(2-hydroxymethylphenylthio)-3-cephem-4-carboxylate, 4-methoxybenzyl ester (6.90 g, 12.0 mmol). The resulting solution was stirred at 0° C. for 30 min, and was poured into ice water (800 mL). After 30 min, the mixture was filtered, and the precipitate was washed with water and air-dried. The resulting pale brown solid was taken up in dichloromethane (500 mL), washed with water and saturated aqueous sodium chloride solution, dried over sodium sulfate, filtered, and concentrated with a rotary evaporator. The residue was triturated with ether, filtered and dried to afford the title compound (4.35 g, 61%) as an off-white solid. $^1$H NMR (CDCl$_3$) δ3.08 (d, 1, J=18), 3.25 (d, 1, J=18), 3.60 (d, 1, J=16), 3.63 (d, 1, J=16), 3.81 (s, 3), 4.75 (d, 1, J=14), 4.79 (d, 1, J=14), 4.94 (d, 1, J=4), 5.25 (s, 2), 5.75 (dd, 1, J=4,9), 6.04 (d, 1, J=9), 6.86 (d, 2, J=10), 7.2–7.6 (m, 11).

Example 183

(7R)-7-amino-3-(2-chloromethylphenylthio)-3-cephem-4-carboxylate, 4-methoxybenzyl ester, trifluoroacetate salt To a stirring solution of (7R)-7-[(phenylacetyl)amino]-3-(2-chloromethylphenylthio)-3-cephem-4-carboxylate, 4-methoxybenzyl ester (11.6 g, 19.5 mmol) and pyridine (3.20 mL, 39.6 mmol) in dichloromethane (50 mL) at 0° C. was added slowly a solution of phosphorus pentachloride (6.40 g, 30.7 mmol) in dichloromethane (75 mL). After 2 h at 0° C., isobutanol (1.82 mL, 19.8 mmol) was added. The mixture stirred for 2 h at 0° C., dichloromethane was added (500 mL), and the resulting solution was washed with saturated aqueous sodium bicarbonate (2×400 mL), water (2×400 mL), 1M aqueous HCl (2×400 mL), and brine (2×400 mL). The organic phase was dried (sodium sulfate), trifluoroacetic acid (1.6 mL, 20.8 mmol) was added, and the mixture was concentrated with a rotary evaporator. The resulting beige solid was triturated with ether and dried, affording the title compound (6.53 g, 57%) as a pale brown solid. $^1$H NMR (CDCl$_3$/CD$_3$OD) δ2.85 (d, 1, J=18), 3.34 (d, 1, J=18), 3.72 (s, 3), 4.62 (d, 1, J=8), 4.74 (d, 1, J=8), 4.74 (m, 1), 5.06 (m, 1), 5.17 (s, 2), 6.80 (d, 2, J=10), 7.2–7.5 (m, 6).

Example 184

20 (7R)-7-[((2-N,N'-(bis)-tert-butyloxycarbonylguanidinoethylthio)acetyl)amino]-3-[2-(chloromethyl)phenylthio]-3-cephem-4-carboxylate, 4-methoxybenzyl ester To a stirring solution of N,N'-(bis)-di-tert-butyloxycarbonyl-S-methylisothiourea (2.37 g, 8.17 mmol) and 2-mercaptoethylamine hydrochloride (0.88 g, 7.78 mmol) at room temperature in THF (40 mL) was added triethylamine (1.2 mL, 8.56 mmol). The reaction was heated at 45°–50° C. for 7 h, after which the solvent was removed with a rotary evaporator. The residue was triturated with hexane/ethyl acetate, triethylamine hydrochloride was removed by filtration. The filtrate was concentrated and subjected to column chromatography on silica gel (2–5% ethyl acetate/hexanes), affording 1.08 g (44%) of 2-(N,N'-di-tert-butyloxycarbonylguanidino)ethanethiol. $^1$H NMR (CDCl$_3$) δ1.43 (t, 1, J=8), 1.48 (s, 18), 2.73 (dr, 2, J=8, 6), 3.63 (q, 2, J=6), 8.67 (br s, 2).

To a stirring solution of 2-(N,N'-di-tert-butyloxycarbonylguanidino)ethanethiol (1.08 g, 3.37 mmol) and methyl bromoacetate (516 mg, 3.37 mmol) in THF (10 mL) at 0° C. was added triethylamine (0.56 mL, 4.04 mmol). The mixture was allowed to warm to room temperature and was stirred overnight. The mixture was partitioned between ethyl acetate and water, and the aqueous layer was extracted with ethyl acetate. The combined organic phases were washed with water and brine, dried over sodium sulfate, and concentrated. The residue was subjected to column chromatography on silica gel (5–10% ethyl acetate/hexane), affording 1.24 g (95%) of methyl [2-(N,N'-di-tert-butyloxycarbonylguanidino)ethyl]thioacetate. $^1$H NMR (CDCl$_3$) δ1.48 (s, 18), 2.83 (t, 2, J=8), 3.26 (s, 2), 3.65 (q, 2, J=8), 3.73 (s, 3), 8.59 (br s, 2).

To a stirring solution of methyl [2-(N,N'-di-tert-butyloxycarbonylguanidino)ethyl]thioacetate (1.24 g, 3.17 mmol) in ethanol (15 mL) at room temperature (15 mL) was added 10% aqueous sodium hydroxide solution (3 mL). After 2 h, The mixture was concentrated, and the residue was treated with 10% aqueous HCl solution. The resulting mixture was extracted with ethyl acetate, and the organic extracts were washed with water and brine, dried over sodium sulfate, and concentrated to afford 1.06 g of [2-(N,N'-di-tert-butyloxycarbonylguanidino)ethyl]thioacetic acid as a white solid. $^1$H NMR (CDCl$_3$) δ1.50 (s, 18), 2.89 (t, 2, J=8), 3.34 (s, 2), 3.72 (m, 2), 8.82 (br s, 2).

To a stirring solution of [2-(N,N'-di-tert-butyloxycarbonylguanidino)ethyl]thioacetic acid (153 mg, 0.406 mmol) and (7R)-7-amino-3-(2-chloromethylphenylthio)-3-cephem-4-carboxylate, 4-methoxybenzyl ester, trifluoroacetate salt (200 mg, 0.334 mmol) at −20° C. in THF (8 mL) was added diisopropylethylamine (233 μL, 1.34 mmol) followed by phosphorus oxychloride (39 μL, 0.406 mmol). After 2 h, the mixture was partitioned between ethyl acetate and water, the layers were separated, and the organic layer was washed with saturated aqueous sodium bicarbonate solution, water, 10% aqueous HCl solution, and brine. After drying over sodium sulfate, the mixture was concentrated with a rotary evaporatory, and the residue was subjected to chromatography on silica gel (0–3% MeOH/dichloromethane), affording 228 mg (82%) of the title compound. $^1$H NMR (CDCl$_3$) δ1.51 (s, 18), 2.80 (t, 2, J=8), 3.22 (d, 1, J=18), 3.30 (d, 1, J=18), 3.34 (s, 2), 3.62 (m, 2), 3.82 (s, 3), 4.80 (s, 2), 5.01 (d, 1, J=4), 5.31 (s, 2), 5.75 (dd, 1, J-4, 9), 6.90 (d, 2, J=10), 7.3–7.6 (m, 7), 8.60 (br s, 2).

Example 185

(7R)-7-[((2-N,N'-(bis)-tert-butyloxycarbonylguanidinoethylthio)acetyl)amino]-3-[2-(iodomethyl)phenylthio]-3-cephem-4-carboxylate, 4-methoxybenzyl ester To a stirring solution of (7R)-7-[( (2-N,N'-(bis)-tert-butyloxycarbonylguanidinoethylthio)acetyl)amino]-3-[2-(chloromethyl)phenylthio]-3-cephem-4-carboxylate, 4-methoxybenzyl ester (228 mg, 0.273 mmol) at room temperature in acetonitrile (3 mL) was added sodium iodide (205 mg, 1.34 mmol). After stirring overnight, the mixture was partitioned between water and ethyl acetate, and the organic layer was washed with water and brine. The solvent was removed with a rotary evaporator, affording 239 mg (94%) of the title compound. $^1$H NMR (CDCl$_3$) δ1.51 (s, 18), 2.80 (t, 2, J=8), 3.28 (d, 1, J=18), 3.35 (s, 2), 3.37 (d, 1, J=18), 3.62 (m, 2), 3.82 (s, 3), 4.60 (d, 1, J=9), 4.63 (d, 1, J=9), 5.06 (d, 1, J=4), 5.29 (s, 2), 5.77 (dd, 1, J-4, 9), 6.89 (d, 2, J=10), 7.3–7.6 (m, 7), 8.60 (br s, 2).

Example 186

(7R)-7-[((2-N,N'-(bis)-tert-butyloxycarbonylguanidinoethylthio)acetyl)amino]-3-[2-(isothiouroniummethyl)phenylthio]-3-cephem-4-carboxylate, 4-methoxybenzyl ester To a stirring solution of (7R)-7-[((2-N,N'-(bis)-tert-butyloxycarbonylguanidinoethylthio)acetyl)amino]-3-[2(iodomethyl)phenylthio]-3-cephem-4-carboxylate, 4-methoxybenzyl ester (239 mg, 0.258 mmol) at room temperature in acetonitrile (2 mL) was added thiourea (19 mg, 0.258 mmol). After 4 h, the solvent was removed with a rotary evaporator, and the residue was triturated with ether, filtered, and dried, affording 240 mg (93%) of the title compound. $^1$H NMR (CDCl$_3$) δ1.48 (s, 18), 2.81 (m, 2), 3.21 (d, 1, J=18), 3.40 (s, 2), 3.42 (d, 1, J=18), 3.60 (m, 2), 3.80 (s, 3), 4.70 (d, 1, J=11), 4.87 (d, 1, J=11), 5.12 (d, 1, J=4), 5.27 (s, 2), 5.56 (dd, 1, J-4, 9), 6.50 (br s, 1), 6.89 (d, 2, J=10), 7.3–7.6 (m, 6), 8.15 (d, 1, J=9), 8.50 (v br s, 1), 8.66 (br s, 1).

Example 187

(7R)-7-[((2-guanidinoethylthio)acetyl)amino]-3-[2-(isothiouroniummethyl)phenylthio]-3-cephem-4-carboxylate, trifluoroacetic acid salt To a mixture of (7R)-7-[((2-N,N'-(bis)-tert-butyloxycarbonylguanidinoethylthio)acetyl)amino]-3-[2(isothiouroniummethyl)phenylthio]-3-cephem-4-carboxylate, 4-methoxybenzyl ester (240 mg, 0.240 mmol) and anisole (100 μL) at room temperature was added trifluoroacetic acid (1.5 mL). After 1.5 h, the volatiles were removed in vacuo, and the residue was triturated with ether. The resulting solid was dried, and was suspended in water (50 mL), filtered, and lyophilized to afford 131 mg (82%) of the title compound. 1H NMR (D$_2$O) δ2.83 (t, 2, J=7), 3.25 (d, 1, J=18), 3.38 (s, 2), 3.42 (t, 2, J=7), 3.48 (d, 1, J=18), 4.59 (s, 2), 5.20 (d, 1, J=4), 5.59 (d, 1, J=4), 7.4–7.6 (m, 4).

Under substantially the same procedures as in Examples 184–187, the items of the following Examples 188–219 can similarly be obtained.

Example 188

(7R)-7-[((3-guanidinopropylthio)acetyl)amino]-3-[2-(isothiouroniummethyl)phenylthio]-3-cephem-4-carboxylate, trifluoroacetic acid salt Example 189

(7R)-7-[((4-guanidinobutylthio)acetyl)amino]-3-[2-(isothiouroniummethyl)phenylthio]-3-cephem-4-carboxylate, trifluoroacetic acid salt Example 190

(7R)-7-[((2-N,N'-dimethylguanidinoethylthio) acetyl) amino]-3-[2-(isothiouroniummethyl)phenylthio]-3-cephem-4-carboxylate, trifluoroacetic acid salt Example 191

(7R)-7-[((3-N,N'-dimethylguanidinopropylthio) acetyl)amino]-3-[2-isothiouroniummethyl)phenylthio]-3-cephem-4-carboxylate, trifluoroacetic acid salt Example 192

(7R)-7-[( (4-N,N'-dimethylguanidinobutylthio) acetyl)amino]-3-[2-(isothiouroniummethyl)phenylthio]-3-cephem-4-carboxylate, trifluoroacetic acid salt Example 193

(7R)-7-[((2-isothiouronium)ethylthioacetyl)amino]-3-[2-(isothiouroniummethyl)phenylthio]-3-celphem-4-carboxylate, trifluoroacetic acid salt Example 194

(7R)-7-[((3-isothiouroniumpropyl)thioacetyl)amino]-3-[2-(isothiouroniummethyl)phenylthio]-3-cephem-4-carboxylate, trifluoroacetic acid salt Example 195

(7R)-7-[((4-isothiouroniumbutyl)thioacetyl)amino]-3-[2-(isothiouroniummethyl)phenylthio]-3-cephem-4-carboxylate, trifluoroacetic acid salt Example 196

(7R)-7-[( (2-N,N'-dimethylisothiouronium)ethylthioacetyl)amino]-3-[2-(isothiouroniummethyl) phenylthio]-3-cephem-4-carboxylate, trifluoroacetic acid salt Example 197

(7R)-7-[((3-N, N'dimethylisothiouroniumproyl)thioacetyl)amino]-3-[2-(isothiouroniummethyl)phenylthio]-3-cephem-4-carboxylate, trifluoroacetic acid salt Example 198

(7R)-7-[((4-N,N'-dimethylisothiouroniumbutyl)thioacetyl)amino]-3-[2-(isothiouroniummethyl) phenylthio]-3-cephem-4-carboxylate, trifluoroacetic acid salt Example 199

(7R)-7-[((2-tetramethylisothiouronium)ethylthioacetyl)amino]-3-[2-(isothiouroniummethyl) phenylthio]-3-cephem-4-carboxylate, trifluoroacetic acid salt Example 200

(7R)-7-[((3-tetramethylisothiouroniumpropylthioacetyl)amino]-3-[2-(isothiouroniummethyl) phenylthio]-3-cephem-4-carboxylate, trifluoroacetic acid salt

Example 201

(7R)-7-[((4-tetramethylisothiouroniumbutyl)thioacetyl)amino]-3-[2-(isothiouroniummethyl)phenylthio]-3- cephem-4-carboxylate, trifluoroacetic acid salt

Example 202

(7R)-7-[(2-(iminomethyl)amino)ethylthioacetyl)amino]-3-[2-(isothiouroniummethyl)phenylthio]-3-cephem-4-carboxylate, trifluoroacetic acid salt

Example 203

(7R)-7-[(2-((N-methyliminomethyl)amino)ethylthioacetyl)amino]-3-[2-(isothiouroniummethyl)phenylthio]-3-cephem-4-carboxylate, trifluoroacetic acid salt

Example 204

(7R)-7-[(3((iminomethyl)amino)propylthioacetyl)amino]-3-[2-(isothiouroniummethyl)phenylthio]-3-cephem-4-carboxylate, trifluoroacetic acid salt

Example 205

(7R)-7-[(3-((N-methyliminomethyl)amino)propylthioacetyl)amino]-3-[2-(isothiouroniummethyl)phenylthio]-3-cephem-4-carboxylate, trifluoroacetic acid salt

Example 206

(7R)-7-[(4-((iminomethyl)amino)butylthioacetyl)amino]-3-[2-(isothiouroniummethyl)phenylthio]-3-cephem-4-carboxylate, trifluoroacetic acid salt

Example 207

(7R)-7-[(4-((N-methyliminomethyl)amino)butylthioacetyl)amino]-3-[2(isothiouroniummethyl)phenylthio]-3-cephem-4-carboxylate, trifluoroacetic acid salt

Example 208

(7R)-7-[((2-amidinium)ethylthioacetyl)amino]-3-[2-(isothiouroniummethyl)phenylthio]-3-cephem-4-carboxylate, trifluoroacetic acid salt

Example 209

(7R)-7-[((3-amidiniumpropyl)thioacetyl)amino]-3-[2-(isothiouroniummethyl)phenylthio]-3-cephem-4-carboxylate, trifluoroacetic acid salt

Example 210

(7R)-7-[((4-amidiniumbutyl)thioacetyl)amino]-3-[2-(isothiouroniummethyl)phenylthio]-3-cephem-4-carboxylate, trifluoroacetic acid salt

Example 211

(7R)-7-[(2-(N,N'-dimethylamidinium)ethylthioacetyl)amino]-3-[2(isothiouroniummethyl)phenylthio]-3-cephem-4-carboxylate, trifluoroacetic acid salt

Example 212

(7R)-7-[((3-(N,N'-dimethylamidinium)propyl)thioacetyl)amino]-3-[2-(isothiouroniummethyl)phenylthio]-3-cephem-4-carboxylate, trifluoroacetic acid salt

Example 213

(7R)-7-[((4-(N,N'-dimethylamidinium)butyl)thioacetyl)amino]-3-[2-(isothiouroniummethyl)phenylthio]-3-cephem-4-carboxylate, trifluoroacetic acid salt

Example 214

(7R)-7-[((2-(tetramethylamidinium) ethyl)thioacetyl)amino]-3-[2-(isothiouroniummethyl)phenylthio]-3-cephem-4-carboxylate, trifluoroacetic acid salt

Example 215

(7R)-7-[((3-(tetramethylamidinium) propyl)thioacetyl)amino]-3-[2-(isothiouroniummethyl)phenylthio]-3-cephem-4-carboxylate, trifluoroacetic acid salt

Example 216

(7R)-7-[((4-(tetramethylamidinium)butyl) thioacetyl) amino]-3-[2-(isothiouroniummethyl)phenylthio]-3-cephem-4-carboxylate, trifluoroacetic acid salt

Example 217

(7R)-7-[((2-amidinium)methylthioacetyl)amino]-3-[2-(isothiouroniummethyl)phenylthio]-3-cephem-4-carboxylate, trifluoroacetic acid salt

Example 218

(7R)-7-[((2-N,N'-dimethylamidinium) methylthio-acetyl)amino]-3-[2-(isothiouroniummethyl)phenylthio]-3-cephem-4-carboxylate, trifluoroacetic acid salt

Example 219

(7R)-7-[((2-tetramethylamidinium)methylthioacetyl)amino]-3-[2-(isothiouroniummethyl)phenylthio]-3- cephem-4-carboxylate, trifluoroacetic acid salt Thus, it will be appreciated that the compounds, methods and compositions of the invention are effective against various β-lactam resistant strains of bacteria which pose an increasing health risk to society.

Although certain embodiments and examples have been used to describe the present invention, it will be apparent to those skilled in the art that changes to the embodiments and examples shown may be made without departing from the scope or spirit of the invention.

Those references not previously incorporated herein by reference, including both patent and non-patent references, are expressly incorporated herein by reference for all purposes.

Other embodiments are within the following claims.

What is claimed:

1. A compound active against methicillin resistant bacterial infections, as demonstrated by a lower minimum inhibitory concentration against methicillin resistant strains than cefotaxime, having the formula:

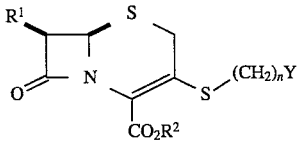

and its pharmaceutically acceptable salts, wherein $R^1$ is —NHC(O) $ZR^3$ or —$NR^4R^5$, where Z is —$CH_2(X)_m$—, —$C(NOR^6)$—, —$CH(OR^7)$—, —$C(CHCO_2R^9)$— or —$CH(NR^9R^{10})$—, wherein X is O or S and m is 0 or 1; $R^3$ is selected from the group consisting of cyano, alkyl, aryl, heterocycycle and heteroaralkyl; $R^{4-7}$ are selected independently from the group consisting of hydrogen, alkyl, aryl and acyl; $R^8$ is selected from the group consisting of hydrogen, alkyl and aryl; and, $R^9$ and $R^{10}$ are selected independently from the group consisting of hydrogen, alkyl, acyl, and heterocyclecarbonyl;

or $R^1$ is

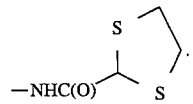

$R^2$ is hydrogen, alkyl, alkenyl, aryl, heterocycle, aralkyl, heteroaralkyl, or trialkylsilyl;

n is 0 or 1; and

Y is heterotricycle.

2. The compound of claim 1, wherein $R^1$ is —NHC(O) $ZR^3$ or $R^1$ is

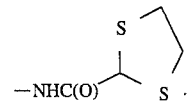

3. The compound of claim 2, wherein $R^3$ is alkyl, cyano, aryl or heterocycle.

4. The compound of claim 2, wherein $R^3$ is selected from the group consisting of methyl, cyano, phenyl, thienyl, furanyl, and 2-aminothiazolyl.

5. The compound of claim 2 wherein Z is —$CH_2(X)_m$—, X is S, and m is 0 or 1.

6. The compound of claim 5 wherein m is 1 and $R^3$ is alkyl substituted with a substituent selected from the group consisting of guanidino, isothioureido, and amidino.

7. The compound of claim 2, wherein Z is —$C(NOR^6)$—, $R^6$ is selected from the group consisting of hydrogen and alkyl, and $R^3$ is aryl or heterocycle.

8. The compound of claim 2, wherein $R^6$ is selected from the group consisting of 2-fluoroethyl, cyclopropylmethyl, allyl, dichloroallyl and cyclopentyl, and $R^3$ is selected from the group consisting of phenyl, 2-thienyl, 2-furyl and 2-aminothiazol-4-yl.

9. The compound of claim 1, wherein Y is selected from the group consisting of 1-dibenzfuranyl, 2-dibenzfuranyl, 3-dibenzfuranyl, 4-dibenzfuranyl, 1-dibenzthienyl, 2-dibenzthienyl, 3-dibenzthienyl, and 4-dibenzthienyl.

10. The compound of claim 1, wherein Y is optionally substituted with acyl, alkyl, hydroxyl, halogen, carbonyl, thioalkyl, amido, alkoxyl, trialkylammonium, cyanoalkylamido, imidazolyl, thiazolyl, oxazolyl, imidazolylmethyl, thiazolylmethyl, oxazolylmethyl, imidazolium, imidazoliummethyl, thienyl, thienylmethyl, furyl, furylmethyl, pyridinium, cyano, pyridyl, pyrrolyl, pyrazolyl, triazolyl, or tetrazolyl.

11. The compound of claim 1, wherein Y is an optionally substituted dibenzfuranyl, or dibenzthienyl; n is 0; and said substituent is at the 2-position of the optionally substituted ring relative to the point of ring attachment to the sulfur atom.

12. A method of treating a mammal suffering from a methicillin resistant or methicillin sensitive bacterial infection, comprising administering to such mammal a therapeutically effective amount of a compound of claim 1 to thereby at least partially relieve said mammal from said methicillin resistant or methicillin sensitive bacterial infection.

13. The method of claim 12, wherein said mammal is infected with a methicillin resistant or methicillin sensitive Staphylococcal or Enterococcal organism.

14. An antibacterial composition for treating a methicillin resistant or methicillin sensitive bacterial infection, comprising a therapeutically effective amount of a compound of claim 1 in a pharmaceutically acceptable carrier.

15. The composition of claim 14 for treating a methicillin resistant or methicillin sensitive Staphylococcal or Enterococcal infection.

\* \* \* \* \*

UNITED STATES PATENT AND TRADEMARK OFFICE
CERTIFICATE OF CORRECTION

PATENT NO. : 5,607,926
DATED : March 4, 1997
INVENTOR(S) : Scott J. Hecker, et al.

It is certified that error appears in the above-identified patent and that said Letters Patent is hereby corrected as shown below:

Column 2, Line 42: delete "betalactam" and insert --beta-lactam--.

Column 7, Line 48: delete "isobutylthio" and insert --iso-butylthio--.

Column 14, Line 15: delete "byway" and insert --by way--.

Column 19, Line 31: delete "$\leq$" and insert --$\leq$--.

Column 20, Line 29: after "7-" insert --[--.

Column 42, Line 42: delete "product-was" and insert --product was--.

Column 43, Line 24: delete "4dichlorophenylthio" and insert --4-dichlorophenylthio--.

Column 60, Line 66: delete "0,670" and insert --0.670--.

Column 69, Line 30: after "slowly" insert --to--.

Column 69, Line 57: delete "be" and insert --by--.

Column 76, Line 50: delete "mina" and insert --min a--.

UNITED STATES PATENT AND TRADEMARK OFFICE
CERTIFICATE OF CORRECTION

PATENT NO. : 5,607,926
DATED : March 4, 1997
INVENTOR(S) : Scott J. Hecker, et al.

It is certified that error appears in the above-identified patent and that said Letters Patent is hereby corrected as shown below:

Column 85, Line 46, Claim 1: delete "C(CHCO$_2$R$^9$)" and insert --C(CHCO$_2$R$^8$)--.

Column 85, Line 48, Claim 1: delete "heterocycycle" and insert --heterocycle--.

Column 86, Line 39, Claim 10: delete "or" and insert --and--.

Signed and Sealed this

Seventh Day of April, 1998

*Attest:*

BRUCE LEHMAN

*Attesting Officer*  Commissioner of Patents and Trademarks